(12) United States Patent
Wang et al.

(10) Patent No.: US 7,674,787 B2
(45) Date of Patent: Mar. 9, 2010

(54) CONFORMATIONALLY CONSTRAINED SMAC MIMETICS AND THE USES THEREOF

(75) Inventors: Shaomeng Wang, Saline, MI (US); Haiying Sun, Ann Arbor, MI (US); Zaneta Nikolovska-Coleska, Ann Arbor, MI (US); Chao-Yie Yang, Ann Arbor, MI (US); Liang Xu, Ann Arbor, MI (US); Naoyuki G. Saito, Ann Arbor, MI (US); Jianyong Chen, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/632,079

(22) PCT Filed: Jul. 11, 2005

(86) PCT No.: PCT/US2005/024530

§ 371 (c)(1),
(2), (4) Date: Feb. 20, 2008

(87) PCT Pub. No.: WO2006/010118

PCT Pub. Date: Jan. 26, 2006

(65) Prior Publication Data

US 2008/0132485 A1 Jun. 5, 2008

Related U.S. Application Data

(60) Provisional application No. 60/586,575, filed on Jul. 9, 2004.

(51) Int. Cl.
*C07D 223/16* (2006.01)
*A01N 43/00* (2006.01)
*A61K 31/55* (2006.01)

(52) U.S. Cl. .................... 514/213.01; 540/484; 540/593

(58) Field of Classification Search ................ 540/593, 540/484; 514/212.07, 213.01
See application file for complete search history.

(56) References Cited

U.S. PATENT DOCUMENTS 6,608,026 B1  8/2003  Wang
7,244,851 B2  7/2007  Cohen

OTHER PUBLICATIONS

Arnt, Christina R., et al., "Synthetic Smac/DIALO Peptides Enhance the Effects of Chemotherapeutic Agents by Binding XIAP and cIAP1 in Situ," The Journal of Biological Chemistry, vol. 277, No. 46, Nov. 15, 2002, pp. 44236-44243.
Ashkenazi, Avi, et al., "Death Receptors: Signaling and Modulation," Science, vol. 281, Aug. 28, 1998, pp. 1305-1308.
Budihardjo, Imawati, et al., "Biochemical Pathways of Caspase Activation During Apoptosis," Annu. Rev. Cell. Dev. Biol. (1999) 15:269-90.

Du, Chunying, et al., "Smac, a Mitochondrial Protein that Promotes Cytochrome c-Dependent Caspase Activation by Eliminating IAP Inhibition," Cell, vol. 102, pp. 33-42, Jul. 7, 2000.
Ekert, Paul G., et al., "DIABLO Promotes Apoptosis by Removing MIHA/XIAP from Processed Caspase 9," The Journal of Cell Biology, vol. 152, No. 3, Feb. 5, 2001, pp. 483-490.
French, Lars E., "The TRAIL to Selective Tumor Death," Nature Medicine, vol. 5, No. 2, Feb. 1999, pp. 146-.
Fulda, Simone, et al., "Smac agonists sensitize for Apo2L/TRAIL- or anticancer drug-induced apoptosis and induce regression of malignant glioma in vivo," Nature Medicine, vol. 8, No. 8, Aug. 2002.
Griffith, Thomas S., et al., "Intracellular Regulation of TRAIL-Induced Apoptosis in Human Melanoma Cells," The Journal of Immunology, vol. 161, No. 6, Sep. 15, (1998), pp. 2833-2840.
Holcik, Martin, et al., "Translational upregulation of X-linked inhibitor of apoptosis (XIAP) increases resistance to radiation induced cell death," Onogene (2000) pp. 4174-4177.
Kataoka, Takao, et al., "FLIP Prevents Apoptosis Induced by Deah Receptors But Not by Perforin/Granzyme B, Chemotherapeutic Drugs, and Gamma Irradiation," The Journal of Immunology, vol. 161, No. 8, Oct. 15, 1998, pp. 3936-3942.
Kim, Kunbong, et al., "Molecular Determinants of Resonse of TRAIL in Killing of Normal and Cancer Cells," Clinical Cancer Research, vol. 6, pp. 335-346, Feb. 2000.
Kischkel, Frank C., et al., "Apo2L/TRAIL-Dependent Recruitment of Endogenous FADD and Caspase-8 to Death Receptors 4 and 5," Immunity, vol. 12, pp. 811-820, Jun. 2000.
Kuang, Anna A., et al., "FADD is Required for DR4- and DR5-mediated Apoptosis," The Journal of Biological Chemistry, vol. 275, No. 33, Aug. 18, 2000, pp. 25065-25068.
Medema, Jan Paul, "FLICE is activated by association with the CD95 death-inducing signaling complex (DISC)," The EMBO Journal, vol. 16, No. 10, pp. 2794-2804 (1997).
Muzio, Marta, et al., "An Induced Proximity Model for Caspase-8 Activation," The Journal of Biological Chemistry, vol. 278, No. 5, Jan. 20, 1998, pp. 2926-2930.
Pan, Guohua, et al., "The Receptor for the Cytotoxic Ligand TRAIL," Science, vol. 276, Apr. 4, 1997, pp. 111-113.
Pan, Guohua, et al., "An Antagonist Deco Receptor and a Death Domain-Containing Receptor for TRAIL," Science, vol. 277, Aug. 8, 1997, pp. 815-818.
Srinivasula, et al., "A conserved XIAP-interaction motif in caspase-9 and Smac/DIABLO regulates caspase activity and apoptosis," Nature vol. 410, Mar. 2001, pp. 112-116.
Srinivasula, et al., "Molecular Determinants of the Caspase-promoting Activity of Smac/DIABLO and Its Role in the Death Receptor Pathway," The Journal of Biological Chemistry, vol. 275, No. 45, Nov. 17, 2000, pp. 36152-36157.

(Continued)

*Primary Examiner*—James O. Wilson
*Assistant Examiner*—Paul V. Ward
(74) *Attorney, Agent, or Firm*—Casimir Jones SC

(57) ABSTRACT

The invention relates to conformationally constrained mimetics of Smac which function as inhibitors of Inhibitor of Apoptosis Proteins. The invention also relates to the use of these mimetics for inducing apoptotic cell death and for sensitizing cells to inducers of apoptosis.

4 Claims, 35 Drawing Sheets

OTHER PUBLICATIONS

Sun, Chaohong, et al., "NMR Structure and Mutagenesis of the Third Bir Domain of the Inhibitor of Apoptosis Protein XIAP," The Journal of Biological Chemistry, vol. 275, No. 43, Oct. 27, 2000, pp. 33777-33781.

Teitz, Tal, et al., "Caspase 8 is deleted or silenced preferentially in childhood neuroblastomas with amplification of MYCN," Nature Medicine, vol. 6, No. 5, May 2000, pp. 529-535.

Walczak, Henning, et al., "TRAIL-R2: a novel apoptosis-mediating receptor for TRAIL," The EMBO Journal, vol. 16, No. 17, pp. 5386-5397 (1997).

Walczak, Henning, et al., "Tumoricidal activity of tumor necrosis factor-related poptosis-inducing ligand inv vivo," Nature Medicine, vol. 5, No. 2, Feb. 1999, pp. 157-163.

Wu, "KILLER/DR5 is a DNA damage-inducible p53-regulated death receptor gene," Nature Genetics, vol. 17, Oct. 1997, pp. 141-143.

Wu, et al., "Structural basis of IAP recognition by Smac/DIABLO," Nature, vol. 408, Dec. 2000, pp. 1008-1012.

Yang, Lilling, "Predominant Suppression of Apoptosome by Inhibitor of Apoptosis Protein in Non-Small Cell Lung Cancer H460 Cells: Therapeutic Effect of a Novel Polyarginine-conjugated Smac Peptide," Cancer Research 63, pp. 831-837, Feb. 5, 2003.

Zhang, et al., "Relation of NF-related Apoptosis-inducing Ligand (TRAIL) Receptor and FLICE-inhibitory Protein Expression to TRAIL-induced Apoptosis of Melanoma," Cancer Research 59, pp. 2747-2753, Jun. 1, 1999.

US 7,674,787 B2

CONFORMATIONALLY CONSTRAINED SMAC MIMETICS AND THE USES THEREOF

CROSS REFERENCE TO RELATED APPLICATIONS

This application is a 371 national stage application of International Patent Application No. PCT/US2005/024530, international filing date Jul. 11, 2005, which claims priority to expired U.S. Provisional Patent Application No. 60/586,575 filed Jul. 9, 2004, both of which are hereby incorporated by reference in their entireties.

BACKGROUND OF THE INVENTION

1. Field of the Invention

This invention is in the field of medicinal chemistry. In particular, the invention relates to conformationally constrained mimetics of Smac which function as inhibitors of Inhibitor of Apoptosis Proteins. The invention also relates to the use of these mimetics for sensitizing cells to the induction of apoptotic cell death.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407:810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the Bcl-2 family of proteins, as exemplified by two potent anti-apoptotic molecules, Bcl-2 and Bcl-$X_L$ proteins (Adams et al., Science 281:1322 (1998); Reed, Adv. Pharmacol. 41:501 (1997); Reed et al., J. Cell. Biochem. 60:23 (1996)). Therapeutic strategies for targeting Bcl-2 and Bcl-$X_L$ in cancer to restore cancer cell sensitivity and overcome resistance of cancer cells to apoptosis have been extensively reviewed (Adams et al., Science 281:1322 (1998); Reed, Adv. Pharmacol. 41:501 (1997); Reed et al., J. Cell. Biochem. 60:23 (1996)). Currently, Bcl-2 antisense therapy is in several Phase III clinical trials for the treatment of solid and non-solid tumors. Several laboratories are interested in designing small molecule inhibitors of Bcl-2 and Bcl-$X_L$.

The second class of central negative regulators of apoptosis is the inhibitor of apoptosis proteins (IAPs) (Deveraux et al., Genes Dev. 13:239 (1999); Salvesen et al., Nat. Rev. Mol. Cell. Biol. 3:401 (2002)). IAP proteins potently suppress apoptosis induced by a large variety of apoptotic stimuli, including chemotherapeutic agents, radiation, and immunotherapy in cancer cells.

X-linked IAP (XIAP) is the most potent inhibitor in suppressing apoptosis among all of the IAP members (Holcik et al., Apoptosis 6:253 (2001); LaCasse et al., Oncogene 17:3247 (1998); Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001)). XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family of enzymes, caspase-3, -7, and -9 (Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001); Riedl et al., Cell 104:791 (2001); Chai et al., Cell 104:769 (2001); Huang et al., Cell 104:781 (2001)). XIAP contains three baculovirus inhibitor of apoptosis repeat (BIR) domains as well as a C-terminal RING finger. The third BIR domain (BIR3) selectively targets caspase-9, the initiator caspase in the mitochondrial pathway, whereas the linker region between BIR1 and BIR2 inhibits both caspase-3 and caspase-7 (Salvesen et al., Nat. Rev. Mol. Cell. Biol. 3:401 (2002)). While binding to XIAP prevents the activation of all three caspases, it is apparent that the interaction with caspase-9 is the most critical for its inhibition of apoptosis (Ekert et al., J. Cell Biol. 152:483 (2001); Srinivasula et al., Nature 410:112 (2001)). Because XIAP blocks apoptosis at the down-stream effector phase, a point where multiple signaling pathways converge, strategies targeting XIAP may prove to be especially effective to overcome resistance of cancer cells to apoptosis (Fulda et al., Nature Med. 8:808 (2002); Arnt et al., J. Biol. Chem. 277:44236 (2002)).

Although the precise role of XIAP in each type of cancer is far from completely understood, evidence is mounting to indicate that XIAP is widely overexpressed in many types of cancer and may play an important role in the resistance of cancer cells to a variety of current therapeutic agents (Holcik et al., Apoptosis 6:253 (2001); LaCasse et al., Oncogene 17:3247 (1998)).

XIAP protein was found to be expressed in most of the NCI 60 human cancer cell lines (Tamm et al., Clin. Cancer Res. 6:1796 (2000)). Analysis of tumor samples in 78 previously untreated patients showed that those with lower levels of XIAP had significantly longer survival (Tamm et al., Clin. Cancer Res. 6:1796 (2000)). XIAP was found to be expressed in human malignant glioma (Wagenknecht et al., Cell Death Differ. 6:370 (1999); Fulda et al., Nature Med. 8:808 (2002)). XIAP was found to be expressed in human prostate cancer cells and blocks Apo2 ligand/tumor necrosis factor-related apoptosis inducing ligand-mediated apoptosis of prostate cancer cells in the presence of mitochondrial activation (McEleny et al., Prostate 51:133 (2002); Ng et al., Mol. Cancer. Ther. 1:1051 (2002)). XIAP is overexpressed in non-small cell lung cancer (NSCLC) in patients and has been implicated in pathogenesis of NSCLC (Hofmann et al., J. Cancer Res. Clin. Oncol. 128:554 (2002)). Expression of XIAP and lack of down-regulation of XIAP upon treatment with cisplatin have been implicated in cisplatin resistance of human ovarian cancer (Li et al., Endocrinology 142:370 (2001); Cheng et al., Drug Resist. Update 5:131 (2002)).

Taken together, these data suggest that XIAP may play an important role in resistance of several human cancers to current therapeutic agents.

Apoptosis is not a single process, rather, it is involved with a number of different, sometimes interconnected, signaling pathways leading to cell degradation. The pathways involved in a particular form of apoptosis depend on many factors, such as the insult or insults that initiate the process. Other factors include the activation or overactivation of specific receptors, such as the activation of "death" receptors by tumor necrosis factor alpha (TNFα), tumor necrosis factor-related apoptosis-inducing ligand (TRAIL or Apo2L), or FAS ligand. Another determining factor is the type of cell which is involved, since different signaling pathways are shown for so called type I and type II cells after Fas or TNFα receptor activation.

TRAIL (Apo2L) has been shown to be a selective and potent inducer of apoptosis in cancer cells (but not normal cells) upon binding to either of two pro-apoptotic TRAIL receptors, TRAIL R1 (or DR4) (Pan et al., *Science* 276:111 (1997)) or TRAIL R2 (KILLER, or DR5) (Wu et al., *Nat. Genet.* 17:141-143 (1997); Pan et al., *Science* 277:815 (1997); Walczak et al., *EMBO J.* 16:5386 (1997)). Activation of the pro-apoptotic death receptors by TRAIL induces the formation of death inducing signaling complex (DISC), which consists of receptor FADD as an adaptor (Kischkel et al., *Immunity* 12:611 (2000); Kuang et al., *J. Biol. Chem.* 275:25065 (2000)), and caspase-8 as an initiator caspase. Once DISC is formed, caspase-8 is auto-processed and activated by induced proximity (Medema et al., *EMBO J.* 16:2794 (1997); Muzio et al., *J. Biol. Chem.* 273:2926 (1998)).

TRAIL has generated significant interest as a potential cancer therapeutic (French et al., *Nat. Med.* 5:146 (1999)) because of its selective targeting of cancer cells, whereas most normal cells appear to be resistant to TRAIL (Ashkenazi et al., *Science* 281:1305 (1998); Walczak et al., *Nat. Med.* 5:157 (1999)). Systemic administration of TRAIL has proven to be safe and effective at killing breast or colon xenografted tumors and prolonging survival in mice (Walczak et al., *Nat. Med.* 5:157 (1999)). Although TRAIL can specifically kill many types of cancer cells, many others display TRAIL-resistance (Kim et al., *Clin. Cancer Res.* 6:335 (2000); Zhang et al., *Cancer Res.* 59:2747 (1999)). In addition, cancer cells have been killed by application of antibodies (monoclonal or polyclonal) that specifically recognize either TRAILR1 or TRAILR2.

Numerous mechanisms have been identified as potential factors responsible for TRAIL-resistance. Such mechanisms exist at a number of levels, including at the receptor level, mitochondria level, post-mitochondria level, and at the DISC level. For example, loss of caspase-8 expression (Teitz et al., *Nat. Med.* 6:529 (2000); Griffith et al., *J. Immunol.* 161:2833 (1998)), or high expression of the cellular FLICE inhibitor protein (cFLIP) (Kim et al., *Clin. Cancer Res.* 6:335 (2000); Zhang et al., 1999; Kataoka et al., *J. Immunol.* 161:3936 (1998)) make cancer cells resistant to TRAIL. Yeh et al. have shown that cFLIP-deficient embryonic mouse fibroblasts are particularly sensitive to receptor-mediated apoptosis (Yeh et al., *Immunity* 12:533 (2000)). Several splice variants of cFLIP are known, including a short splice variant, cFLIP-S, and a longer splice variant, cFLIP-L. It has been shown that cFLIP-deficient embryonic mouse fibroblasts become resistant to TRAIL-induced apoptosis as a result of retroviral-mediated transduction of cFLIP-S (Bin et al., *FEBS Lett.* 510:37 (2002)).

Although TRAIL represents a particularly promising candidate for tumor-selective death receptor activation (i.e., it induces apoptosis preferentially in tumor cells but not in normal tissues), many cancer cells are resistant to apoptosis-inducing drugs, as discussed above. As a result, treatment with such drugs often requires co-treatment with irradiation and/or cytotoxic chemicals to achieve a therapeutic effect. However, both radiation and chemotherapy have significant side effects, and are generally avoided if possible.

Thus, a need exists for an agent that can selectively and efficiently sensitize tumor cells for apoptosis-inducing drugs such as TRAIL or TRAIL receptor antibodies, without also sensitizing the surrounding normal cells. Such an agent would be useful for reducing or preventing the drug resistance commonly associated with the use of receptor-mediated apoptotic cancer drugs, thus improving their effectiveness and eliminating the need for combination therapies.

Recently, Smac/DIABLO (second mitochondria-derived activator of caspases) was identified as a protein released from mitochondria into the cytosol in response to apoptotic stimuli (Budihardjo et al., *Annu. Rev. Cell Dev. Biol.* 15:269 (1999); Du et al., *Cell* 102:33 (2000)). Smac is synthesized with an N-terminal mitochondrial targeting sequence that is proteolytically removed during maturation to the mature polypeptide. Smac was shown to directly interact with XIAP and other IAPs and to disrupt their binding to caspases and facilitate caspase activation. Smac is a potent endogenous inhibitor of XIAP.

High resolution, experimental three-dimensional (3D) structures of the BIR3 domain of XIAP in complex with Smac protein and peptide have recently been determined (Sun et al., *J. Biol. Chem.* 275:36152 (2000); Wu et al., *Nature* 408:1008 (2000)) (FIG. 1). The N-terminal tetrapeptide of Smac (Ala-Val-Pro-Ile, or AVPI (SEQ ID NO:1)) recognizes a surface groove on the BIR3 domain of XIAP through several hydrogen-bonding interactions and van der Waals contacts. The interaction between BIR3 and caspase-9 has also been shown to involve four residues (Ala-Thr-Pro-Phe, or ATPF (SEQ ID NO:2)) on the amino terminus of the small subunit of caspase-9 to the same surface groove on the BIR3 domain. Several recent studies have convincingly demonstrated that Smac promotes the catalytic activity of caspase-9 by competing with caspase-9 for the same binding groove on the surface of the BIR3 domain (Ekert et al., *J. Cell Biol.* 152:483 (2001); Srinivasula et al., *Nature* 410:112 (2001)).

Unlike most protein-protein interactions, the Smac-XIAP interaction is mediated by only four amino acid residues on the Smac protein and a well-defined surface groove on the BIR3 domain of XIAP. The $K_d$ value of Smac peptide AVPI (SEQ ID NO:1) to XIAP ($K_d$=0.4 µM) is essentially the same as the mature Smac protein ($K_d$=0.42 µM). This well-defined interaction site is ideal for the design of non-peptide, drug-like small molecules that mimic the binding of Smac to XIAP.

A cell permeable Smac peptide, which consists of the first four amino acid residues (AVPI (SEQ ID NO:1)) of the N-terminus of Smac tethered to a carrier peptide to facilitate intracellular delivery, was recently shown to sensitize various tumor cells in vitro and malignant glioma cells in vivo to apoptosis induced by death receptor ligation or cytotoxic drugs (Fulda et al., *Nature Med.* 8:808 (2002)). Importantly, this Smac peptide strongly enhanced the anti-tumor activity of Apo2L/TRAIL in an intracranial malignant glioma xenograft model in vivo. Complete eradication of established tumors and survival of mice was only achieved upon combined treatment with Smac peptides and Apo2L/TRAIL. Of significance, Smac peptide does not have detectable toxicity to normal brain tissue.

A second recent independent study also showed that peptides consisting of the first four to eight amino acid residues of the N-terminus of Smac tethered to a different carrier peptide enhanced the induction of apoptosis and the long term antiproliferative effects of diverse chemotherapeutic drugs, including paclitaxel, etoposide, SN-38, and doxorubicin in MCF-7 and other human breast cancer cell lines (Arnt et al., *J. Biol. Chem.* 277:44236 (2002). This study conclusively showed that XIAP and cIAP-1 are the primary molecular targets for these peptides in cells.

A third study showed that a Smac peptide of the first seven N-terminal residues tethered to polyarginine restored the apoptosome activity and reversed the apoptosis resistance in non-small cell lung cancer H460 cells (Yang et al., *Cancer Res.* 63:831 (2003)). XIAP was shown to be responsible for the defect in apoptosome activity and suppression of caspase activity in H460 cells. When used in combination with chemotherapy, the cell-permeable Smac peptide regressed the tumor growth in vivo with little toxicity to the mice. Taken together, these recent independent studies strongly suggest that a potent, stable, cell-permeable Smac mimetic may have great therapeutic potential for the treatment of human breast cancer and other types of cancer.

Peptide-based inhibitors are useful tools to elucidate the anti-apoptotic function of IAPs and the role of IAPs in response of cancer cells to chemotherapeutic agents. But peptide-based inhibitors in general have intrinsic limitations as potentially useful therapeutic agents. These limitations include their poor cell-permeability and poor in vivo stability. Indeed, in these three published studies using Smac-based peptide inhibitors, the peptides had to be fused to carrier peptides to make them relatively cell-permeable.

To overcome the intrinsic limitations of peptide-based inhibitors, the present invention involves the design of non-peptidic mimetics based upon Smac peptide and the high resolution experimental three dimensional structures of Smac in complex with XIAP BIR3 domain.

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of IAPs.

The present invention contemplates that exposure of animals suffering from cancer to therapeutically effective amounts of drug(s) (e.g., small molecules) that inhibit the function(s) of IAPs will kill cancer cells or supporting cells outright (those cells whose continued survival is dependent on the overactivity of IAPs) and/or render such cells as a population more susceptible to the cell death-inducing activity of cancer therapeutic drugs or radiation therapies. The present invention contemplates that inhibitors of IAPs satisfy an unmet need for the treatment of multiple cancer types, either when administered as monotherapy to induce apoptosis in cancer cells dependent on IAP function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds lower the apoptotic threshold of all cells that express IAPs, the proportion of cells that successfully execute the apoptosis program in response to the apoptosis inducing activity of anticancer drugs/radiation is increased. Alternatively, the compounds of the present invention can be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the present compounds. Also, since the compounds of the present invention act at least in part by inhibiting IAPs, the exposure of cancer cells and supporting cells to therapeutically effective amounts of the compounds can be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

The present invention relates to Smac mimetics that are useful for inhibiting the activity of IAP proteins and increasing the sensitivity of cells to inducers of apoptosis. In one particular embodiment, the Smac mimetics are compounds of formula I:

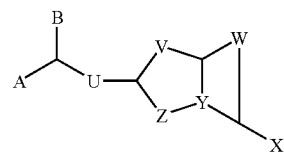

or a pharmaceutically acceptable salt or prodrug thereof, wherein:

A is $NR_1R_2$, or $N^+R_1R_2R_3$;

$R_1$, $R_2$, and $R_3$ are independently hydrogen or optionally substituted $C_{1-8}$ alkyl, $C_{2-8}$ alkenyl, or $C_{2-8}$ alkynyl, in which one or more carbons can be replaced by C=O, C=S, or a heteroatom selected from O, S, and N, and one or more hydrogens in CH, $CH_2$ or $CH_3$ groups can be replaced by fluorine, a branched or unbranched alkyl or cycloalkyl, an optionally substituted aryl, alkylaryl, heteroaryl, or alkylheteroaryl, or $OR_4$, $SR_4$, or $NR_4R_5$; $R_4$, and $R_5$ are independently hydrogen or optionally substituted $C_{1-4}$ alkyl, $C_{2-5}$ alkenyl, or $C_{2-5}$ alkynyl, in which one or more carbons can be replaced by a heteroatom selected from O, S, and N, or optionally substituted aryl, alkylaryl, heteroaryl, or alkylheteroaryl; or any two of $R_1$, $R_2$, and $R_3$ taken together with the nitrogen to which they are attached form a heterocyclic group, in which one or more carbon atom can be replaced by C=O, C=S, or a heteroatom selected from O, S, and N, with the proviso that the heteroatom is separated from the nitrogen atom by at least two carbons;

B is optionally substituted $C_{1-4}$ alkyl, $C_{2-4}$ alkenyl, or $C_{2-4}$ alkynyl, wherein one or more hydrogens can be replaced by fluorine;

U is CONH, C(O)O, C(S)O, C(S)NH, C(NH)NH, or $(CH_2)_{1-5}$, wherein one or more carbons can be replaced by a heteroatom selected from O, S, and N;

V and W are independently $(CH_2)_{1-5}$, wherein one or more carbons can be replaced by C=O, C=S, or a heteroatom selected from O, S, and N, and one or more hydrogens in $CH_2$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;

X is optionally substituted $C_{1-18}$ alkyl, $C_{2-18}$ alkenyl, $C_{2-18}$ alkynyl, aryl, or heteroaryl, wherein one or more carbons can be replaced by C=O, C=S, or a heteroatom selected from O, S, and N, and one or more hydrogens in CH, $CH_2$ or $CH_3$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;

Y is CH or N;

Z is $CH_2$, C=O, C=S, CHSR, CHOR, or CHNR; and

R is hydrogen or optionally substituted $C_{1-4}$ alkyl, $C_{2-4}$ alkenyl, or $C_{2-4}$ alkynyl.

The invention relates to compounds represented by Formula I, which are inhibitors of IAP proteins. The invention relates to the use if the compounds of the invention to induce apoptosis in cells. The invention also relates to the use of the compounds of the invention for sensitizing cells to inducers of apoptosis. The compounds are useful for the treatment, amelioration, or prevention of disorders responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those which are chemoresistant, radiation resistant, hormone resistant, and the like). In other embodiments, the compounds can be used to treat hyperproliferative diseases characterized by overexpression of IAPs.

The present invention provides pharmaceutical compositions comprising a compound of Formula I in a therapeutically effective amount to induce apoptosis in cells or to sensitize cells to inducers of apoptosis.

The invention further provides kits comprising a compound of Formula I and instructions for administering the compound to an animal. The kits may optionally contain other therapeutic agents, e.g., anticancer agents, apoptosis modulating agents.

The invention also provides methods of making compounds of Formula I.

BRIEF DESCRIPTION OF THE DRAWINGS/FIGURES

DETAILED DESCRIPTION OF THE INVENTION

Figure 1:
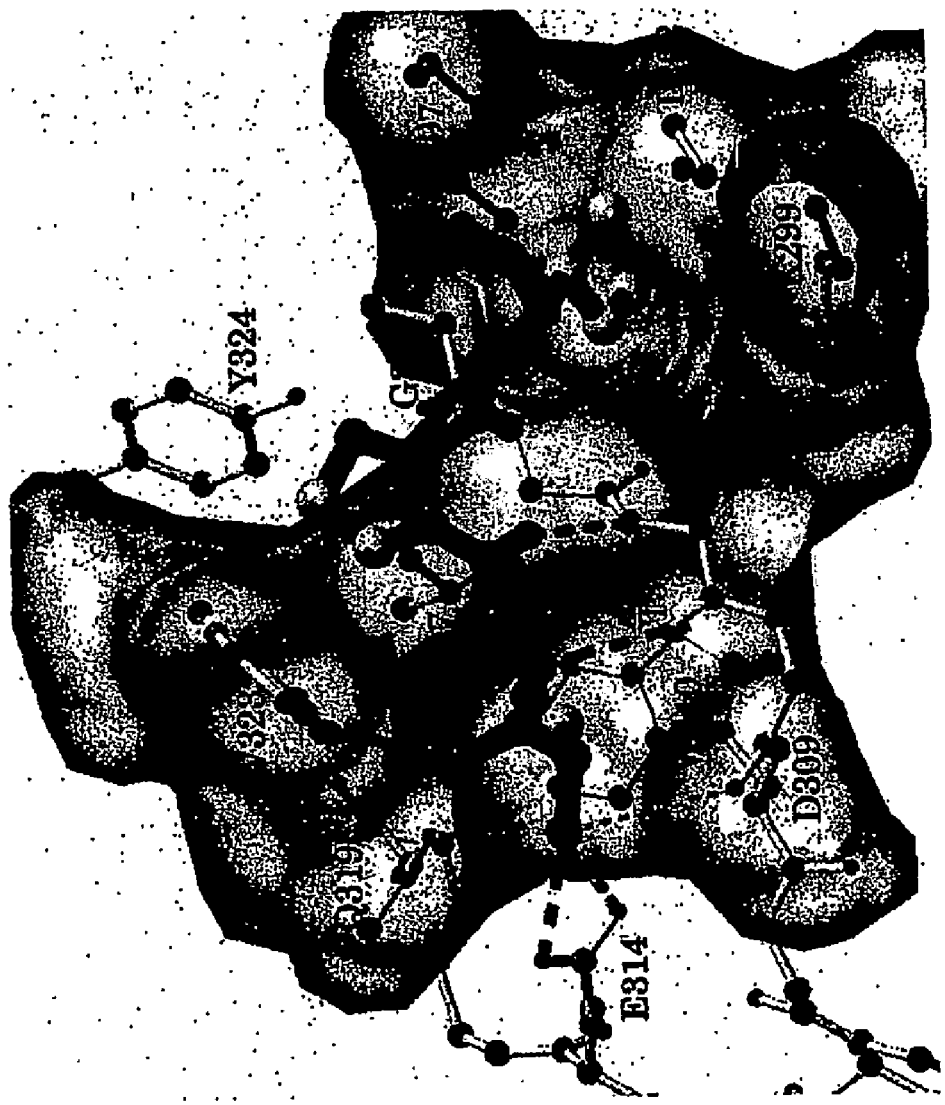
FIG. 1 shows the modeled complex of Smac peptide with XIAP BIR3.

The present invention relates to conformationally constrained compounds represented by Formula I, which are mimetics of Smac and function as inhibitors of IAPs. By inhibiting IAPs, these compounds sensitize cells to inducers of apoptosis and, in some instances, themselves induce apoptosis. Therefore, the invention relates to methods of sensitizing cells to inducers of apoptosis and to methods of inducing apoptosis in cells, comprising contacting the cells with a compound of Formula I alone or in combination with an inducer of apoptosis. The invention further relates to methods of treating, ameliorating, or preventing disorders in an animal that are responsive to induction of apoptosis comprising administering to the animal a compound of Formula I and an inducer of apoptosis. Such disorders include those characterized by a dysregulation of apoptosis and those characterized by overexpression of IAPs.

The term "IAP proteins," as used herein, refers to any known member of the Inhibitor of Apoptosis Protein family, including, but not limited to, XIAP, cIAP-1, cIAP-2, and ML-IAP.

The term "overexpression of IAPs," as used herein, refers to an elevated level (e.g., aberrant level) of mRNAs encoding for an IAP protein(s), and/or to elevated levels of IAP protein (s) in cells as compared to similar corresponding non-pathological cells expressing basal levels of mRNAs encoding IAP proteins or having basal levels of IAP proteins. Methods for detecting the levels of mRNAs encoding LAP proteins or levels of IAP proteins in a cell include, but are not limited to, Western blotting using IAP protein antibodies, immunohistochemical methods, and methods of nucleic acid amplification or direct RNA detection. As important as the absolute level of IAP proteins in cells is to determining that they overexpress IAP proteins, so also is the relative level of LAP proteins to other pro-apoptotic signaling molecules (e.g., pro-apoptotic Bcl-2 family proteins) within such cells. When the balance of these two are such that, were it not for the levels of the IAP proteins, the pro-apoptotic signaling molecules would be sufficient to cause the cells to execute the apoptosis program and die, said cells would be dependent on the IAP proteins for their survival. In such cells, exposure to an inhibiting effective amount of an IAP protein inhibitor will be sufficient to cause the cells to execute the apoptosis program and die. Thus, the term "overexpression of an IAP protein" also refers to cells that, due to the relative levels of pro-apoptotic signals and anti-apoptotic signals, undergo apoptosis in response to inhibiting effective amounts of compounds that inhibit the function of IAP proteins.

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g. a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed, in the preparation of salts useful as intermediates in obtaining the compounds of the invention and their pharmaceutically acceptable acid addition salts.

Examples of bases include, but are not limited to, alkali metal (e.g. sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formula I), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis modulating agents," as used herein, refers to agents which are involved in modulating (e.g., inhibiting, decreasing, increasing, promoting) apoptosis. Examples of apoptosis modulating agents include proteins which comprise a death domain such as, but not limited to, Fas/CD95, TRAMP, TNF RI, DR1, DR2, DR3, DR4, DR5, DR6, FADD, and RIP. Other examples of apoptotic modulating agents include, but are not limited to, TNFα, Fas ligand, antibodies to Fas/CD95 and other TNF family receptors, TRAIL, antibodies to TRAILR1 or TRAILR2, Bcl-2, p53, BAX, BAD, Akt, CAD, PI3 kinase, PP1, and caspase proteins. Modulating agents broadly include agonists and antagonists of TNF family receptors and TNF family ligands. Apoptosis modulating agents may be soluble or membrane bound (e.g. ligand or receptor). Preferred apoptosis modulating agents are inducers of apoptosis, such as TNF or a TNF-related ligand, particularly a TRAMP ligand, a Fas/CD95 ligand, a TNFR-1 ligand, or TRAIL The inhibitors of IAPs of the present invention are compounds having the general Formula I:

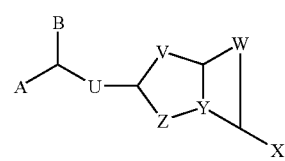

I or a pharmaceutically acceptable salt or prodrug thereof, wherein:

A is $NR_1R_2$, or $N^+R_1R_2R_3$;

$R_1$, $R_2$, and $R_3$ are independently hydrogen or optionally substituted $C_{1-8}$ alkyl, $C_{2-8}$ alkenyl, or $C_{2-8}$ alkynyl, in which one or more carbons can be replaced by C=O, C=S, or a heteroatom selected from O, S, and N, and one or more hydrogens in CH, $CH_2$ or $CH_3$ groups can be replaced by fluorine, a branched or unbranched alkyl or cycloalkyl, an optionally substituted aryl, alkylaryl, heteroaryl, or alkylheteroaryl, or $OR_4$, $SR_4$, or $NR_4R_5$;

$R_4$ and $R_5$ are independently hydrogen or optionally substituted $C_{1-4}$ alkyl, $C_{2-5}$ alkenyl, or $C_{2-5}$ alkynyl, in which one or more carbons can be replaced by a heteroatom selected from O, S, and N, or optionally substituted aryl, alkylaryl, heteroaryl, or alkylheteroaryl; or any two of $R_1$, $R_2$, and $R_3$ taken together with the nitrogen to which they are attached form a heterocyclic group, in which one or more carbon atom can be replaced by C=O, C=S, or a heteroatom selected from O, S, and N, with the proviso that the heteroatom is separated from the nitrogen atom by at least two carbons;

B is optionally substituted $C_{1-4}$ alkyl, $C_{2-4}$ alkenyl, or $C_{2-4}$ alkynyl, wherein one or more hydrogens can be replaced by fluorine;

U is CONH, C(O)O, C(S)O, C(S)NH, C(NH)NH, or $(CH_2)_{1-5}$, wherein one or more carbons can be replaced by a heteroatom selected from O, S, and N;

V and W are independently $(CH_2)_{1-5}$, wherein one or more carbons can be replaced by C=O, C=S, or a heteroatom selected from O, S, and N, and one or more hydrogens in $CH_2$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;

X is optionally substituted $C_{1-18}$ alkyl, $C_{2-18}$ alkenyl, $C_{2-18}$ alkynyl, aryl, or heteroaryl, wherein one or more carbons can be replaced by C=O, C=S, or a heteroatom selected from O, S, and N, and one or more hydrogens in CH, $CH_2$ or $CH_3$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;

Y is CH or N;

Z is $CH_2$, C=O, C=S, CHSR, CHOR, or CHNR; and

R is hydrogen or optionally substituted $C_{1-4}$ alkyl, $C_{2-4}$ alkenyl, or $C_{2-4}$ alkynyl.

Useful alkyl groups include straight-chained or branched $C_{1-18}$ alkyl groups, especially methyl, ethyl, propyl, isopropyl, t-butyl, sec-butyl, 3-pentyl, adamantyl, norbornyl, and 3-hexyl groups.

Useful alkenyl groups include straight-chained or branched $C_{2-18}$ alkyl groups, especially ethenyl, propenyl, isopropenyl, butenyl, isobutenyl, and hexenyl.

Useful alkynyl groups are $C_{2-18}$ alkynyl groups, especially ethynyl, propynyl, butynyl, and 2-butynyl groups Useful cycloalkyl groups are $C_{3-8}$ cycloalkyl. Typical cycloalkyl groups include cyclopropyl, cyclobutyl, cyclopentyl, cyclohexyl and cycloheptyl.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Optional substituents include one or more alkyl; halo; haloalkyl; cycloalkyl; aryl optionally substituted with one or more lower alkyl, halo, haloalkyl or heteroaryl groups; aryloxy optionally substituted with one or more lower alkyl, haloalkyl, or heteroaryl groups; aralkyl, heteroaryl optionally substituted with one or more lower alkyl, haloalkyl, and aryl groups; heteroaryloxy optionally substituted with one or more lower alkyl, haloalkyl, and aryl groups; alkoxy; alkylthio; arylthio; amido; amino; acyloxy; arylacyloxy optionally substituted with one or more lower alkyl, haloalkyl, and aryl groups; diphenylphosphinyloxy optionally substituted with one or more lower alkyl, halo or haloalkyl groups; heterocyclo optionally substituted with one or more lower alkyl, haloalkyl, and aryl groups; heterocycloalkoxy optionally substituted with one or more lower alkyl, haloalkyl, and aryl groups; partially unsaturated heterocycloalkyl optionally substituted with one or more lower alkyl, haloalkyl, and aryl groups; or partially unsaturated heterocycloalkyloxy optionally substituted with one or more lower alkyl, haloalkyl, and aryl groups.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkylaryl and alkylheteroaryl groups include any of the above-mentioned $C_{1-18}$ alkyl groups substituted by any of the above-mentioned $C_{6-14}$ aryl groups or heteroaryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above. Also included are the sulfoxides and sulfones of such alkylthio groups.

Useful amido groups include carbonylamido as well as any $C_{1-10}$ acyl (alkanoyl) attached to an amino nitrogen, e.g., acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

Certain of the compounds of the present invention may exist as stereoisomers including optical isomers. The invention includes all stereoisomers and both the racemic mixtures of such stereoisomers as well as the individual enantiomers that may be separated according to methods that are well known to those of skill in the art.

In one embodiment, the compounds of the present invention have the stereochemistry of formula II, wherein the variables are as defined above.

II
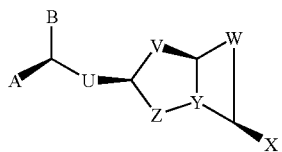
Another embodiment of the invention is compounds having formula III, wherein the variables are as defined above.
III
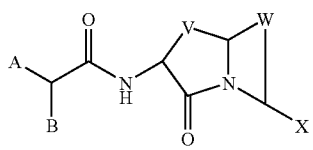
In one embodiment, the compounds of the present invention have the stereochemistry of formula IV, wherein the variables are as defined above.
IV
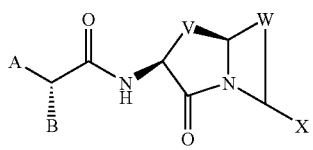
In certain embodiments of the invention the compound of Formula I comprises:
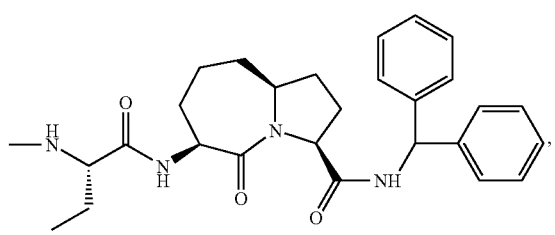
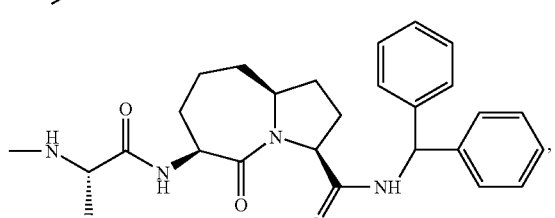
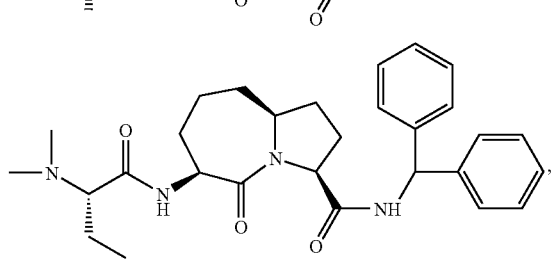
-continued
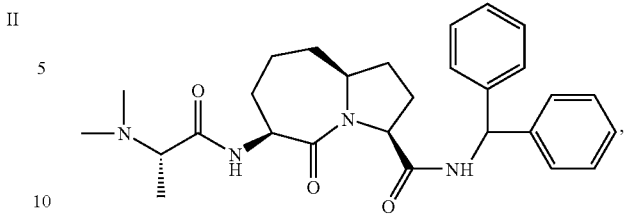
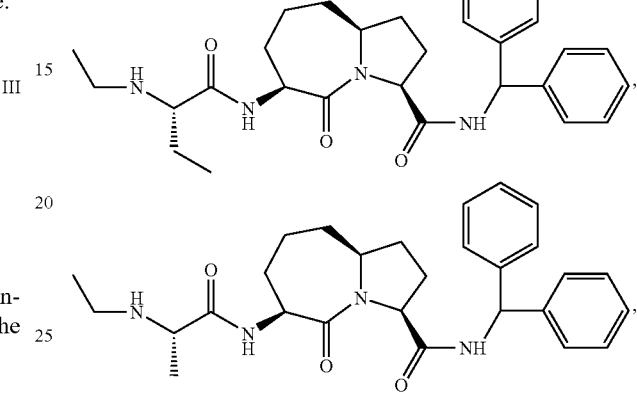
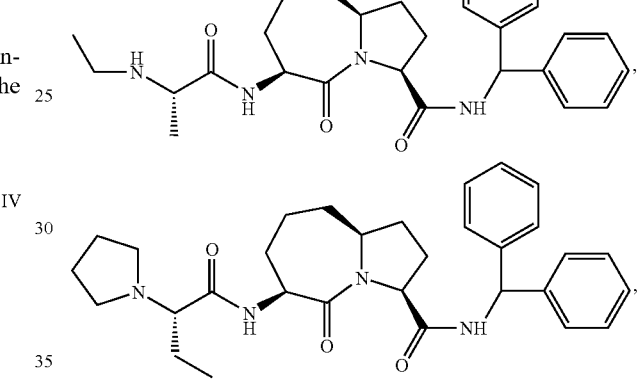
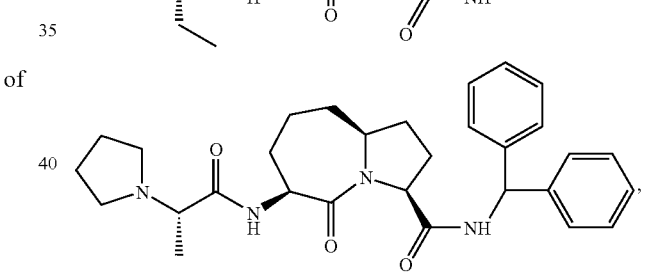
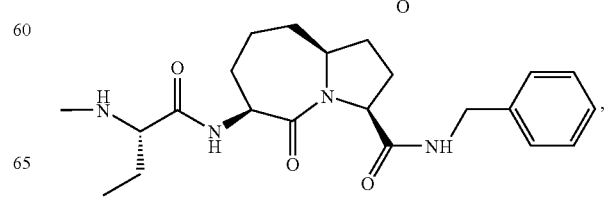

-continued
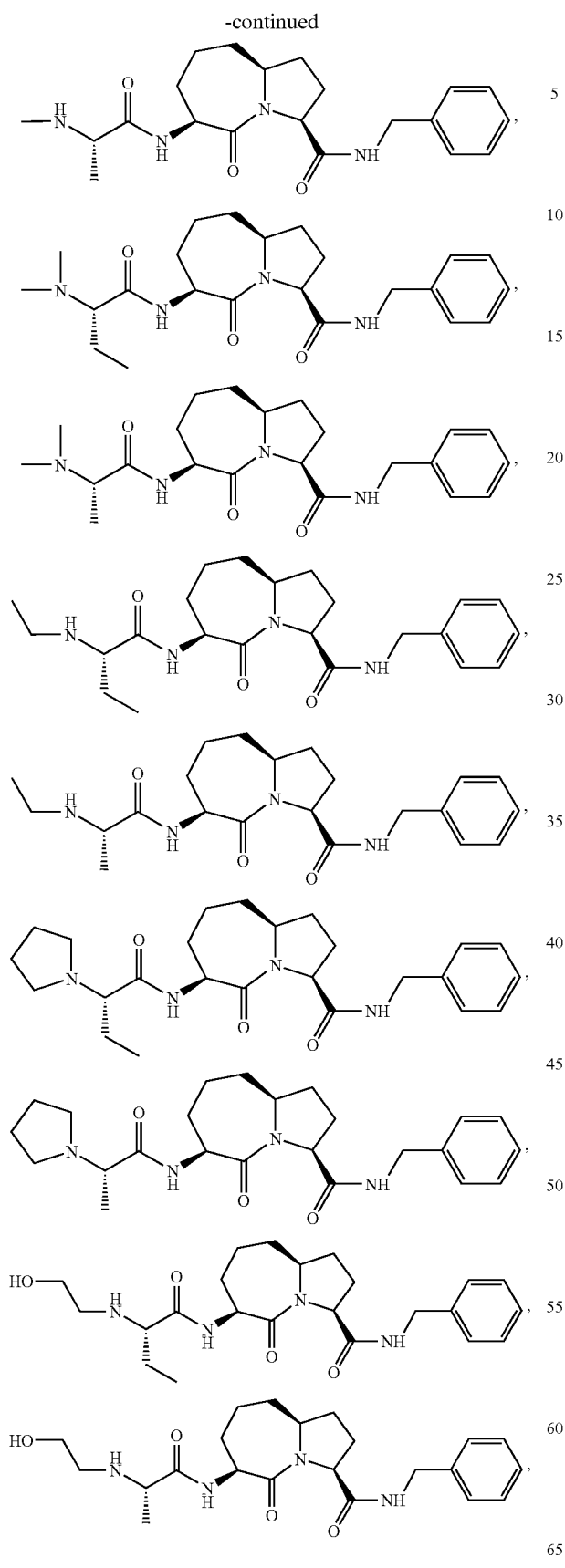
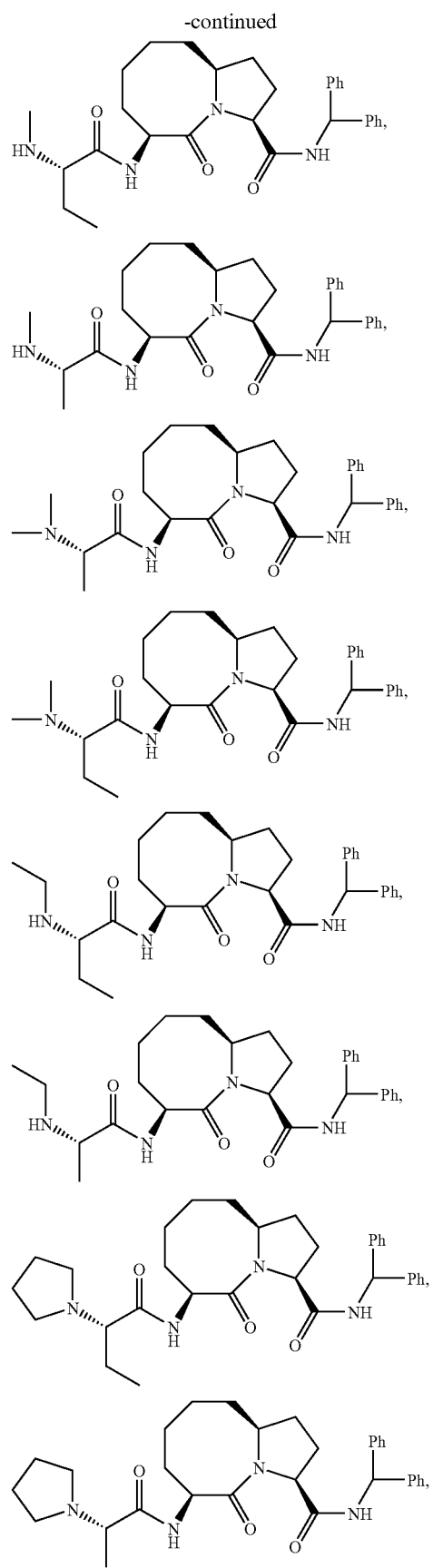

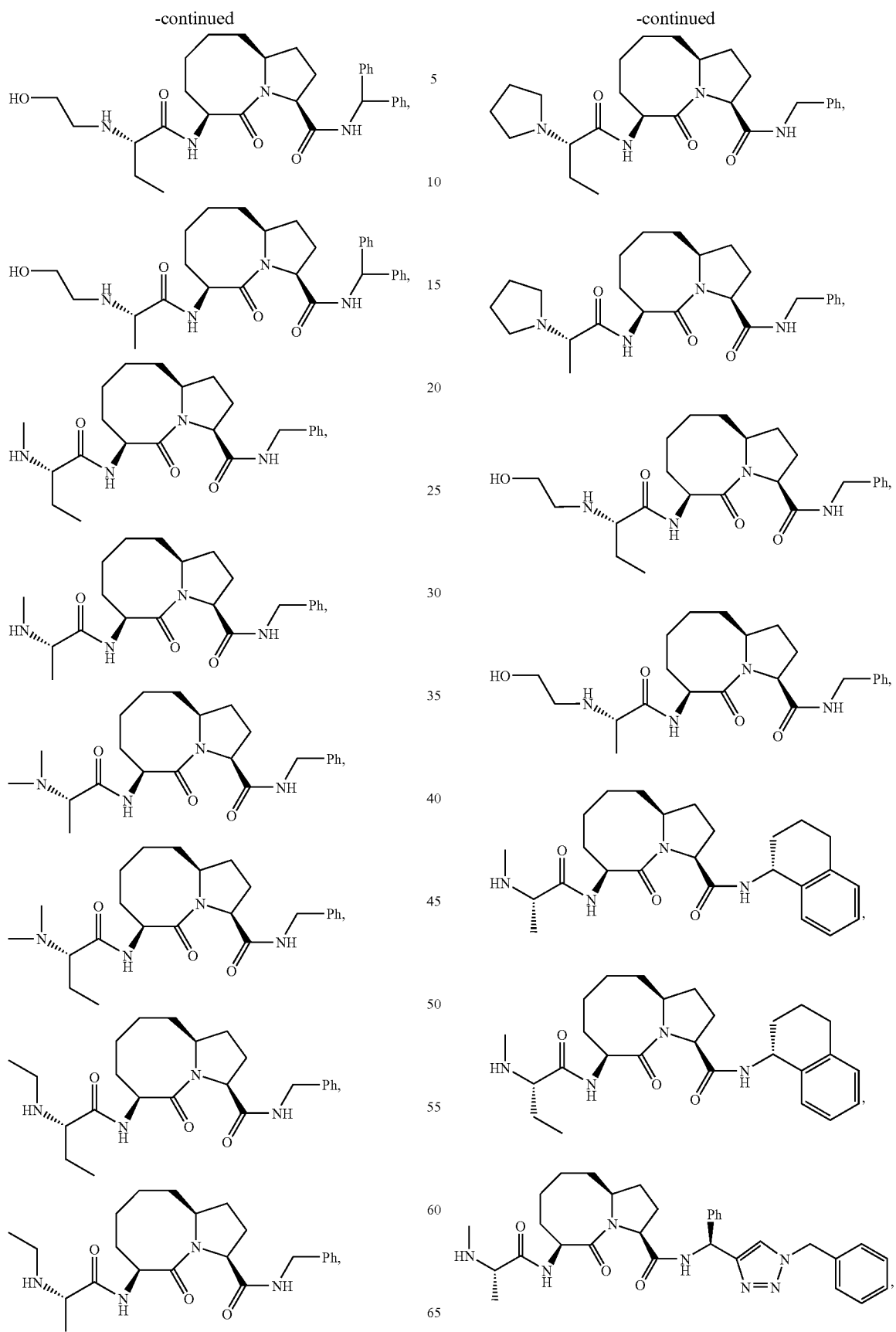

-continued

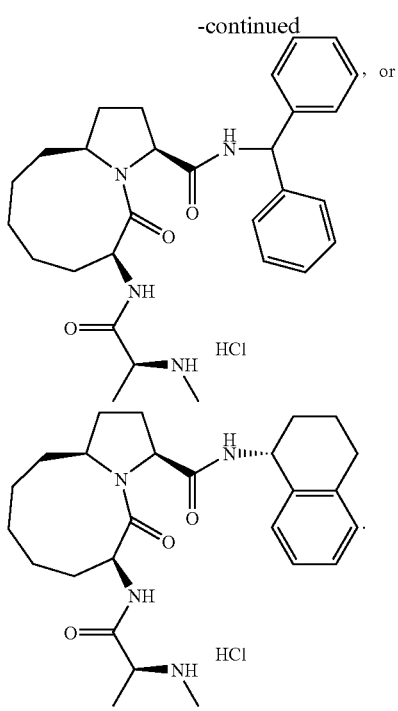

The compounds of this invention may be prepared using methods known to those of skill in the art. Specifically, compounds with Formula I can be prepared as illustrated by the exemplary reactions in the Examples.

An important aspect of the present invention is that compounds of Formula I induce apoptosis and also potentiate the induction of apoptosis in response to apoptosis induction signals. Therefore, it is contemplated that these compounds sensitize cells to inducers of apoptosis, including cells that are resistant to such inducers. The IAP inhibitors of the present invention can be used to induce apoptosis in any disorder that can be treated, ameliorated, or prevented by the induction of apoptosis. Thus, the present invention provides compositions and methods for targeting animals characterized as overexpressing an IAP protein. In some of the embodiments, the cells (e.g., cancer cells) show elevated expression levels of IAP proteins as compared to non-pathological samples (e.g., non-cancerous cells). In other embodiments, the cells operationally manifest elevated expression levels of IAP proteins by virtue of executing the apoptosis program and dying in response to an inhibiting effective amount of a compound of Formula I, said response occurring, at least in part, due to the dependence in such cells on IAP protein function for their survival.

In another embodiment, the invention pertains to modulating an apoptosis associated state which is associated with one or more apoptosis modulating agents. Examples of apoptosis modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAILR1 or TRAILR2, Bcl-2, p53, BAX, BAD, Akt, CAD, PI3 kinase, PP1, and caspase proteins. Other agents involved in the initiation, decision and degradation phase of apoptosis are also included. Examples of apoptosis modulating agents include agents, the activity, presence, or change in concentration of which, can modulate apoptosis in a subject. Preferred apoptosis modulating agents are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formula I and at least one additional therapeutic agent (including, but not limited to, chemotherapeutic antineoplastics, apoptosis modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins); toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDLAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formula I and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g. cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g. tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |

TABLE 1-continued

| | | |
|---|---|---|
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo- | Adriamycin, Rubex | Pharmacia & Upjohn Company |

TABLE 1-continued

| | | |
|---|---|---|
| hexopyranosyl)oxy]-8-glycolyl-7,8,9,10-tetrahydro-6,8,11-trihydroxy-1-methoxy-5,12-naphthacenedione hydrochloride) | | |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-,3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside],4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) [2'-deoxy-5-fluorouridine] | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)L-lyxo-hexopyranosyl)oxy]-7,8,9,10-tetrahydro-6,9,11-trihydroxyhydrochloride, (7S-cis)) | Idamycin | Pharmacia & Upjohn Company |

TABLE 1-continued

| | | |
|---|---|---|
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo 2,1-b] thiazole monohydrochloride $C_{11}H_{12}N_2S \cdot HCl$ | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl)amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a,4,7β,10β,13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1- | Aredia | Novartis |

TABLE 1-continued

| | | |
|---|---|---|
| hydroxypropylidene) bis-, disodium salt, pentahydrate, (APD)) | | |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl)phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino 1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |

TABLE 1-continued

| | | |
|---|---|---|
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Preferred conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, and bevacizumab. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formula I with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g. using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (udR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formula I and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 10 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 1000 mg, preferably about 0.1 to about 100 mg of the compound. The unit dose may be administered one or more times daily as one or more tablets or capsules each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

Development of Fluorescence Polarization Assay

A quantitative in vitro binding assay using fluorescence polarization was developed. Binding of Smac to XIAP is mediated by a few amino acid residues at the N-terminus of Smac (FIG. 1). Two different fluorescent probes were synthesized: the natural 9-mer Smac peptide (AVPIAQKSEK (SEQ ID NO:3)) and a mutated 5-mer Smac peptide (AbuRPFK, wherein Abu=2-aminobutyric acid (SEQ ID NO:4)). Each probe was labeled with 6-carboxyfluorescein succinimidyl ester (FAM) as the fluorescent tag (AVPIAQKSEK-FAM, termed S9F and AbuRPFK-FAM, termed SM5F, respectively). The unlabeled 9-mer and 5-mer Smac peptides (S9 and SM5) were used as the positive controls. The human XIAP-BIR3 protein (residues 241-356) with a His tag is stable and soluble and was used for the binding assay.

Figure 2:
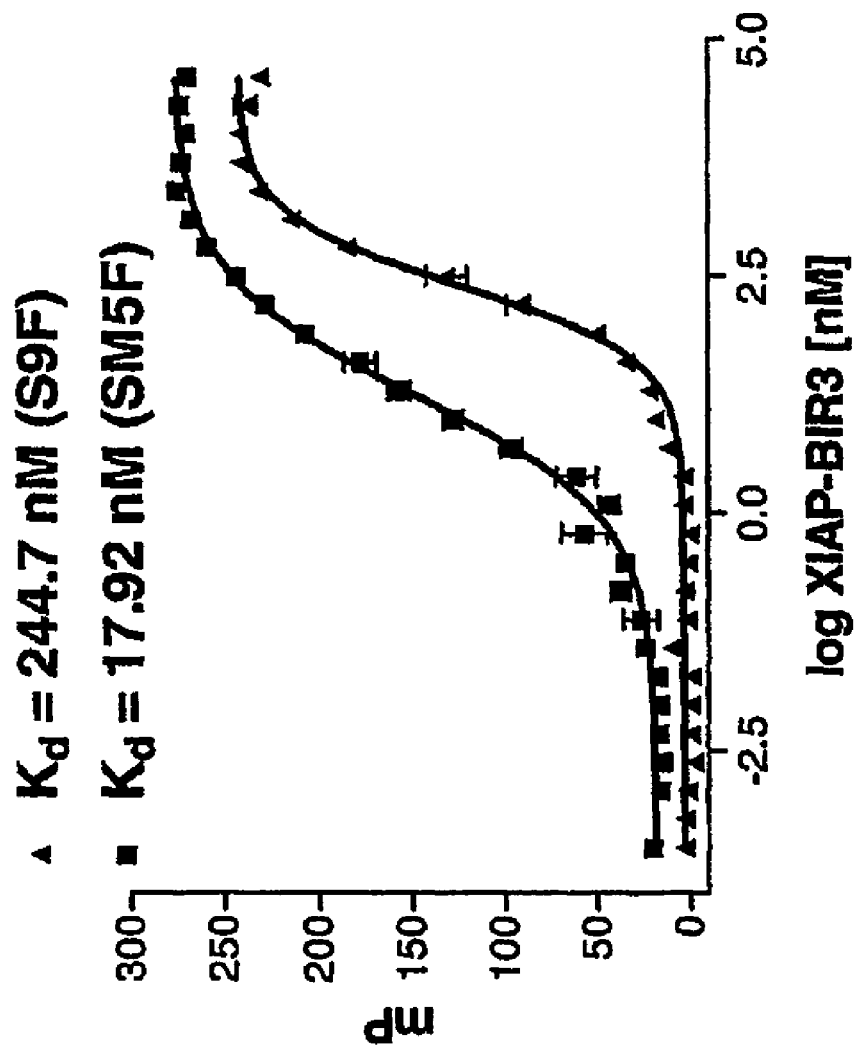
FIG. 2 shows the saturation binding curves for the FP-based assay.

The dissociation constant value of the fluorescent labeled S9F and SM5F to XIAP-BIR3 was first determined using a constant concentration of the peptide (5 nM) and titrating with increasing concentrations of the protein (0 to 40 µM), significantly above the expected $K_d$. FIG. 2 shows the non-linear least-squares fit to a single-site binding model for the saturation experiments. It was determined that S9F has a $K_d$ value of 0.24 µM with a maximum binding range of 236 mP±1.21 mP. The SM5F probe had a $K_d$ value of 0.018 µM (17.92 nM) and a larger dynamic range with maximum binding of 276 mP±0.75 mP. The assay was stable over a 24 hour period, the $K_d$ values and binding ranges remained unchanged and 4% DMSO had no influence.

Because SM5F had a higher binding affinity (about 10 times higher) and a larger dynamic range than the natural Smac peptide S9F, this labeled peptide was selected for the competitive binding assay. The assay conditions used were 5 nM SM5F and 0.030 µM XIAP-BIR3 protein based on the following considerations: 0.030 µM XIAP is about 2 times higher than the $K_d$ of SM5F; and 5 nM SM5F has sufficient fluorescence intensity to overcome the fluorescence background in case some of the inhibitors have a certain level of fluorescence. Under these conditions, the tracer is saturated about 60%, making the assay sensitive. The mP range (mP of bound peptide-mP of free peptide) is 88±2.43 MP, which is a large polarization signal window for accurate detection of mP change. The Z' factor, a statistical parameter for the quality of the assay, is 0.88, which confirms that the fluorescence polarization assay based on the SM5F probe is adequate for high-throughput screening.

Figure 3:
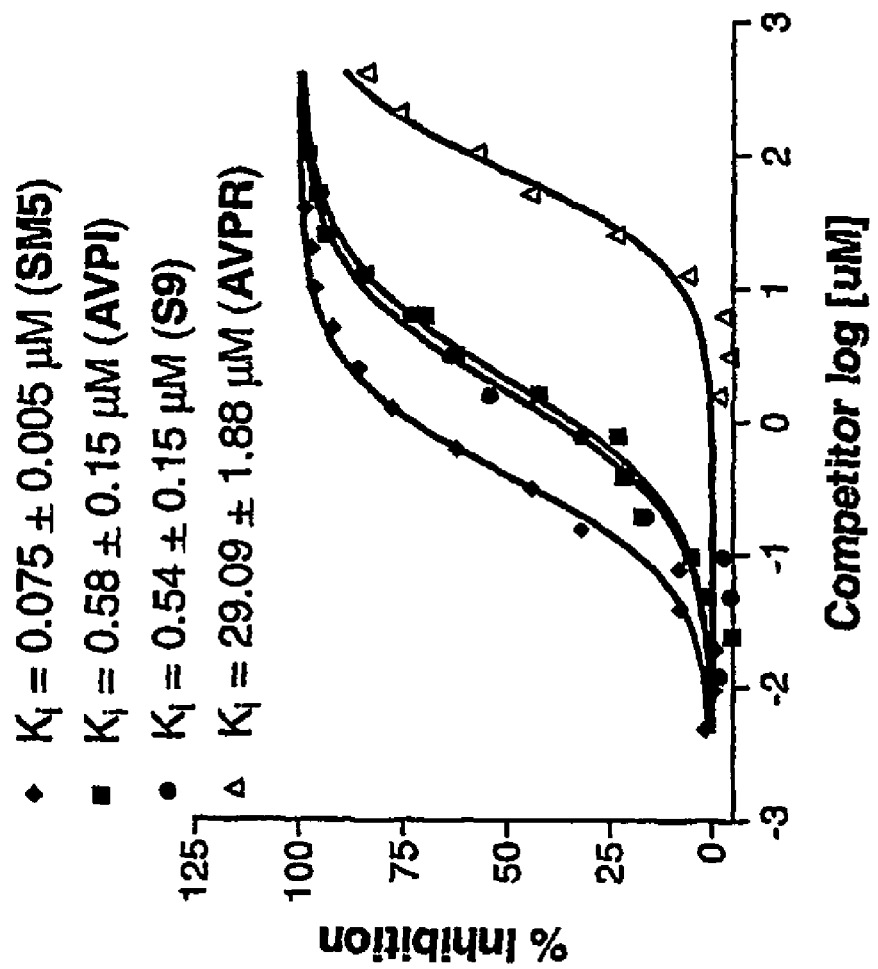
FIG. 3 shows the binding of peptides in the FP-based assay.

The specificity of the assay was verified in a competition experiment with corresponding unlabeled mutated Smac 5-mer (SM5) and the natural Smac 9-mer (S9) peptides (FIG. 3). In both cases, the data indicated that unlabeled peptides were able to abrogate binding of the labeled tracer. $IC_{50}$ values of 1.49±0.21 µM ($K_i$=0.54±0.15 µM) for S9 and 0.22±0.01 µM ($K_i$=0.075±0.005 µM for SM5 were obtained. The obtained $IC_{50}$ values are higher than the $K_d$ values of the protein/peptide pair, because in order to maximize the signal-to-noise ratio, the protein concentration in the competitive FP binding assay is higher than the determined $K_d$. However, the ratio of the $IC_{50}$ values of these two unlabeled peptides correlates well with the ratio of the $K_d$ values of their corresponding labeled peptides. The ratio of the $IC_{50}$ values for the unlabeled SM5 and S9 peptides is 6.7 fold, while the ratio of the $K_d$ values between labeled SM5F and S9F is 7.2 fold. For this reason, for the designed Smac mimetics, the $IC_{50}$ values are reported with the $IC_{50}$ value of the natural Smac peptide (S9) and the mutated Smac peptide (SM5) under the same conditions together with the $K_d$ values of labeled SM5F and S9F for proper comparison of their binding affinities. Additionally, a new mathematical equation for computing binding affinities ($K_i$) of the inhibitors in the FP based binding assay was developed, overcoming the problem of high $IC_{50}$ values. The obtained $K_d$ values of labeled peptides (S9F and SM5F) determined by the direct binding experiment are similar to the $K_i$ values of the unlabeled peptides obtained from the competition assay and calculated with the new equation.

To further evaluate the assay conditions two additional published Smac tetrapeptides with different binding affinity to XIAP BIR3 were tested (FIG. 3) (Kipp et al., *Biochemistry* 41:7344 (2002)). AVPI (SEQ ID NO:1), the natural Smac peptide, had an $IC_{50}$ value of 1.58±0.22 µM ($K_i$=0.58±0.15 µM), which is essentially the same as the natural Smac 9-mer S9. Another peptide, AVPR (SEQ ID NO:5), which was reported to have a much weaker affinity than the AVPI (SEQ ID NO:1) peptide, was determined to have an $IC_{50}$ value of 79.31±8.8 µM ($K_i$=29.09±1.88 X under these assay conditions. The order of the obtained peptide affinities for the XIAP protein in these binding experiments correlates well with the published results (AbuRPFK (SEQ ID NO:4)>AVPI (SEQ ID NO:1)=AVPIAQKSEK (SEQ ID NO:3)>AVPR (SEQ ID NO:5)). The results suggest the FP-based binding assay is suitable for accurate and quantitative determination of the binding affinity of Smac peptides with very different binding affinities.

Example 2

Analysis of the Interaction Between Smac and XIAP BIR3 Based Upon Experimental 3D Structures The high resolution experimental 3D structures of the XIAP BIR3 domain in complex with Smac protein and peptide (FIG. 1) provided a solid structural basis for the design of potent Smac mimetics. The amine group of alanine in position 1 (A1') forms four hydrogen bonds with the side chain of Q319 and E314 and the backbone carbonyl group of D309. The methyl group in alanine binds to a small but well-defined hydrophobic pocket. Our analysis showed that this hydrophobic pocket may accommodate a slightly larger hydrophobic group than methyl. The backbone carbonyl of the alanine residue forms a hydrogen bond with the side chain of W323 but this hydrogen bond is not optimal based upon its geometric parameters.

The amino and carbonyl groups of valine (V2') in Smac form two optimal hydrogen bonds to the backbone carbonyl and amino groups of T308, respectively. Its side chain isopropyl group appears not to have close contacts with residues in XIAP BIR3 and is approximately 4-5 Å away from W323 in XIAP BIR3.

The proline residue in position 3 (P3') plays an important role in controlling the conformation of Smac peptide and is in close contact with the hydrophobic side chain of W323 in XIAP BIR3. Its backbone carbonyl group points toward solvent and does not have specific interactions with the protein.

The hydrophobic side chain of the isoleucine residue at position 4 (I4') binds to a well-defined hydrophobic pocket in XIAP BIR3. The amino group of I4' forms a hydrogen bond with the backbone carbonyl of G306 and the carbonyl group does not have specific interactions with the protein.

Of note, similar interactions were observed in the recently determined high resolution X-ray structure of caspase-9 and XIAP BIR3, in which four residues ATPF (SEQ ID NO:2) in caspase-9 mediate the interactions with XIAP BIR3. These atomic detailed, high resolution experimental structures provide a concrete structural basis for designing Smac mimetics.

Example 3

Design of Conformationally Constrained Non-Peptidic Smac Mimetics

The design and modification of the Smac AVPI peptide led to potent simple Smac peptido-mimetics. However, these Smac mimetics have 2-3 natural amino acids and 1-2 natural peptide bonds. To further reduce the peptide characteristics in these simple Smac mimetics, conformationally constrained non-peptidic Smac mimetics were designed and synthesized based upon the 3D complex structures and data obtained from the simple Smac peptido-mimetics.

Figure 4:
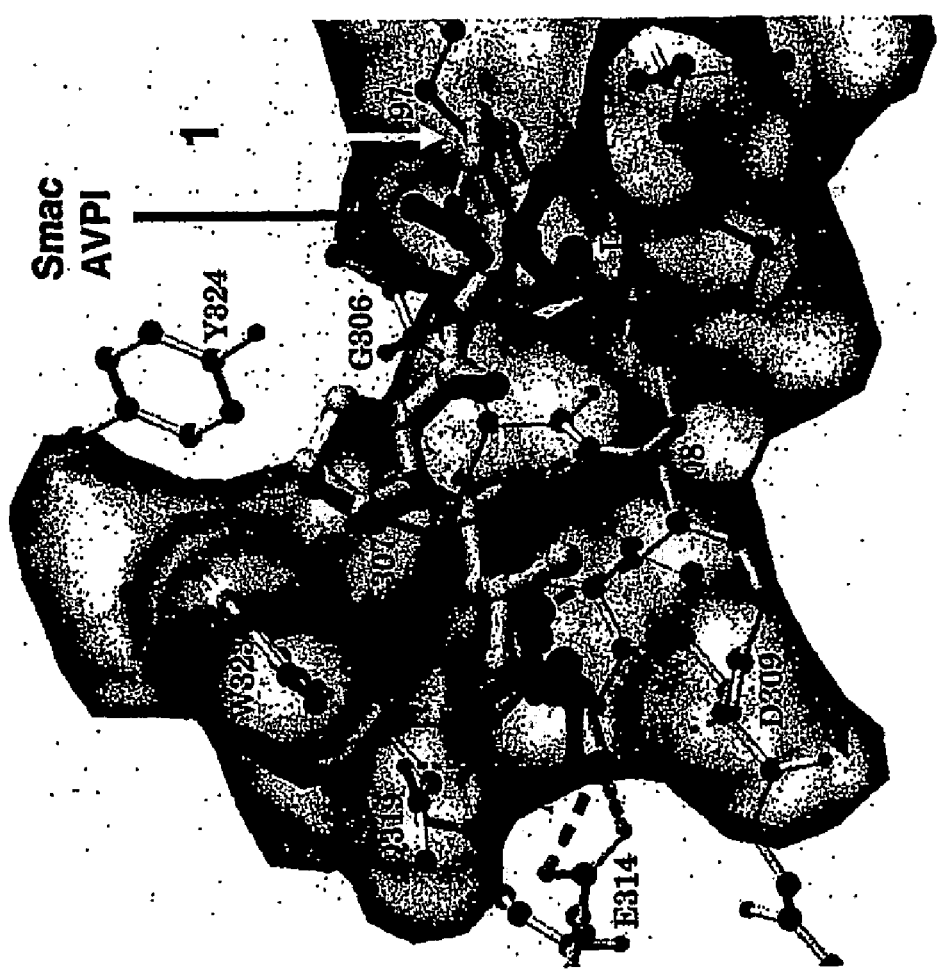
FIG. 4 shows the modeled complex of compound 1 in Table 2 and XIAP BIR3.

The experimental 3D structures of Smac in complex with XIAP BIR3 and our modeled structure for Smac AVPI (SEQ ID NO:1) in which the isoleucine has been replaced with benzylamine (compound 1) (FIGS. 1 and 4) showed that the side chain of valine and proline ring in the Smac AVPI peptide (SEQ ID NO:1) and compound 1 point toward solvent of the binding groove. Therefore it is possible to cyclize these two residues through formation of an additional ring system without causing steric clashes with the protein. Compound 1 (Table 2) was used as a template molecule to test this design strategy. Depending upon the number of carbon atoms in the newly formed ring, different sizes of ring systems can be constructed. Pour sizes of ring systems, namely [3.3.0], [4.3.0], [5.3.0], and [6.3.0] bicyclic lactam systems, were designed.

TABLE 2

| Compound | Structure |
|---|---|
| 1 | (chemical structure) |

TABLE 2-continued

| Compound | Structure |
|---|---|
| 17 | 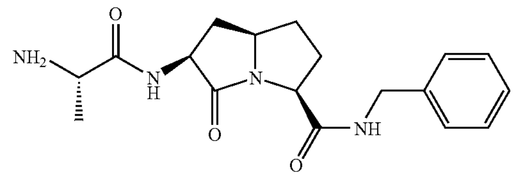 |
| 18 | 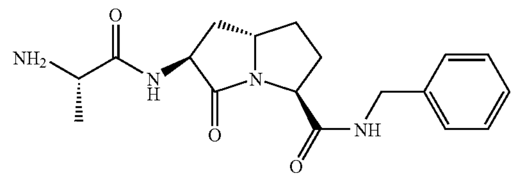 |
| 19 | 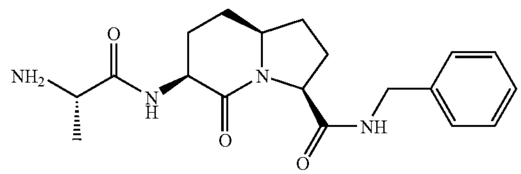 |
| 20 | 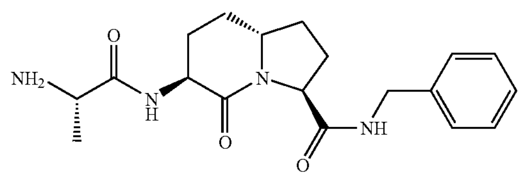 |
| 21 | 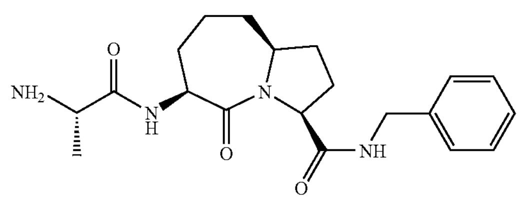 |
| 22 | 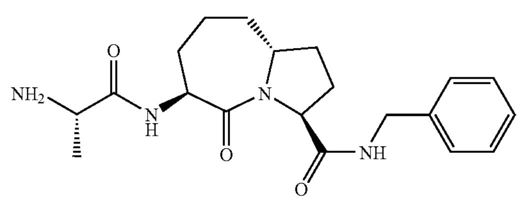 |
| 35 | 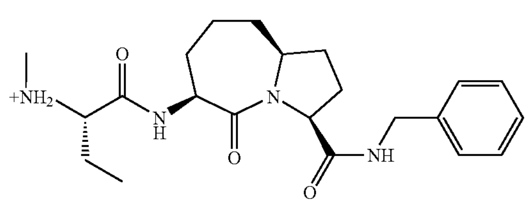 |
| 36 | 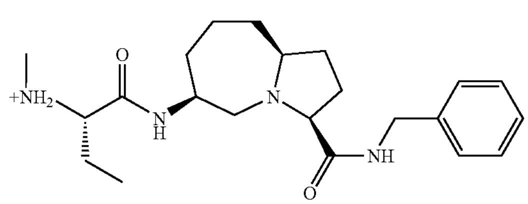 |

TABLE 2-continued

| Compound | Structure |
|---|---|
| 37 | 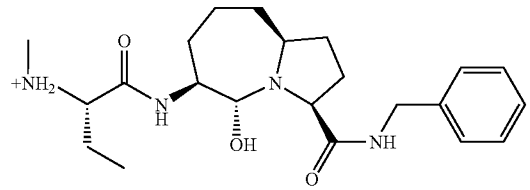 |
| 38 | 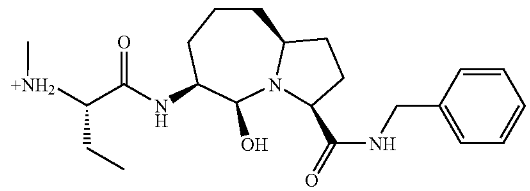 |
| 39 | 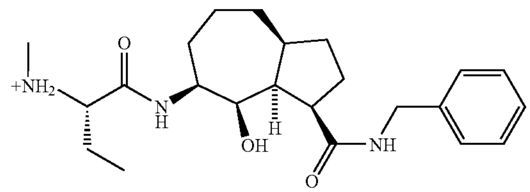 |
| 40 | 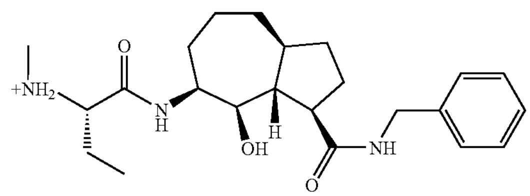 |
| 41 | 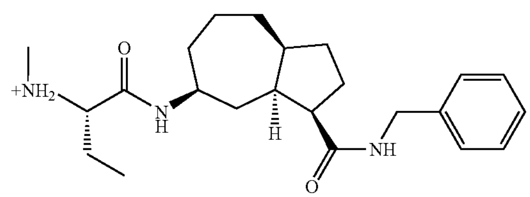 |
| 42 | 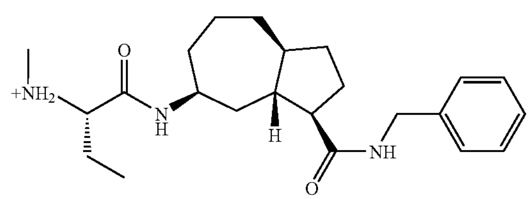 |

Of note, this cyclization strategy allowed the conversion of two natural amino acids (valine and proline) into a non-amino acid, bicyclic, lactam ring system and the resultant Smac mimetics become non-peptide compounds.

For each ring system, there are two stereoisomers due to the generation of the chiral center at the bridging carbon atom. Each stereoisomer was therefore modeled for each ring system. It was found that for compounds 17 and 18 with a [3.3.0] bicyclic lactam system (Table 2), there were significant conformational deviations for those atoms corresponding to the peptide backbone and proline ring in the AVPI (SEQ ID NO:1) bound conformation to XIAP BIR3 and in compound 1. As a result, compounds 17 and 18 cannot form the optimal hydrogen bonds and favorable hydrophobic interactions as observed for the Smac AVPI peptide (SEQ ID NO:1) and compound 1. Accordingly, it was predicted that 17 and 18 with the [3.3.0] bicyclic lactam ring system may only have weak binding to XIAP. The synthesis of these compounds was not pursued.

Figure 5:
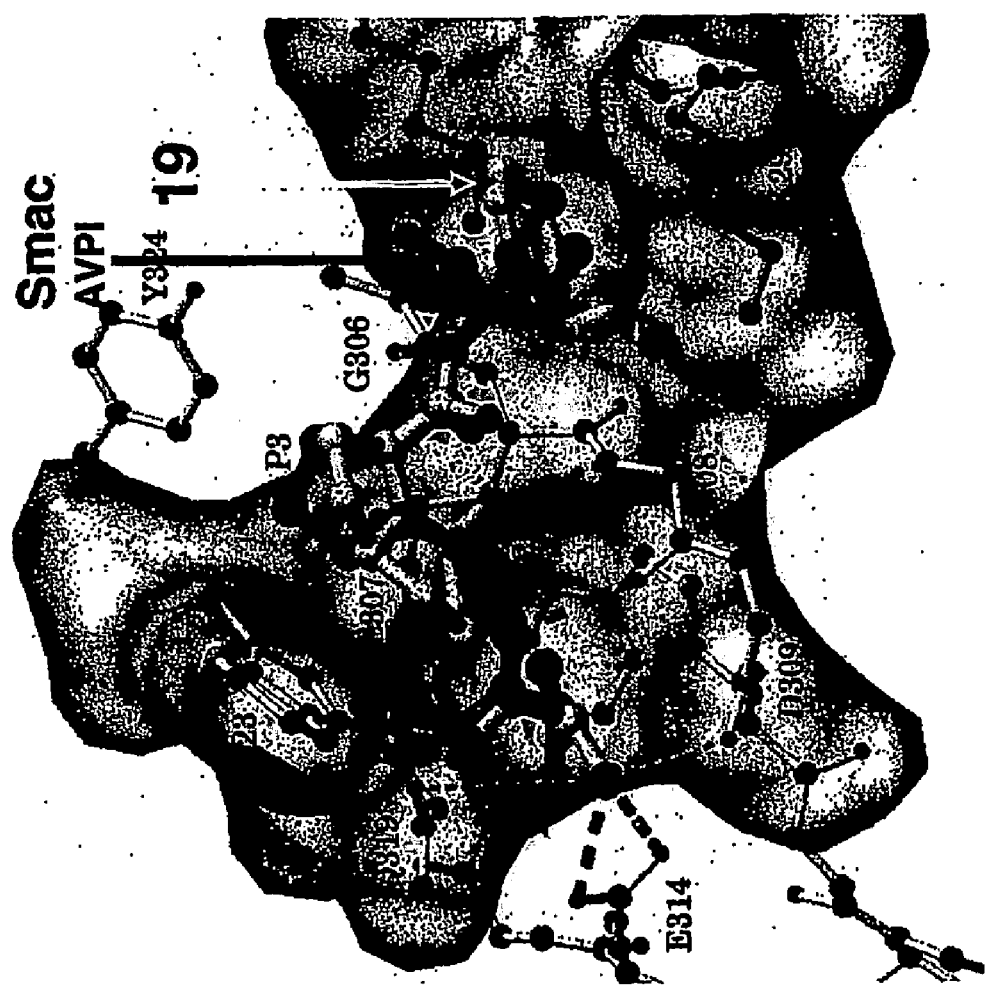
FIG. 5 shows the modeled complex of compound 19 in Table 2 and XIAP BIR3.

Compound 19 with the [4.3.0] bicyclic lactam system (Table 2) quite closely mimics the interactions of Smac AVPI peptide (SEQ ID NO:1)/XIAP BIR3 in the X-ray structure and compound 1/XIAP BIR3 in the modeled structure in both hydrogen bonding and hydrophobic interactions. The modeled complex structure for compound 19, in comparison to the X-ray complex structure of Smac AVPI peptide (SEQ ID NO:1)/XIAP BIR3, is shown in FIG. 5. As can be seen, all the crucial hydrogen bonds found for Smac AVPI (SEQ ID NO:1) in the X-ray structure were formed between compound 19 and XIAP BIR3. The phenyl ring in compound 19 inserts into the hydrophobic pocket, closely mimicking the I4' hydrophobic side chain and the phenyl ring in compound 1. The proline ring in Smac AVPI peptide (SEQ ID NO:1) was found to be in close contact with the side chain of W323 (FIG. 1). The five-membered ring in compound 19, however, bends outwards and has slight deviations as compared to the proline ring in AVPI Smac peptide (SEQ ID NO:1) and compound 1 (FIG. 5). Overall, based upon our modeling results, it was predicted that compound 19 may have a reasonable binding affinity to XIAP BIR3. In contrast, the stereoisomer compound 20 (Table 2) was found to be unable to effectively interact with XIAP BIR3. Although the conformations for the atoms corresponding to the backbone atoms and proline ring in Smac AVPI peptide (SEQ ID NO: 1) are closely maintained in compound 20, the newly formed 6-membered ring has severe van der Waals clashes (responsions) with the W323 residue in XIAP. Accordingly, it was predicted that compound 20 may only have a very weak affinity to XIAP.

Figure 6:
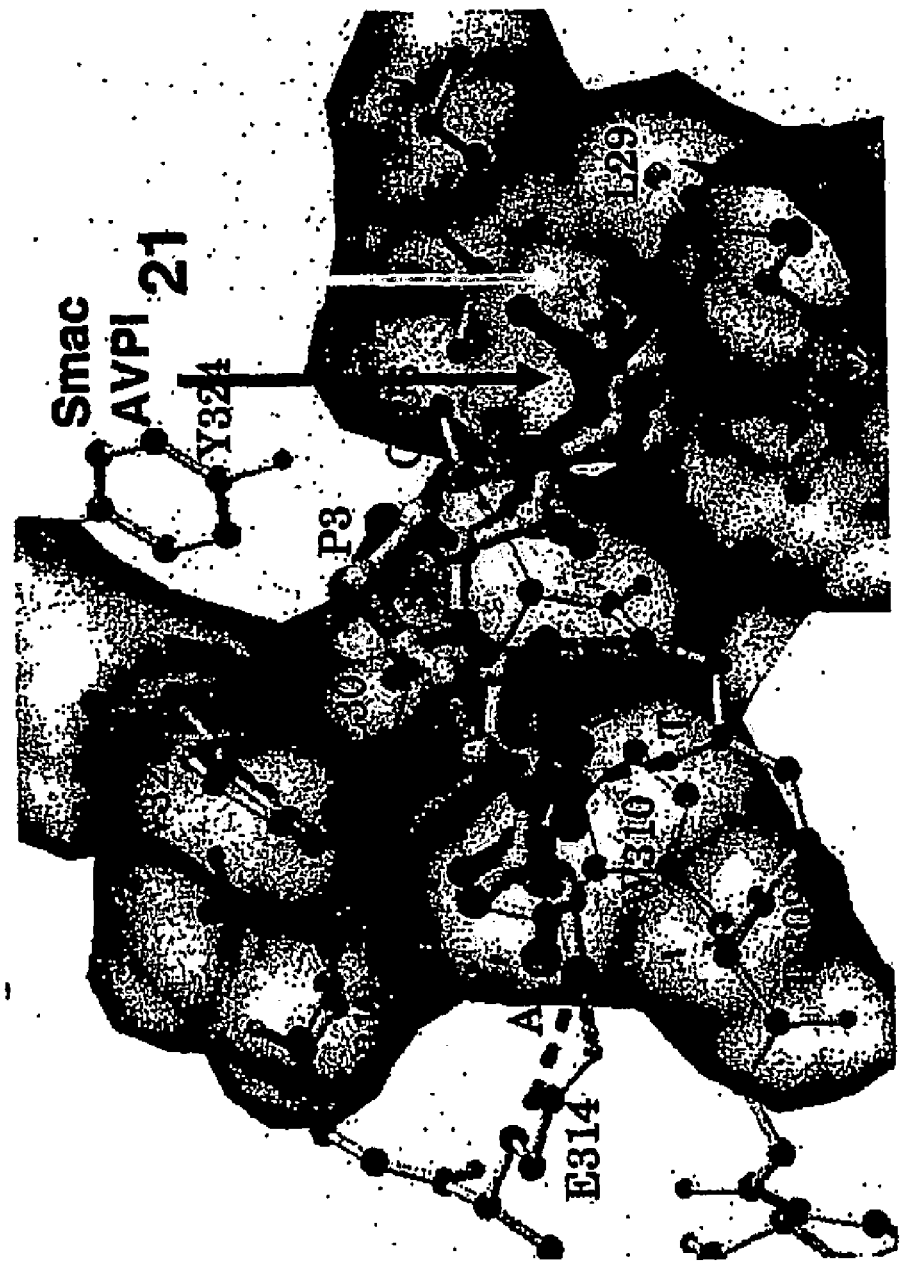
FIG. 6 shows the modeled complex of compound 21 in Table 2 and XIAP BIR3.
Figure 7:
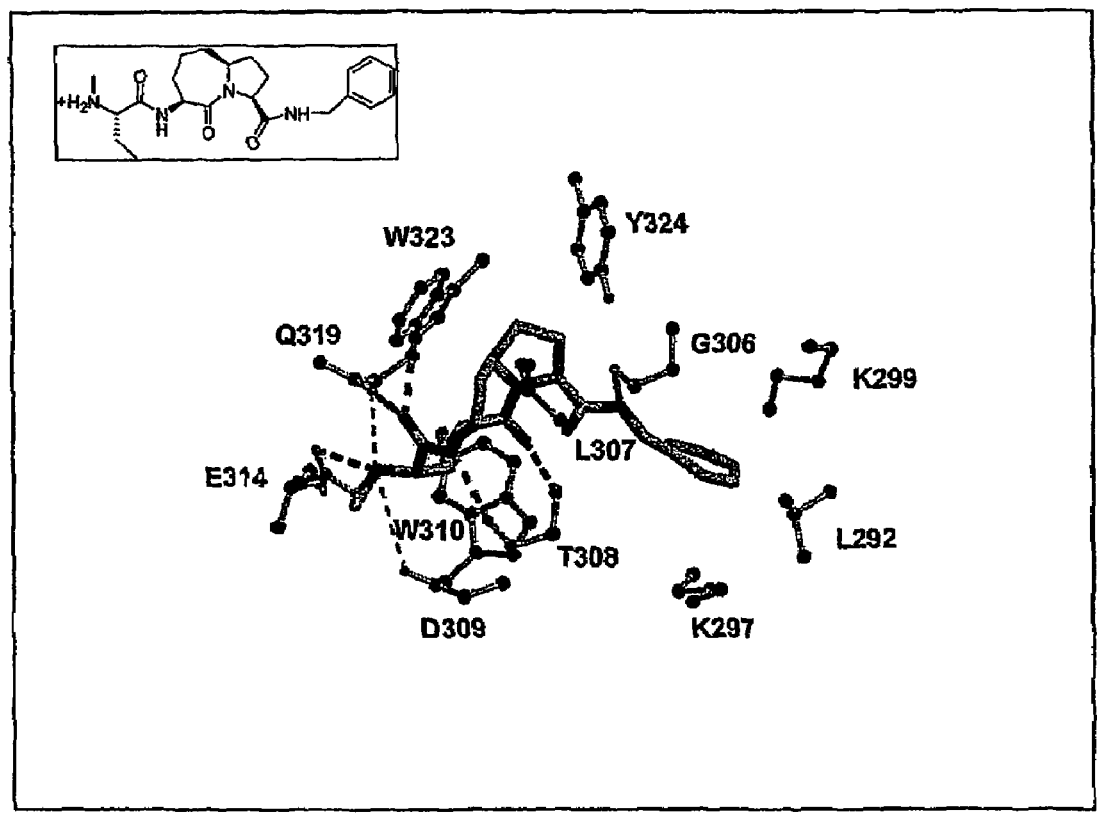
FIG. 7 shows the modeled complex of compound 35 in Table 2 and XIAP BIR3.
Figure 8:
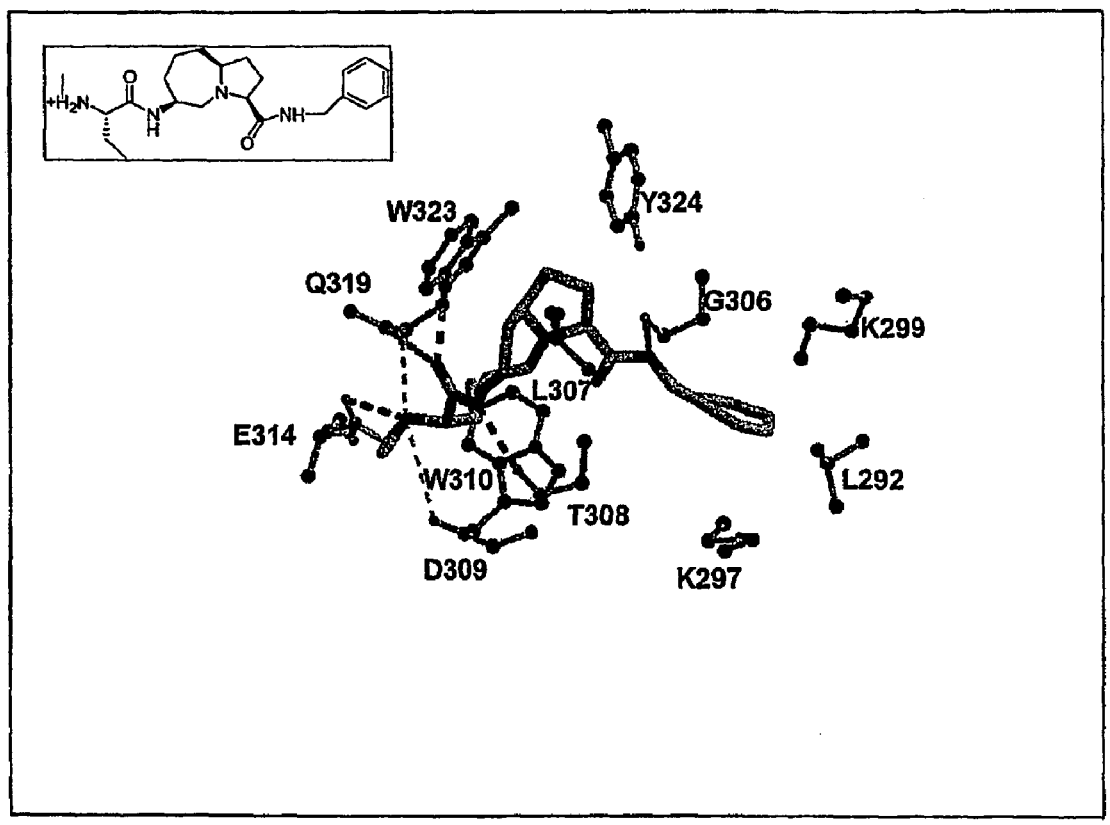
FIG. 8 shows the modeled complex of compound 36 in Table 2 and XIAP BIR3.
Figure 9:
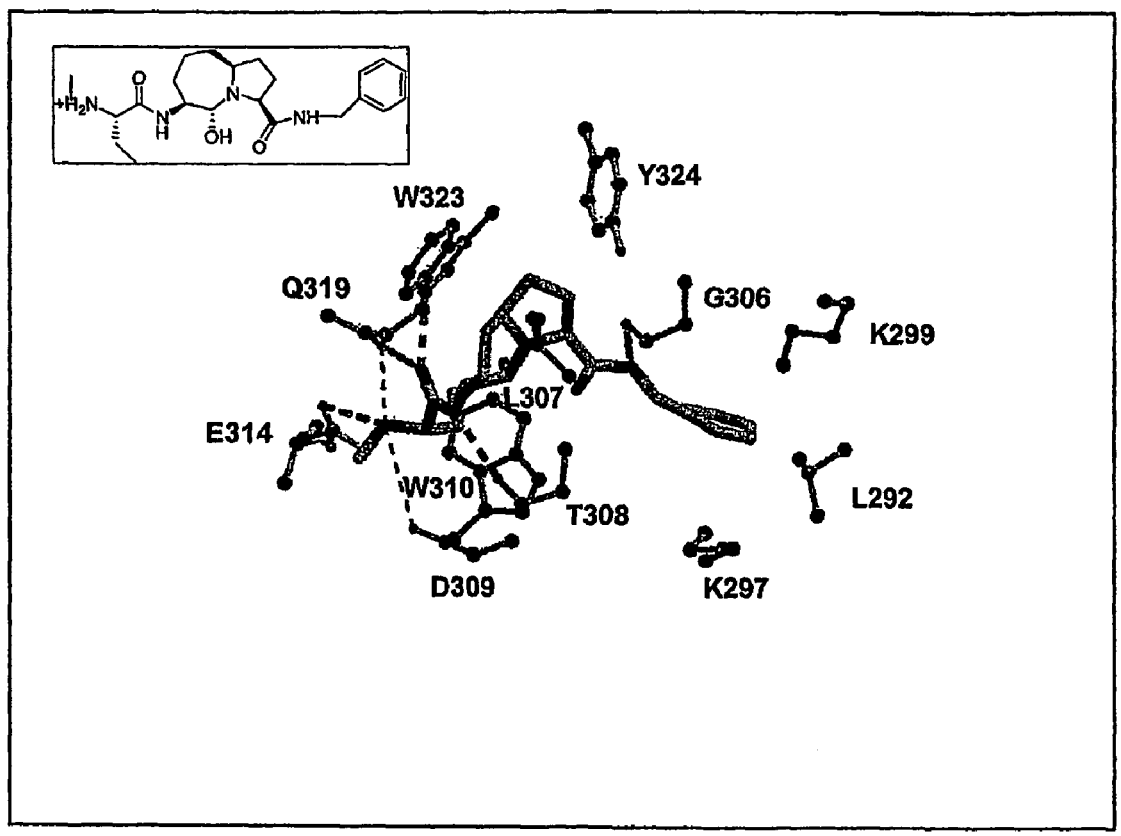
FIG. 9 shows the modeled complex of compound 37 in Table 2 and XIAP BIR3.
Figure 10:
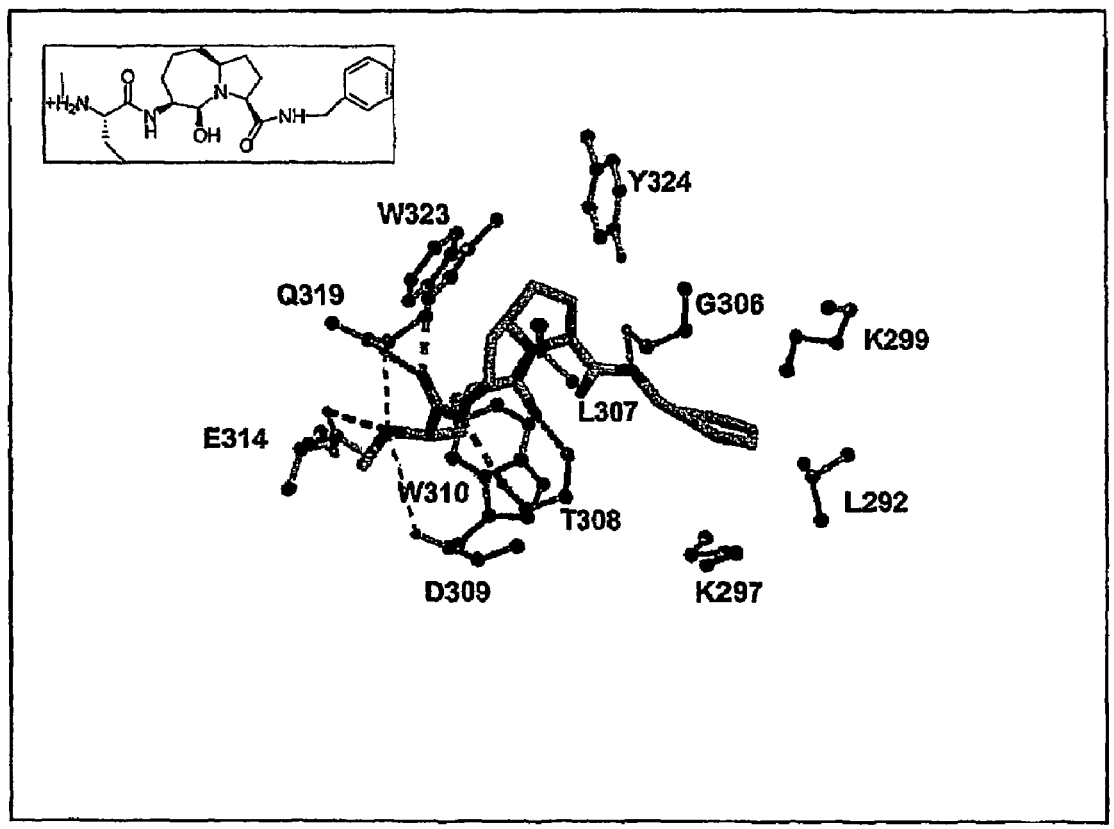
FIG. 10 shows the modeled complex of compound 38 in Table 2 and XIAP BIR3.
Figure 11:
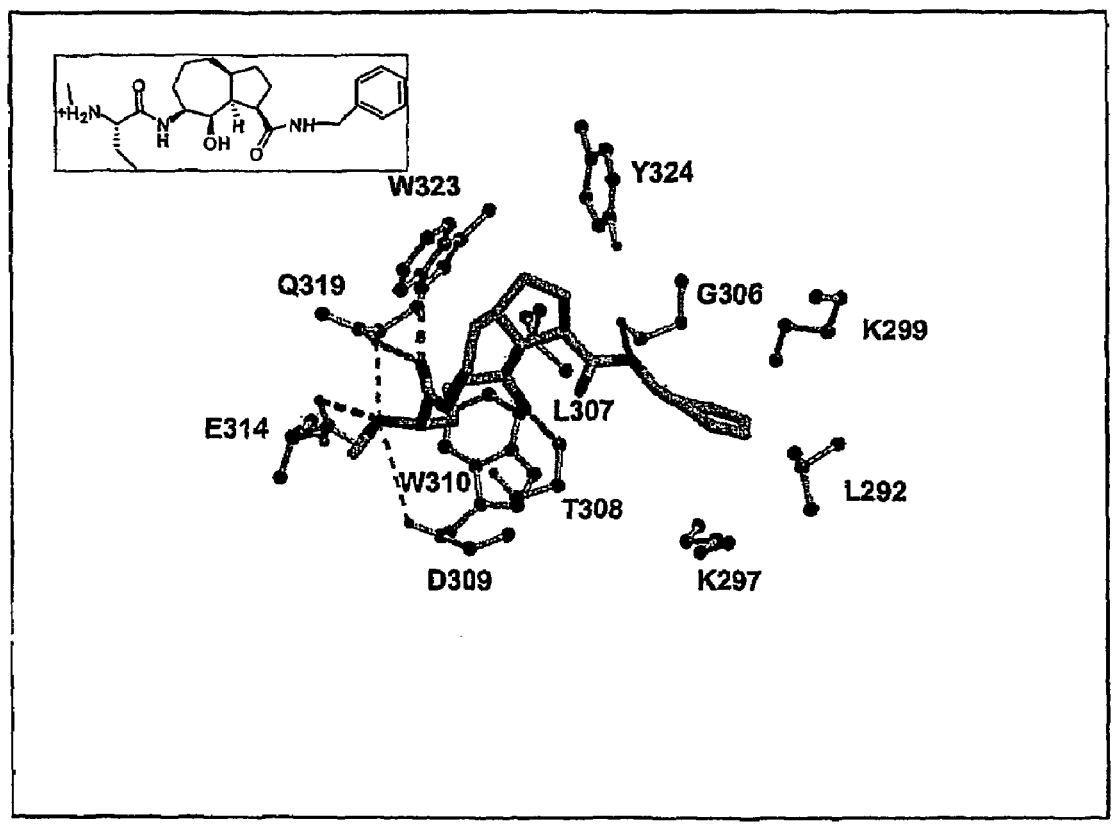
FIG. 11 shows the modeled complex of compound 39 in Table 2 and XIAP BIR3.
Figure 12:
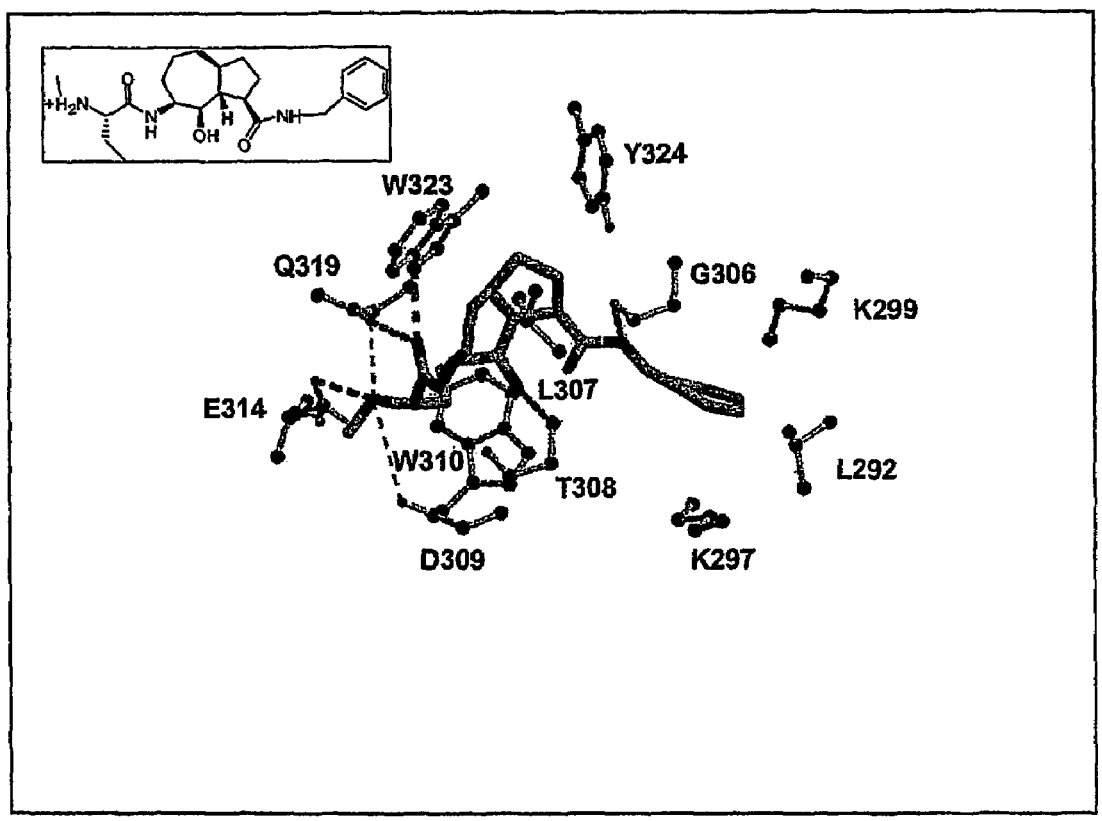
FIG. 12 shows the modeled complex of compound 40 in Table 2 and XIAP BIR3.
Figure 13:
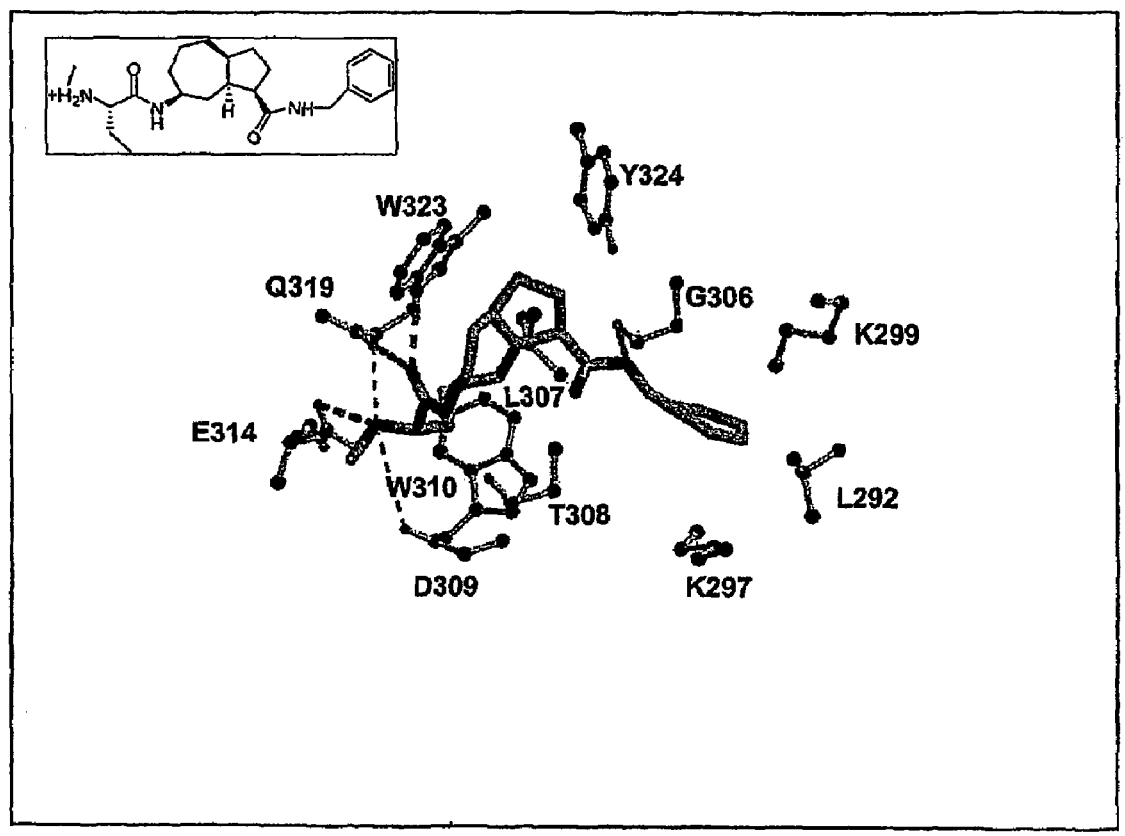
FIG. 13 shows the modeled complex of compound 41 in Table 2 and XIAP BIR3.
Figure 14:
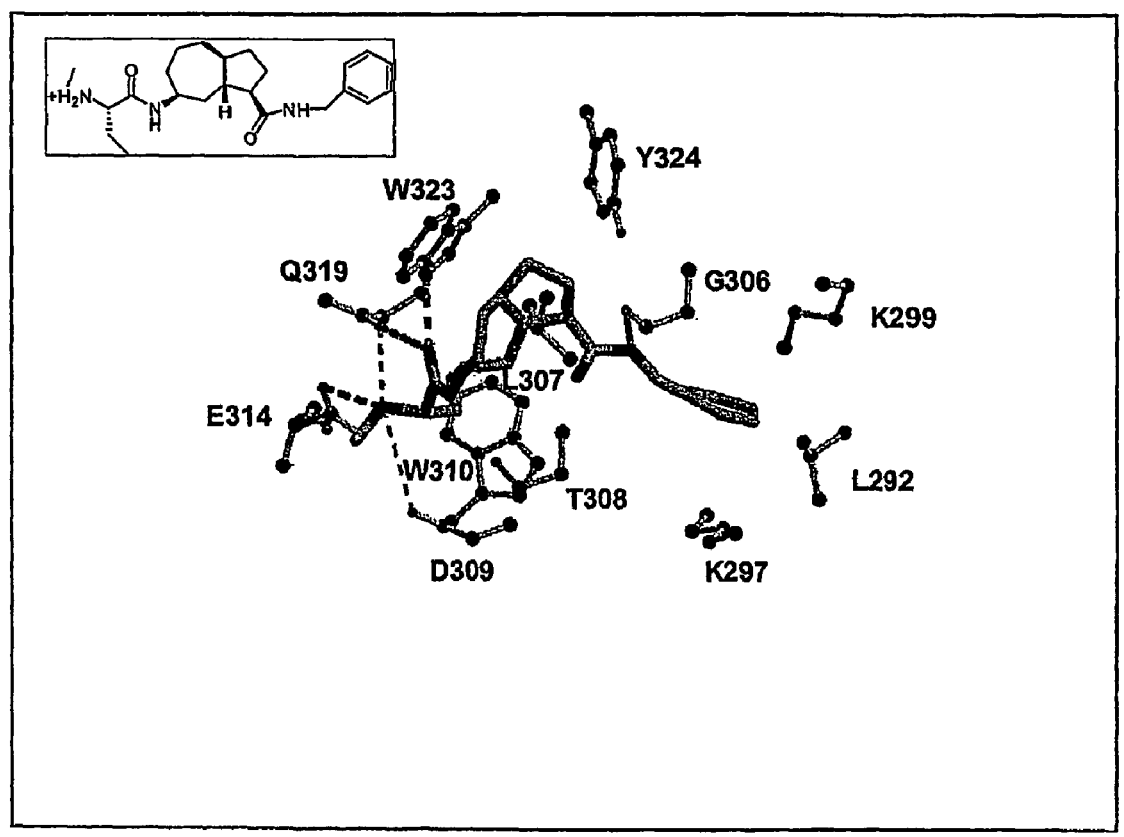
FIG. 14 shows the modeled complex of compound 42 in Table 2 and XIAP BIR3.

For compound 21 with the [5.3.0] bicyclic lactam system (Table 2), it was found that compound 21 even more closely mimics AVPI (SEQ ID NO:1) and compound 1 in both hydrogen bonding and hydrophobic interactions (FIG. 6). In fact, it appears that the newly formed 7-membered ring has additional favorable hydrophobic contacts with W323 residue in XIAP (FIG. 6). In contrast, the other stereoisomer compound 22 (Table 2) was found to be unable to maintain the hydrogen bonding and hydrophobic interactions with XIAP BIR3 in the modeled structure.

Based on the binding affinities of the [5.3.0] bicyclic lactam system, additional [5.3.0] compounds containing modifications of the lactam ring structure were modeled (Compounds 23-30 in Table 2). Based on the modeling results, these compounds are predicted to have good binding affinities (FIGS. 7-14).

Example 4

Synthesis of Smac Mimetics with [4.3.0], [5.3.0], and [6.3.0] Bicyclic Lactam System General Methods: NMR spectra were acquired at a proton frequency of 300 MHz. $^1$H chemical shifts are reported with Me$_4$Si (0.00 ppm), CHCl$_3$ (7.26 ppm), CD$_2$HOD (3.31 ppm), or DHO 04.79 ppm) as internal standards. $^{13}$C chemical shifts are reported with CDCl$_3$ (77.00 ppm), CD$_3$OD (49.00 ppm), or 1,4-dioxane (67.16 ppm) as internal standards. Optical rotations were measured at room temperature.

General Procedure A (for Hydrolysis of the Methyl Esters):

To a well-stirred solution of the substrate in 1,4-dioxane was added a solution of 2 N LiOH (2 eq) at room temperature. After all the starting material has been consumed, 1 N HCl was added until PH=5. Dichloromethane was used to extract the product, and the combined organic layers were washed with brine and dried over Na$_2$SO$_4$. After concentration, the residue was chromatographed on silica gel to give the product.

General Procedure B (for Preparation of Amides):

To a well-stirred mixture of the two substrates, EDCI (1.2 eq) and HOBt (1.2 eq) was added diisopropylethylamine at room temperature. The mixture was stirred overnight and then condensed. The residue was chromatographed on silica gel to give the product.

General Procedure C (for Deprotection of Boc):

To a well-stirred solution of the substrate was added a solution of 4.0 N HCl in 1,4-dioxane (4 eq). After stirring overnight, the solution was concentrated in vacuo. The residue was lyophilized to give the product.

General Procedure D (for Deprotection of Cbz):

To a solution of the substrate in MeOH was added 10% Pd—C (10% mmol). The mixture was stirred under H$_2$ overnight. After filtration of the catalyst, a solution of 4.0 N HCl in 1,4-dioxane (2 eq) was added. The solution was concentrated in vacuo. The residue was lyophilized to give product.

General Procedure E (for Alkylation of the Amino Group):

To a solution of the substrate in MeOH was added iodomethane (10 eq) or dibromide (4 eq). After addition of 5 eq of triethylamine, the solution was refluxed overnight. The solution was concentrated in vacuo. The residue was purified by chromatography to give trisubstituted amine. To a solution of the amine was added a solution of 4.0 N HCl in 1,4-dioxane (2 eq). The solvent was removed in vacuo and the residue was lyophilized to give product.

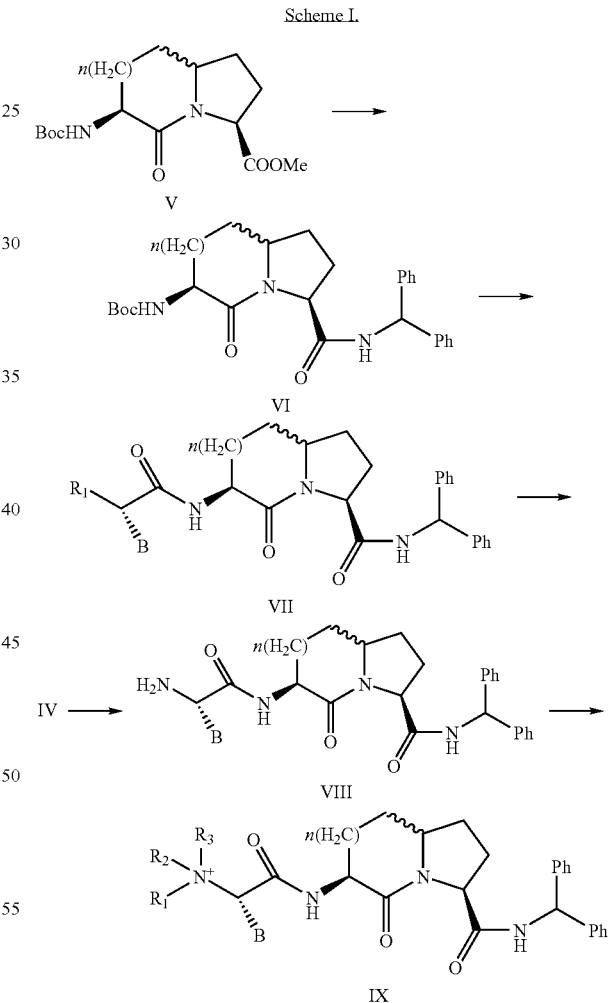

Compounds of general formula V can be synthesized according to reported methods (Scolastico et al., *Eur. J. Org. Chem.*, 2571 (2000); Harris et al., *Org. Lett.* 1847 (2003)) and as exemplified in Scheme I. Hydrolysis of the ester group according to General Procedure A gives acids. Condensation of these acids with amines, such as aminodiphenylmethane, according to General Procedure B will yield amide of general formula VI. Removal of the Boc or Cbz protective group according to General Procedure C or D and condensation with corresponding (L)—N-Boc amino acids, such as L—N-Boc-alanine or L—N-Boc-2-aminobutyric acid, according to General Procedure B will afford a series of amides of general formula VII. Removal of the Boc protective group according to General Procedure C will afford compounds of general formula VIII. Alkylation of the amino group in VIII according to General Procedure E will give compounds of general formula IX.

In a specific embodiment, compounds comprising a sulfur-containing ring can be synthesized according to reported methods (EP61187) and as exemplified in Scheme II.

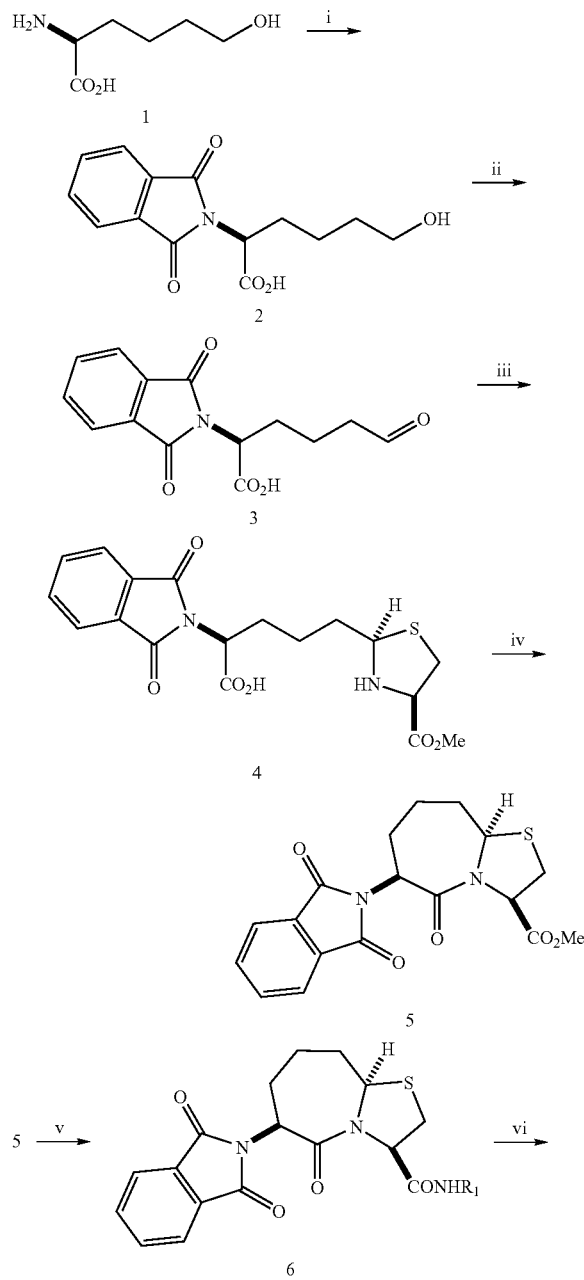

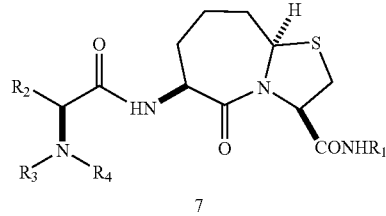

i. N-carbethoxyphthalimide, Na₂CO₃, then HCl; ii. Pyridinium dichromate, CH₂Cl₂; iii. L-cysteine methyl ester, THF, 2.5 h; iv. EEDQ, THF, overnight; v. a) aq. LiOH, dioxane, b) H₂NR₁, EDCI, HOBT, iPr₂NEt, CH₂Cl₂; vi. a) H₂NNH₂H₂O, EtOH, b) R₂CHNR₃R₄, EDCI, HOBT, iPr₂NEt, CH₂Cl₂.

In another specific embodiment, compounds comprising a heterocyclic ring for A can be synthesized as exemplified in Scheme III.

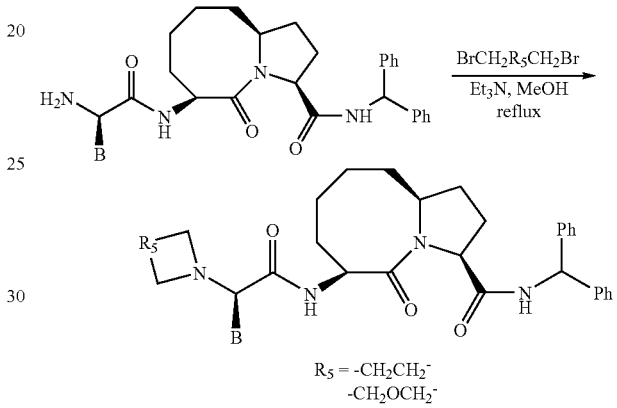

The following compounds were synthesized and their structures analyzed by the general procedures described above.

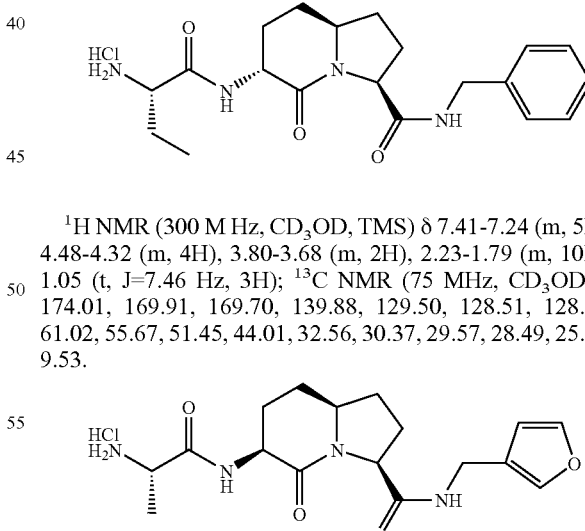

¹H NMR (300 M Hz, CD₃OD, TMS) δ 7.41-7.24 (m, 5H), 4.48-4.32 (m, 4H), 3.80-3.68 (m, 2H), 2.23-1.79 (m, 10H), 1.05 (t, J=7.46 Hz, 3H); ¹³C NMR (75 MHz, CD₃OD) δ 174.01, 169.91, 169.70, 139.88, 129.50, 128.51, 128.10, 61.02, 55.67, 51.45, 44.01, 32.56, 30.37, 29.57, 28.49, 25.67, 9.53.

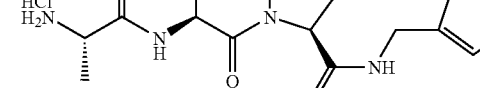

¹H NMR (300 M Hz, CD₃OD, TMS) δ 7.45 (m, 1H), 6.36 (m, 1H), 6.30 (m, 1H), 4.51-4.36 (m, 4H), 3.97 (m, 1H), 3.67 (m, 1H), 2.50-1.70 (m, 8H), 1.30 (d, J=8.5 Hz, 3H); ¹³C NMR (75 MHz, CD₃OD) δ 173.93, 170.81, 169.79, 152.86, 143.32, 111.36, 108.06, 61.01, 59.89, 53.03, 50.36, 37.34, 32.78, 30.47, 28.28, 26.95, 17.54.

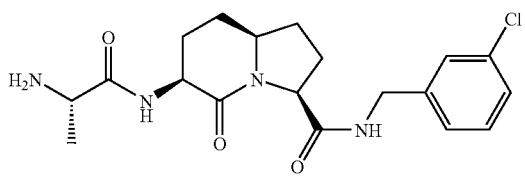

¹H NMR (300 MHz, CD₃OD, TMS) δ 7.42-7.22 (m, 5H), 4.56-4.24 (m, 4H), 3.92 (m, 1H), 3.68 (m, 1H), 2.45-1.55 (m, 8H), 1.50 (d, J=8.2 Hz, 3H); ¹³C NMR (75 MHz, CD₃OD) δ 174.23, 170.80, 169.69, 142.33, 135.32, 131.05, 128.37, 128.18, 126.45, 61.08, 59.97, 50.37, 43.49, 32.83, 30.44, 28.35, 26.91, 17.58.

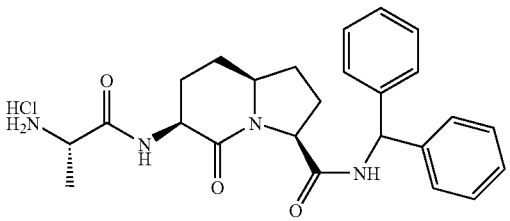

¹H NMR (300 MHz, CD₃OD, TMS) δ 7.45-7.26 (m, 10H), 6.13 (s, 1H), 4.55 (m, 2H), 3.91 (m, 1H), 3.68 (m, 1H), 2.31-1.65 (m, 8H), 1.53 (d, J=6.5 Hz, 3H); ¹³C NMR (75 MHz, CD₃OD) δ 173.25, 170.74, 169.74, 143.03, 142.70, 129.65, 129.41, 128.71, 128.57, 128.49, 128.19, 68.11, 60.90, 59.78, 58.43, 50.41, 32.84, 30.41, 28.18, 26.94, 17.55.

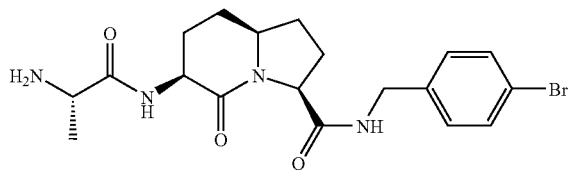

¹H NMR (300 MHz, CD₃OD, TMS) δ 7.47 (d, J=8.5 Hz, 2H), 7.23 (d, J=8.5 Hz, 2H), 4.65-4.19 (m, 4H), 3.92 (m, 1H), 3.75 (m, 1H), 2.52-1.65 (m, 8H), 1.52 (d, J=8.2 Hz, 3H); ¹³C NMR (75 MHz, CD₃OD) δ 174.29, 170.75, 169.76, 139.25, 132.53, 130.28, 121.74, 61.11, 60.06, 50.37, 43.42, 32.87, 29.42, 28.44, 26.86, 17.54.

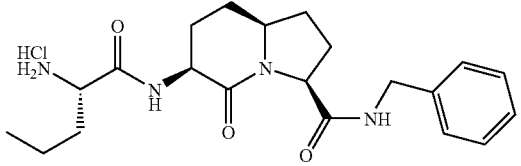

¹H NMR (300 MHz, CD₃OD, TMS) δ 7.36-7.23 (m, 5H), 4.47-4.38 (m, 4H), 3.84 (m, 1H), 3.76 (m, 1H), 2.20-1.65 (m, 10H), 1.52 (m, 2H), 0.99 (t, J=7.3 Hz, 3H); ¹³C NMR (75 MHz, CD₃OD) δ 174.07, 170.09, 169.66, 139.81, 129.70, 128.68, 128.35, 61.09, 59.94, 54.56, 53.39, 44.06, 34.75, 32.85, 30.49, 28.36, 26.92, 19.22, 14.04.

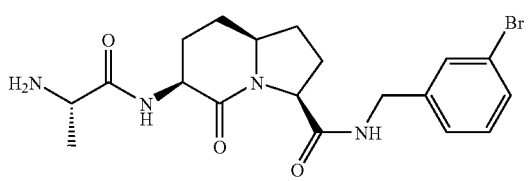

¹H NMR (300 MHz, CD₃OD, TMS) δ 7.51-7.22 (m, 5H), 4.52-4.31 (m, 4H), 3.95 (m, 1H), 3.65 (m, 1H), 2.40-1.72 (, 8H), 1.56 (d, J=8.0 Hz, 3H); ¹³C NMR (75 MHz, CD₃OD) δ 174.19, 170.80, 169.81, 142.59, 131.33, 131.21, 127.20, 123.38, 61.09, 60.01, 50.37, 43.43, 32.81, 30.40, 28.36, 26.90, 17.61.

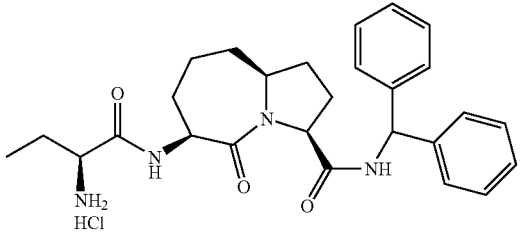

¹H NMR (300 MHz, D₂O) δ 7.34-7.21 (m, 10H), 5.96 (s, 1H), 4.51-4.44 (m, 2H), 3.96-3.84 (m, 2H), 2.20-1.52 (m, 12H), 0.93 (t, J=7.6 Hz, 3H); ¹³C NMR (75 MHz, D₂O) δ 173.49, 172.53, 169.23, 141.28, 141.12, 129.30, 129.19, 128.15, 127.66, 127.49, 62.41, 59.93, 58.01, 54.60, 54.07, 33.14, 32.82, 29.66, 28.16, 27.33, 24.75, 8.76.

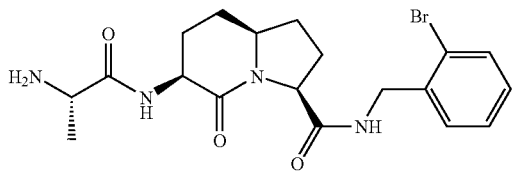

¹H NMR (300 MHz, CD₃OD, TMS) δ 7.38-72.3 (m, 5H, 4.61 (m, 1H), 4.36 (m, 1H), 4.02 (m, 1H), 3.85-3.65 (m, 2H), 3.21-3.12 (m, 2H), 2.38-1.72 (m, 8H), 1.55 (t, J=6.9 Hz, 3H); ¹³C NMR (75 MHz, CD₃OD) δ 173.60, 173.41, 171.08, 170.23, 138.66, 130.37, 129.53, 127.79, 61.39, 60.57, 55.73, 52.68, 50.35, 38.17, 32.38, 29.91, 29.12, 27.01, 17.57.

129.41, 128.70, 128.59, 128.53, 128.18, 60.88, 59.79, 58.46, 55.71, 32.85, 30.36, 28.19, 26.90, 25.97, 9.62.

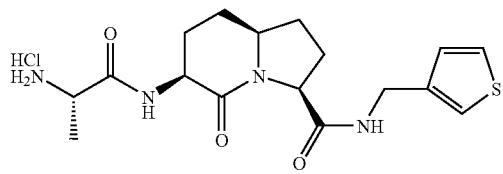

¹H NMR (300 M Hz, CD₃OD, TMS) δ 7.37-7.21 (m, 3H), 4.53-4.34 (m, 4H), 3.93 (m, 1H), 3.67 (m, 1H), 2.42-1.65 (m, 8H), 1.54 (d, J=7.0 Hz, 3H); ¹³C NMR (75 MHz, CD₃OD) δ 174.01, 170.69, 169.82, 139.78, 129.52, 128.33, 128.14, 61.08, 60.12, 50.47, 44.01, 32.82, 30.54, 28.32, 26.92, 17.55.

¹H NMR (300 M Hz, CD₃OD, TMS) δ 7.34-7.09 (m, 10H), 4.51-4.43 (m, 2H), 3.90-3.55 (m, 3H), 3.27-2.98 (m, 2H), 2.52-1.43 (m, 10H), 1.10 (t, J=7.5 Hz, 3H); ¹³C NMR (75 MHz, CD₃OD) δ 173.04, 169.90, 168.78, 143.05, 139.35, 130.33, 129.38, 129.25, 128.25, 127.93, 127.63, 61.01, 59.76, 56.94, 55.71, 43.45, 32.59, 30.18, 28.23, 26.97, 25.97, 9.62.

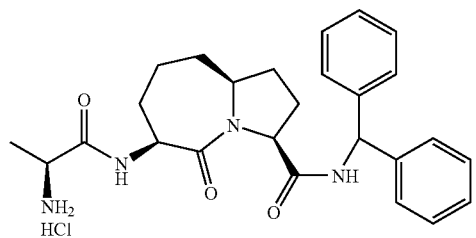

¹H NMR (300 M Hz, D₂O) δ 7.32-7.20 (m, 10H), 5.94 (s, 1H), 4.48-4.41 (m, 2H), 4.02-3.88 (m, 2H), 2.16-1.50 (m, 10H), 1.44 (d, J=7.2 Hz, 3H); ¹³C NMR (75 MHz, D₂O) δ 173.48, 172.62, 170.13, 141.29, 141.11, 129.30, 129.20, 128.15, 128.11, 127.66, 127.49, 62.45, 59.89, 57.99, 54.01, 49.32, 33.16, 32.83, 29.43, 28.15, 27.31, 16.89.

¹H NMR (300 M Hz, CD₃OD, TMS) δ 7.37-7.19 (m, 5H), 4.52-4.45 (m, 2H), 4.13 (m, 1H), 3.80-3.54 (m, 2H), 2.56-1.69 (m, 8H), 1.60-1.45 (m, 6H); ¹³C NMR (75 MHz, CD₃OD) δ 173.11, 170.73, 169.68, 144.89, 129.45, 128.41, 127.21, 61.04, 59.93, 53.06, 50.31, 32.89, 30.78, 28.37, 26.94, 22.60, 17.59.

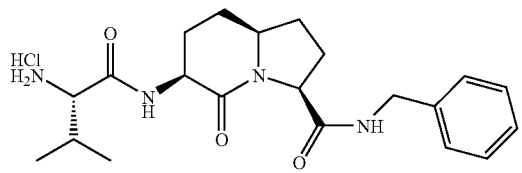

¹H NMR (300 M Hz, CD₃OD, TMS) δ 7.35-7.18 (m, 5H), 4.56-4.32 (m, 4H), 3.85-3.62 (m, 2H), 2.42-1.70 (m, 9H), 1.18 (d, J=7.2 Hz, 6H); ¹³C NMR (75 MHz, CD₃OD) δ 174.07, 169.62, 169.27, 139.83, 129.50, 128.35, 128.11, 61.09, 59.90, 44.06, 32.84, 31.55, 30.49, 28.33, 26.96, 18.98, 18.05.

¹H NMR (300 M Hz, CD₃OD, TMS) δ 7.39-7.20 (m, 5H), 4.52-4.30 (m, 4H), 3.88-3.62 (m, 2H), 2.45-1.76 (m, 10H), 1.04 (t, J=7.5 Hz, 3H); ¹³C NMR (75 MHz, CD₃OD) δ 174.07, 169.88, 169.65, 139.79, 129.48, 128.32, 128.08, 61.08, 59.93, 55.68, 44.02, 32.81, 30.46, 29.14, 28.36, 26.89, 9.58.

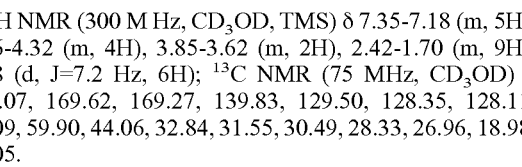

¹H NMR (300 M Hz, CD₃OD, TMS) δ 7.42-7.18 (m, 10H), 6.13 (s, 1H), 4.59-4.52 (m, 2H), 3.87-3.67 (m, 2H), 2.21-1.71 (m, 10H), 1.07 (t, J=7.5 Hz, 3H); ¹³C NMR (75 MHz, CD₃OD) δ 173.31, 169.90, 169.64, 143.04, 142.74, 129.76,

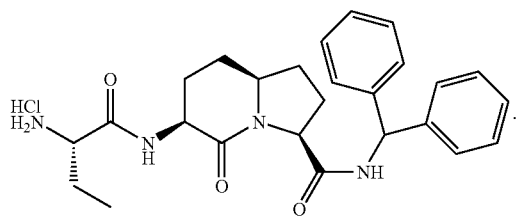

¹H NMR (300 M Hz, CD₃OD, TMS) δ 7.57 (m, 1H), 7.38 (m, 1H), 7.12-6.95 (m, 3H), 4.52 (m, 1H), 4.31 (m, 1H), 4.05 (m, 1H), 3.80-3.65 (m, 2H), 3.55 (m, 1H), 3.20-2.82 (m, 2H), 2.43-1.82 (m, 8H), 1.52 (d, J=7.0 Hz, 3H); $^{13}$C NMR (75 MHz, CD$_3$OD) δ 172.96, 171.30, 169.53, 138.11, 128.74, 123.71, 122.36, 119.67, 119.33, 112.79, 112.29, 62.19, 61.20, 59.93, 53.07, 41.60, 32.66, 30.28, 29.22, 26.03, 17.57.

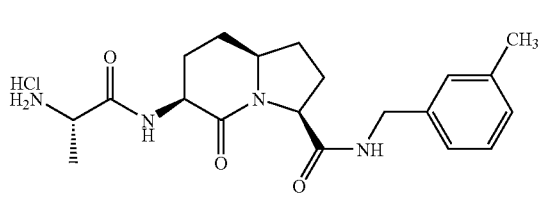

$^1$H NMR (300 M Hz, CD$_3$OD, TMS) δ 7.26-7.05 (m, 4H), 4.55-4.20 (m, 4H), 4.05 (m, 1H), 3.59 (m, 1H), 2.52-1.68 (m, 11H), 1.60 (d, J=7.1 Hz, 3H); $^{13}$C NMR (75 MHz, CD$_3$OD) δ 172.96, 171.29, 169.79, 139.55, 139.17, 129.43, 129.18, 128.80, 125.72, 62.24, 61.34, 53.41, 53.03, 44.51, 30.45, 29.45, 29.19, 21.42, 17.56.

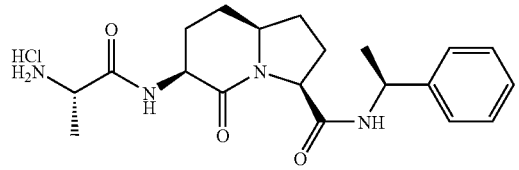

$^1$H NMR (300 M Hz, CD$_3$OD, TMS) δ 7.45-7.22 (m, 5H), 4.55-4.36 (m, 2H), 3.95 (m, 1H), 3.68 (m, 2), 2.30-1.68 (m, 8H), 1.53 (d, J=7.2 Hz, 3H), 1.48 (d, J=7.0 Hz, 3H); $^{13}$C NMR (75 MHz, CD$_3$OD) δ 172.90, 170.75, 169.71, 145.30, 132.41, 129.58, 128.10, 126.91, 68.13, 60.93, 59.79, 50.40, 32.73, 30.31, 29.11, 28.20, 26.77, 22.53, 17.52.

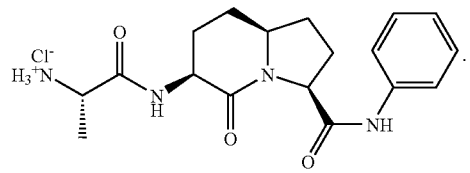

$^1$H NMR (300 M Hz, CD$_3$OD, TMS) δ 7.64-7.57 (m, 2H), 7.38-7.29 (m, 2H), 7.10 (m, 1H), 4.60-4.52 (m, 2H), 3.94 (m, 1H), 3.79 (m, 1H), 2.42-1.70 (m, 8H), 1.54 (d, J=7.2 Hz, 3H); $^{13}$C NMR (75 MHz, CD$_3$OD) δ 172.24, 170.82, 169.86, 139.72, 129.80, 125.29, 121.10, 68.12, 61.68, 59.79, 50.38, 32.89, 30.47, 28.18, 27.06, 17.52.

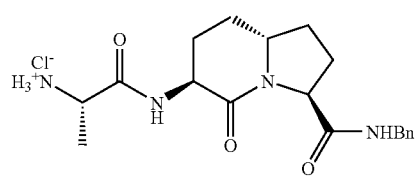

$^1$H NMR (300 M Hz, CD$_3$OD, TMS) δ 7.40-7.19 (m, 5H), 4.54-4.29 (m, 4H), 3.92 (m, 1H), 3.80 (m, 1H), 2.52-1.78 (m, 8H), 1.55 (d, J=7.5 Hz, 3H); $^{13}$C NMR (75 MHz, CD$_3$OD) δ 174.44, 170.99, 169.62, 139.90, 129.49, 128.34, 128.11, 62.06, 61.41, 51.73, 50.29, 43.84, 33.86, 29.79, 28.84, 28.45, 17.30.

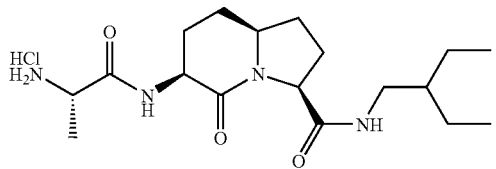

$^1$H NMR (300 M Hz, CD$_3$OD, TMS) δ 4.53 (m, 1H), 4.36 (m, 1H), 4.08 (m, 1H), 3.68 (m, 1H), 3.32-3.14 (m, 2H), 2.52-1.65 (m, 8H), 1.56 (d, J=7.2 Hz, 3H), 1.52-1.30 (m, 5H), 0.92 (t J=7.4 Hz, 6H); $^{13}$C NMR (75 MHz, CD$_3$OD) δ 172.93, 171.38, 169.72, 62.28, 61.28, 53.41, 53.03, 43.37, 42.21, 30.79, 30.43, 29.42, 29.20, 24.66, 17.56, 11.19.

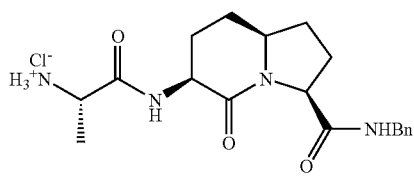

$^1$H NMR (300 M Hz, D$_2$O) δ 7.32-7.16 (m, 5H), 4.36-4.28 (m, 4H), 3.94 (m, 1H), 3.60 (m, 1H), 2.43-1.52 (m, 8H), 1.43 (d, J=7.0 Hz, 3H).

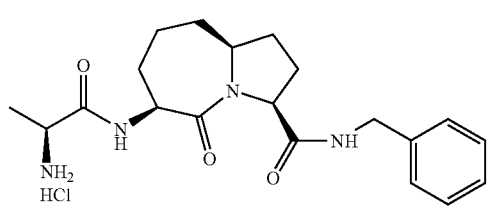

$^1$H NMR (300 M Hz, D$_2$O) δ 7.45-7.18 (m, 5H), 4.47-4.38 (m, 2H), 4.30 (brs, 2H), 4.01-3.92 (m, 2H), 2.32-1.51 (m, 10H), 1.48 (d, J=7.1 Hz, 3H); $^{13}$C NMR (75 MHz, D$_2$O) δ 174.26, 172.74, 170.16, 138.35, 129.12, 127.76, 127.45, 62.70, 60.00, 54.05, 49.32, 43.28, 33.20, 32.83, 29.44, 28.20, 27.34, 16.91.

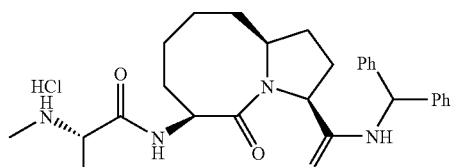

$^1$H NMR (300 M Hz, D$_2$O) δ 7.30-7.18 (m, 10H), 5.95 (s, 1H), 4.74 (m, 1H), 4.34 (m, 1H), 4.24 (m, 1H), 3.83 (m, 1H), 2.57 (s, 3H), 2.21-1.50 (m, 11H), 1.40 (d, J=7.0 Hz, 3H), 1.38 (m, 1H); $^{13}$C NMR (75 MHz, D$_2$O) δ 173.77, 172.62, 169.95, 141.56, 141.28, 129.54, 129.44, 128.40, 128.35, 128.01, 127.82, 62.50, 61.40, 58.16, 57.49, 51.42, 36.16, 33.30, 32.64, 31.61, 28.07, 25.36, 22.14, 15.95.

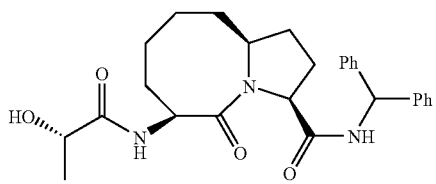

¹H NMR (300 MHz, CDCl₃, TMS) δ 7.78 (brd, J=8.4 Hz, 1H), 7.37-7.20 (m, 11H), 6.22 (brd, J=8.5 Hz, 1H), 4.88 (m, 1H), 4.64 (m, 1H), 4.23 (m, 2H), 3.80 (brs, 1H), 2.50 (m, 1H), 2.12 (m, 1H), 2.08-1.75 (m, 4H), 1.74-1.39 (m, 5H), 1.41 (d, J=7.2 Hz, 3H), 1.27 (m, 1H); ¹³C NMR (75 MHz, CDCl₃) δ 174.17, 172.08, 169.77, 141.63, 141.47, 128.60, 128.52, 127.52, 127.36, 127.22, 68.27, 60.32, 59.48, 57.10, 49.55, 36.59, 35.36, 32.16, 25.03, 24.70, 22.94, 20.87.

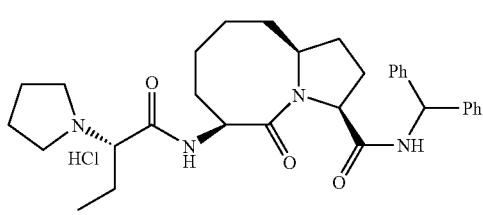

¹H NMR (300 MHz, D₂O) δ 7.30-7.19 (m, 10H), 5.95 (s, 1H), 4.77 (m, 1H), 4.36 (m, 1H), 4.25 (m, 1H), 3.68 (m, 1H), 3.50-2.70 (brs, 4H), 2.23-1.39 (m, 18H), 0.85 (t, J=7.2 Hz, 3H); ¹³C NMR (75 MHz, D₂O) δ 173.78, 172.23, 168.82, 141.60, 141.26, 129.54, 129.45, 128.38, 128.06, 127.74, 69.12, 62.40, 61.45, 58.22, 51.52, 36.17, 33.45, 32.66, 28.12, 26.40, 25.38, 23.64, 23.23, 22.10, 8.98.

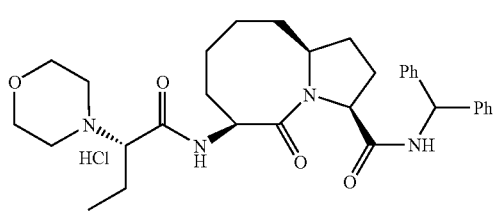

¹H NMR (300 MHz, D₂O) δ 7.30-7.19 (m, 10H), 5.95 (s, 1H), 4.79 (m, 1H), 4.37 (m, 1H), 4.25 (m, 1H), 3.86 (brs, 4H), 3.67 (m, 1H), 3.31-3.20 (m, 4H), 2.18-1.39 (m, 14H), 0.85 (t, J=7.2 Hz, 3H); ¹³C NMR (75 MHz, D₂O) δ 173.77, 172.16, 167.95, 141.61, 141.26, 129.54, 129.45, 128.38, 128.06, 127.74, 70.21, 64.28, 62.40, 61.45, 58.22, 51.58, 51.02, 36.17, 33.44, 32.66, 28.12, 25.37, 22.09, 21.22, 9.14.

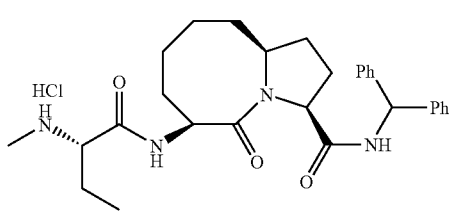

¹H NMR (300 MHz, D₂O) δ 7.32-7.19 (m, 10H), 5.95 (s, 1H), 4.75 (m, 1H), 4.36 (m, 1H), 4.25 (m, 1H), 3.71 (m, 1H), 2.56 (s, 3H), 2.18-1.40 (m, 14H), 0.87 (t, J=7.6 Hz, 3H); ¹³C NMR (75 MHz, D₂O) δ 173.76, 172.39, 168.73, 141.60, 141.27, 129.54, 129.44, 128.37, 128.05, 127.76, 62.96, 62.41, 61.44, 58.21, 51.51, 36.18, 33.40, 32.66, 32.04, 28.10, 25.38, 24.08, 22.11, 8.81.

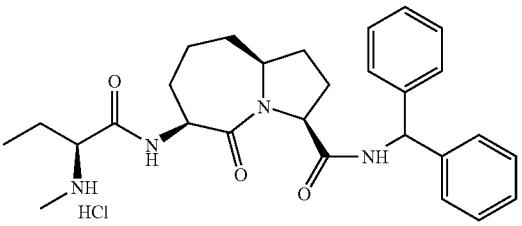

¹H NMR (300 MHz, D₂O) δ 7.34-7.19 (m, 10H), 5.96 (s, 1H), 4.52-4.46 (m, 2H), 3.91 (m, 1H), 3.73 (m, 1H), 2.56 (s, 3H), 2.18-1.45 (m, 12H), 0.91 (t, J=7.5 Hz, 3H); ¹³C NMR (75 MHz, D₂O) δ 173.73, 172.62, 168.32, 141.54, 141.37, 129.56, 129.45, 128.41, 128.38, 127.92, 127.75, 63.23, 62.67, 60.20, 58.27, 54.45, 33.38, 33.08, 32.05, 29.98, 28.43, 27.58, 24.09, 8.80.

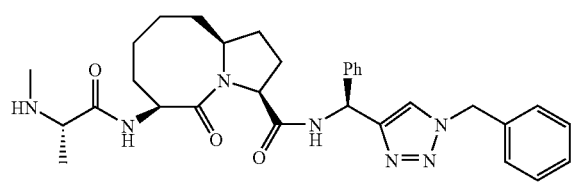

¹H NMR (300 MHz, D₂O) δ 7.60 (s, 1H), 7.20-6.98 (m, 10H), 6.05 (s, 1H), 5.25 (s, 2H), 4.63 (m, 1H), 4.24 (m, 1H), 4.09 (m, 1H), 3.75 (m, 1H), 2.52 (s, 3H), 2.10-1.18 (m, 15H).

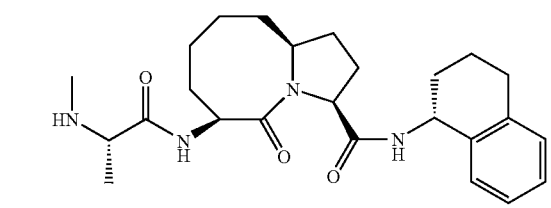

¹H NMR (300 MHz, D₂O) δ 7.22-7.04 (m, 4H), 4.87 (m, 1H), 4.70 (m, 1H), 4.32-4.16 (m, 2H), 3.90-3.78 (m, 1H), 2.68-2.60 (m, 2H), 2.56 (s, 3H), 2.16-1.42 (m, 16), 1.40 (d, J=7.2 Hz, 3H); ¹³C NMR (75 MHz, D₂O) δ 173.34, 172.42, 169.58, 138.33, 136.18, 129.48, 128.65, 127.78, 126.59, 62.48, 61.18, 57.21, 51.20, 48.34, 35.98, 33.02, 32.37, 31.33, 29.80, 28.81, 27.90, 25.16, 21.89, 20.19, 15.66.

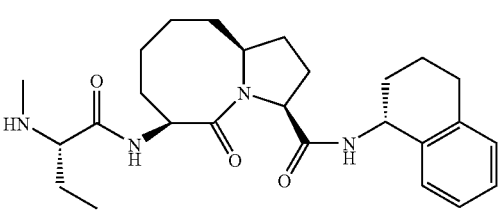

¹H NMR (300 MHz, D₂O) δ 7.22-7.04 (m, 4H), 4.87 (m, 1H), 4.70 (m, 1H), 4.32-4.16 (m, 2H), 3.74 (m, 1H), 2.68-2.60 (m, 2H), 2.56 (s, 3H), 2.22-1.32 (m, 18), 0.87 (t, J=7.5 Hz, 3H); ¹³C NMR (75 MHz, D₂O) δ 173.41, 172.22, 169.47, 138.33, 136.15, 129.49, 128.71, 127.79, 126.57, 62.70, 62.40, 61.24, 51.29, 48.37, 36.01, 33.14, 32.39, 31.79, 29.78, 28.82, 27.95, 25.19, 23.81, 21.86, 20.14, 8.56.

Example 5

Synthesis of Smac Mimetics with [7.3.0] Bicyclic Lactam System

Compounds comprising a [7.3.0] bicyclic lactam system can be synthesized exemplified in Scheme IV.

Scheme IV.

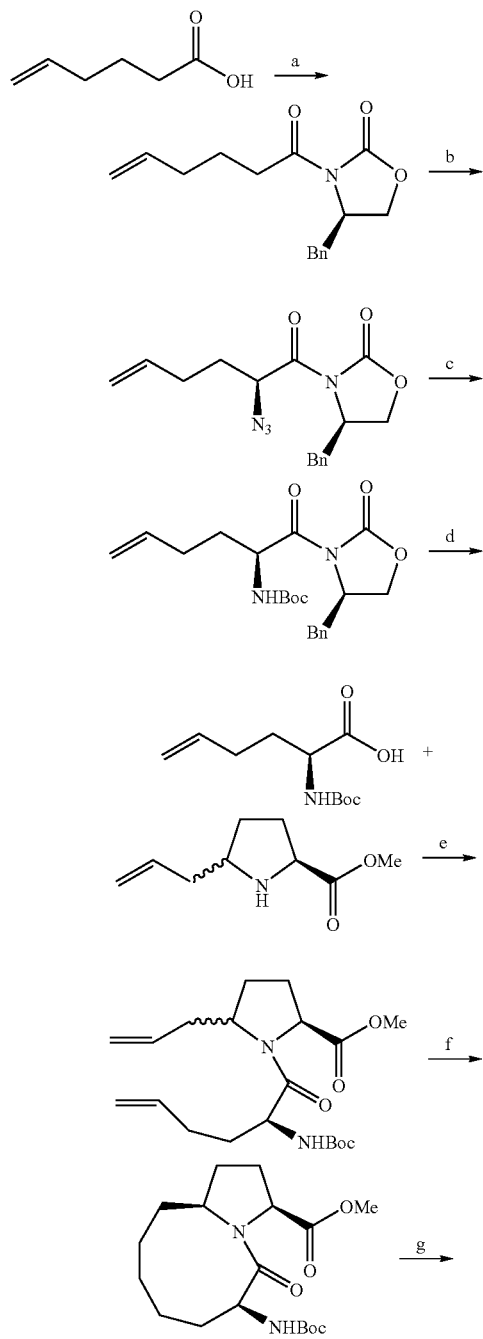

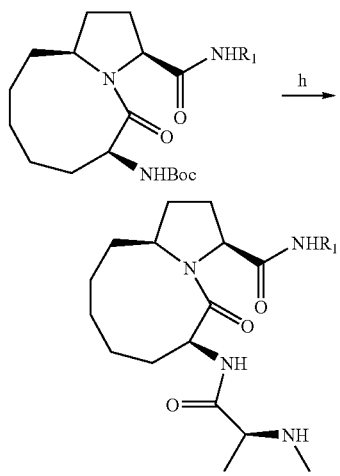

(a) i. Et₃N, pivaloyl chloride; ii. Evans oxazolidinone, LDA; (b) i. KHMDS; ii. trisyl azide; (c) i. SnCl₂, MeOH; ii. Boc₂O, dioxane, NaHCO₃; (d) LiOH; (e) EDCl, HOBt, DIPEA; (f) i. Grubbs' catalyst, CH₂Cl₂; ii. H₂, 10% Pd-C, MeOH; (g) i. LiOH; ii. R₁NH₂, EDCl, HOBt; (h) i. HCl in MeOH; ii. Boc-N-Me-Ala-OH, EDCl, HOBt, DIPEA; iii. HCl in MeOH.

The following compounds were synthesized and their structures analyzed by the general procedures described above.

¹H NMR (300 M Hz, D₂O) δ 7.30-7.18 (m, 10H), 5.92 (s, 1H), 4.75 (m, 1H), 4.35 (m, 1H), 4.05 (m, 1H), 3.79 (m, 1H), 2.54 (s, 3H), 2.01 (m, 2H), 1.90-1.32 (m, 12H), 1.36 (d, J=7.0 Hz, 3H).

¹H NMR (300 M Hz, D₂O) δ 7.18-7.02 (m, 4H), 4.84 (m, 2H), 4.32 (m, 1H), 4.15 (m, 1H), 3.80 (m, 1H), 2.61 (m, 2H), 2.55 (s, 3H), 1.85 (m, 2H), 1.80-1.40 (m, 16H), 1.35 (d, J=7.0 Hz, 3H).

Example 6

Binding Affinities of Smac Mimetics with [4.3.0] Bicyclic Lactam System

Compound 19 with the [4.3.0] bicyclic lactam system was synthesized as described in Example 4. To validate the modeling prediction, compound 20 was also synthesized. These two compounds were tested in the FP-based binding assay and the binding data is provided in Table 3. It was found that while compound 19 has a $K_i$ value of less than 10 μM, compound 20 did not show any binding up to 200 μM. The binding data is consistent with the modeling results. Of note, compound 19 is approximately 15-fold less potent than compound 1 and Smac AVPI peptide (SEQ ID NO:1), which may be attributed to the less effective interactions between the five-membered ring in compound 19 with W323 in XIAP as compared to the proline ring in compound 1 and Smac AVPI peptide (SEQ ID NO:1).

Figure 15:
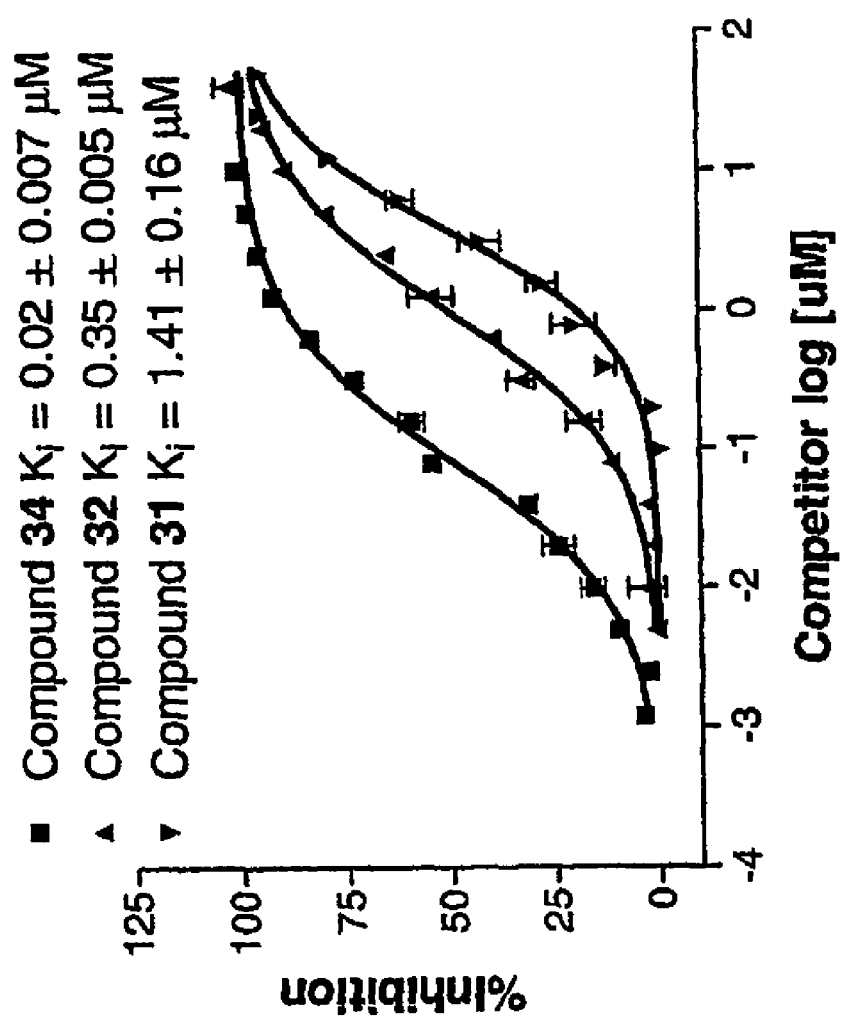
FIG. 15 shows the binding of Smac mimetics in the FP-based assay.

The studies with simple Smac mimetics suggested that replacement of the methyl group in A1' with an ethyl group may improve the binding for compound 19. Compound 31 (Table 3) was thus synthesized in which the methyl group in compound 19 was replaced by an ethyl group. The data with simple Smac mimetics also suggested that replacement of the benzyl group in compound 19 with a diphenylmethyl group may further improve the binding affinity. Compound 32 (Table 3) was thus synthesized. These compounds were tested in the FP-based assay and their binding data are provided in Table 3. As can be seen, compound 31 has a $K_i$ value of 1.41 μM, 3-fold more potent than compound 19 (FIG. 15). Compound 32 has a $K_i$ value of 0.35 μM, four-fold more potent than compound 31 and 12-fold more potent than compound 19 (FIG. 15). Of note, compound 32 is as potent as the natural AVPI Smac peptide (SEQ ID NO:1) and the simple mimetic compound 1.

TABLE 3

| Compound | Structure | $K_i$ (μM) |
| --- | --- | --- |
| 1 | 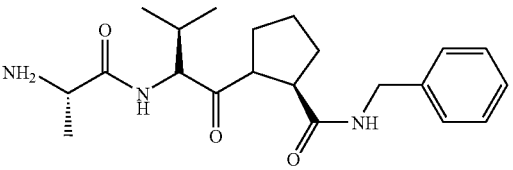 | 0.29 ± 0.06 |
| 19 | 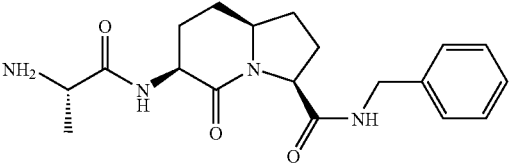 | 4.47 ± 0.65 |
| 20 | 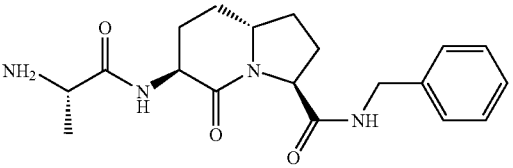 | >200 |
| 31 | 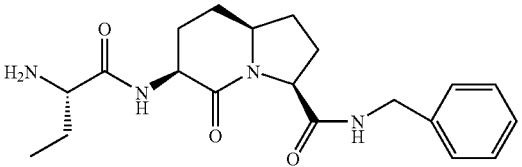 | 1.41 ± 0.16 |
| 32 | 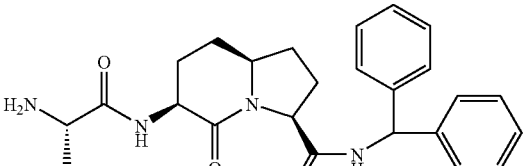 | 0.35 ± 0.005 |

Example 7

Binding Affinities of Smac Mimetics with [5.3.0] Bicyclic Lactam System

The modeling results suggested that compound 21 with the [5.3.0] bicyclic lactam system may have a better binding to XIAP BIR3 than compound 19 with the [4.3.0] bicyclic system. Compound 21 was therefore synthesized. Based upon the binding data for compounds 19 and 20, only stereoisomer 19 is active and thus compound 22 was not synthesized.

Compound 21 was synthesized using the methods detailed in Example 4. Compound 21 was determined to have a $K_i$ value of 0.15 μM, and is thus 30-fold more potent than the corresponding compound 19 with the [4.3.0] bicyclic lactam system (Table 4). Compound 21 is in fact two-fold more potent than the simple Smac mimetic compound 1 and the natural Smac AVPI peptide (SEQ ID NO:1), confirming the modeling prediction and design strategy.

TABLE 4

| Compound | Structure | $K_i$ (μM) |
|---|---|---|
| 21 | 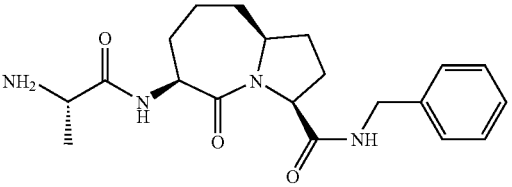 | 0.15 ± 0.015 |
| 33 | 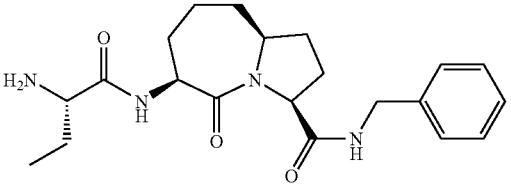 | 0.06 ± 0.015 |
| 34 | 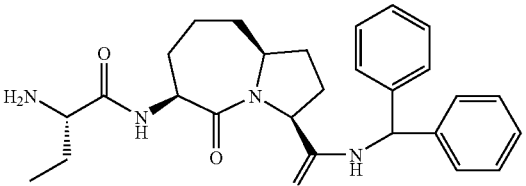 | 0.02 ± 0.007 |

Compounds 33 and 34 were designed and synthesized using similar methods as for compound 21 (Table 4). Compound 33 has a $K_i$ value of 0.06 μM (60 nM), while compound 34 has a $K_i$ of 0.02 μM (20 nM) (FIG. 15). Therefore, compound 34 represents a very potent non-peptidic conformationally constrained Smac mimetic, which has a binding affinity 29-fold more potent than the natural Smac AVPI peptide (SEQ ID NO:1).

Several other non-peptidic conformationally constrained Smac mimetics have been designed, synthesized and tested in the FP-based binding assays. Results are shown in Table 5.

TABLE 5

| Compound | Structure | $K_i$ (μM) |
|---|---|---|
| SH-67 (same as 20 in Table 3) | 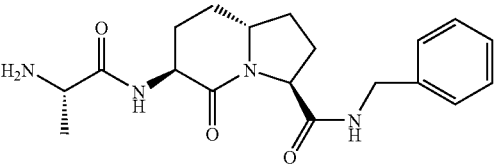 | >200 |

TABLE 5-continued

| Compound | Structure | $K_i$ (μM) |
|---|---|---|
| SH-68 (same as 19 in Table 3) | 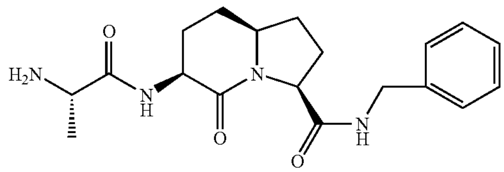 | 4.55 |
| SH-69 | 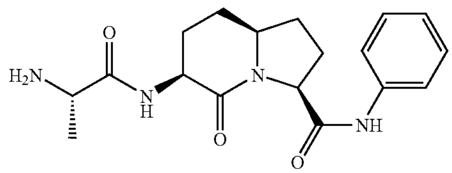 | >200 |
| SH-70 | 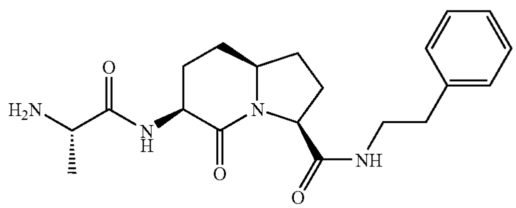 | 26.27 |
| SH-71 | 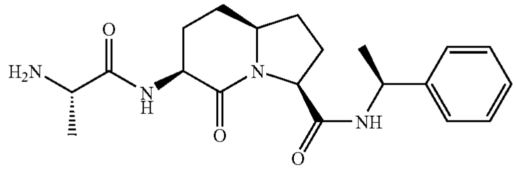 | >200 |
| SH-72 | 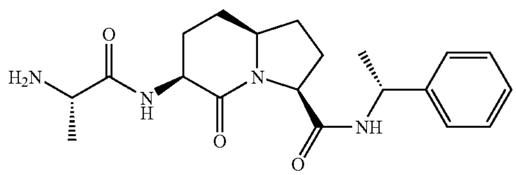 | 8.88 |
| SH-73 | 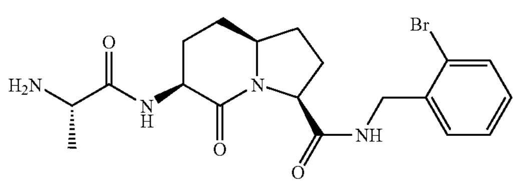 | 26.27 |
| SH-74 | 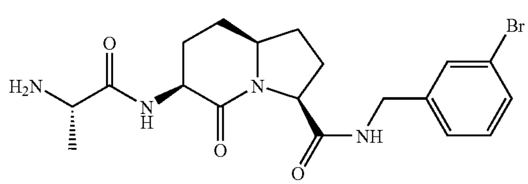 | 9.62 |
| SH-75 | 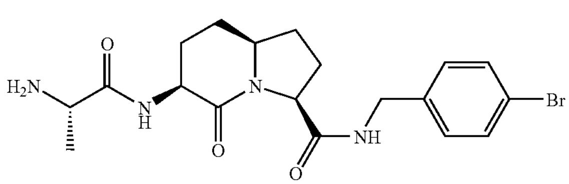 | 19.61 |

TABLE 5-continued

| Compound | Structure | $K_i$ (μM) |
|---|---|---|
| SH-76 | 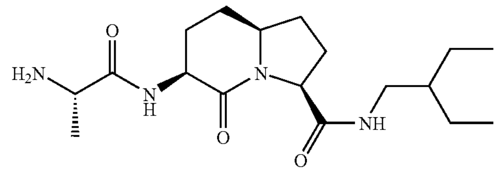 | >200 |
| SH-77 | 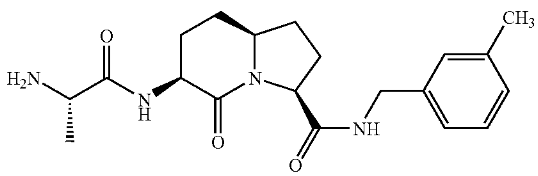 | 44.41 |
| SH-78 | 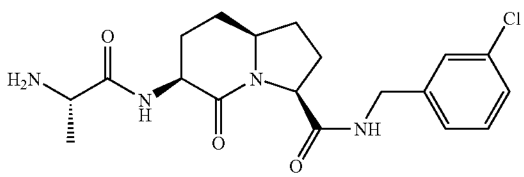 | 12.21 |
| SH-79 | 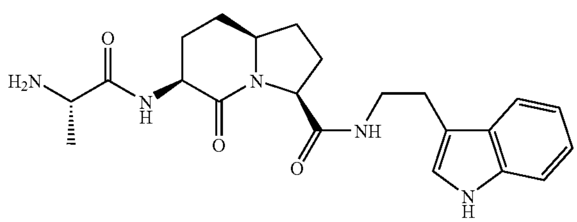 | >200 |
| SH-83 | 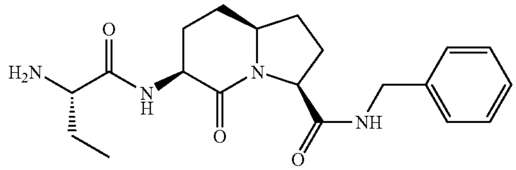 | 1.51 |
| SH-84 | 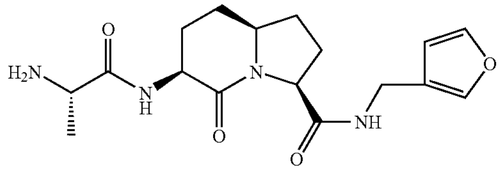 | 9.98 |
| SH-85 | 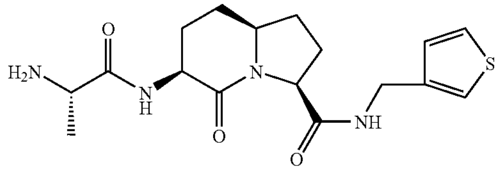 | 6.28 |
| SH-86 | 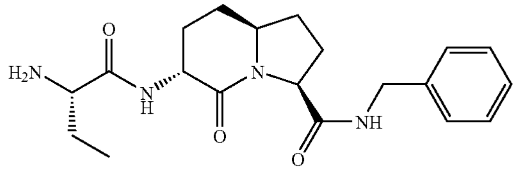 | 37.37 |

TABLE 5-continued

| Compound | Structure | $K_i$ (µM) |
|---|---|---|
| SH-92 | 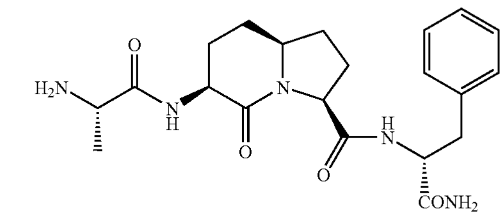 | 9.98 |
| SH-93 | 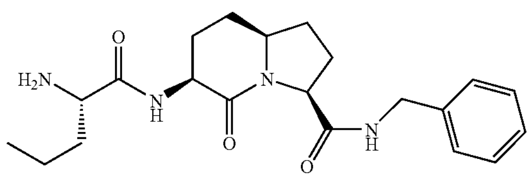 | >100 |
| SH-94 | 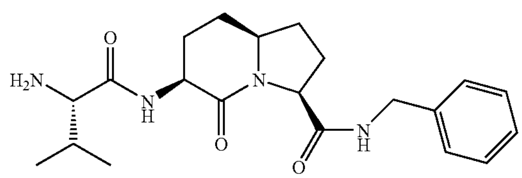 | 20.72 |
| SH-95 | 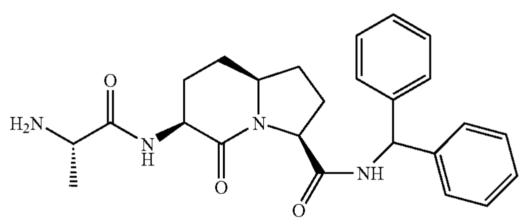 | 1.84 |
| SH-99 | 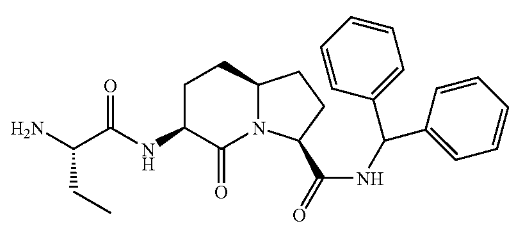 | 0.36 |
| SH-100 | 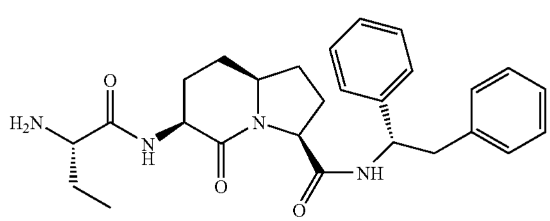 | 8.51 |
| SH-102 (same as 34 in Table 4) | 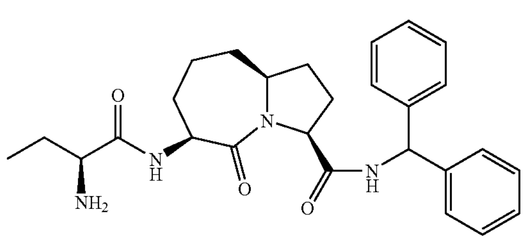 | 0.022 |

TABLE 5-continued

| Compound | Structure | $K_i$ (μM) |
|---|---|---|
| SH-104 | 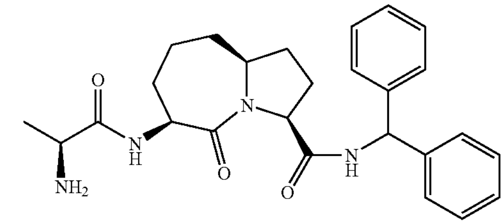 | 0.059 |
| SH-105 (same as 21 in Table 4) | 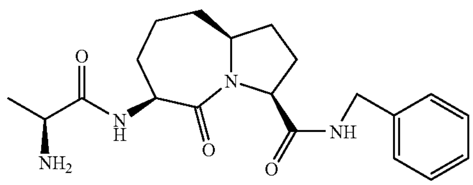 | 0.16 |
| SH-106 | 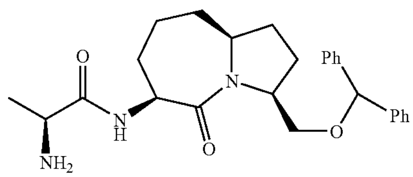 | 2.01 |
| SH-107 | 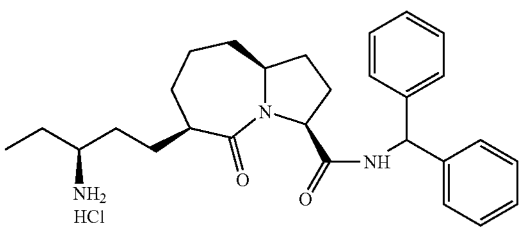 | >40 |

Example 8

Binding Affinities of Smac Mimetics with [6.3.0] Bicyclic Lactam System

Compounds with the [6.3.0] bicyclic lactam system was synthesized as described in Example 4. The compounds were tested in the FP-based binding assay and the binding data is provided in Table 6. The [6.3.0] compounds were found to have binding affinities as good as those seen for the [5.3.0] compounds.

TABLE 6

| Compound | Structure | $K_i$ (μM) |
|---|---|---|
| SH-109 | 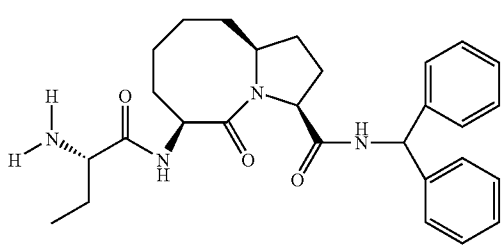 | 0.028 |

TABLE 6-continued
| Compound | Structure | $K_i$ (μM) |
|---|---|---|
| SH-113 | 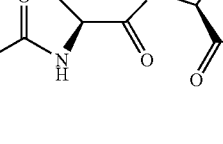 | 0.14 |
| SH-116 | 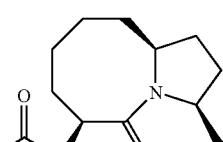 | 0.019 |
| SH-114 | 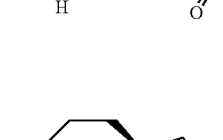 | 0.027 |
| SH-117 | 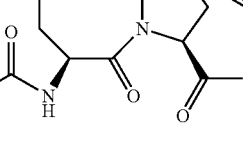 | 0.012 |
| SH-115 | 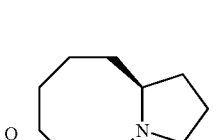 | 0.092 |
| SH-118 | 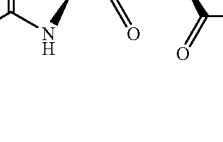 | 0.016 |

US 7,674,787 B2

TABLE 6-continued

| Compound | Structure | $K_i$ (µM) |
|---|---|---|
| SH-119 | 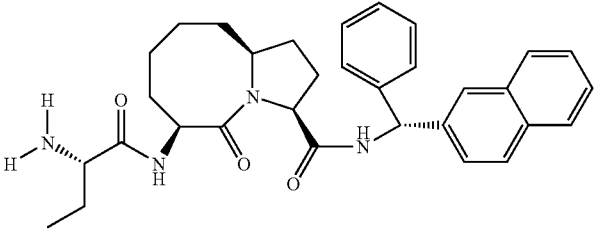 | 0.12 |
| SH-120 | 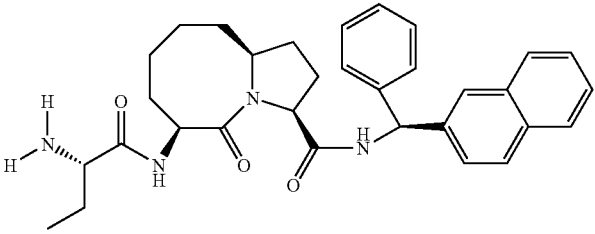 | 0.023 |
| SH-122 | 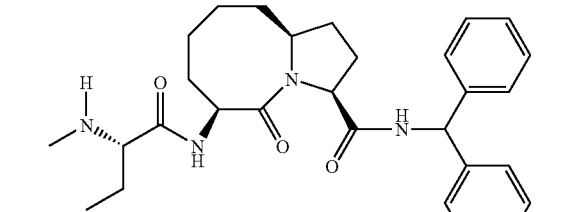 | 0.03 |
| SH-125 | 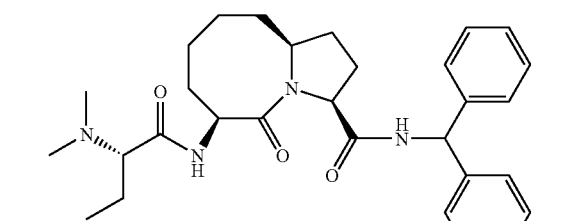 | 0.03 |
| SH-123 | 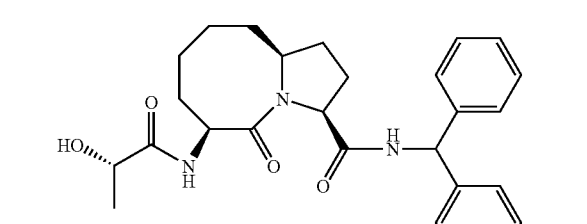 | >10 |

Example 9

Figure 16:
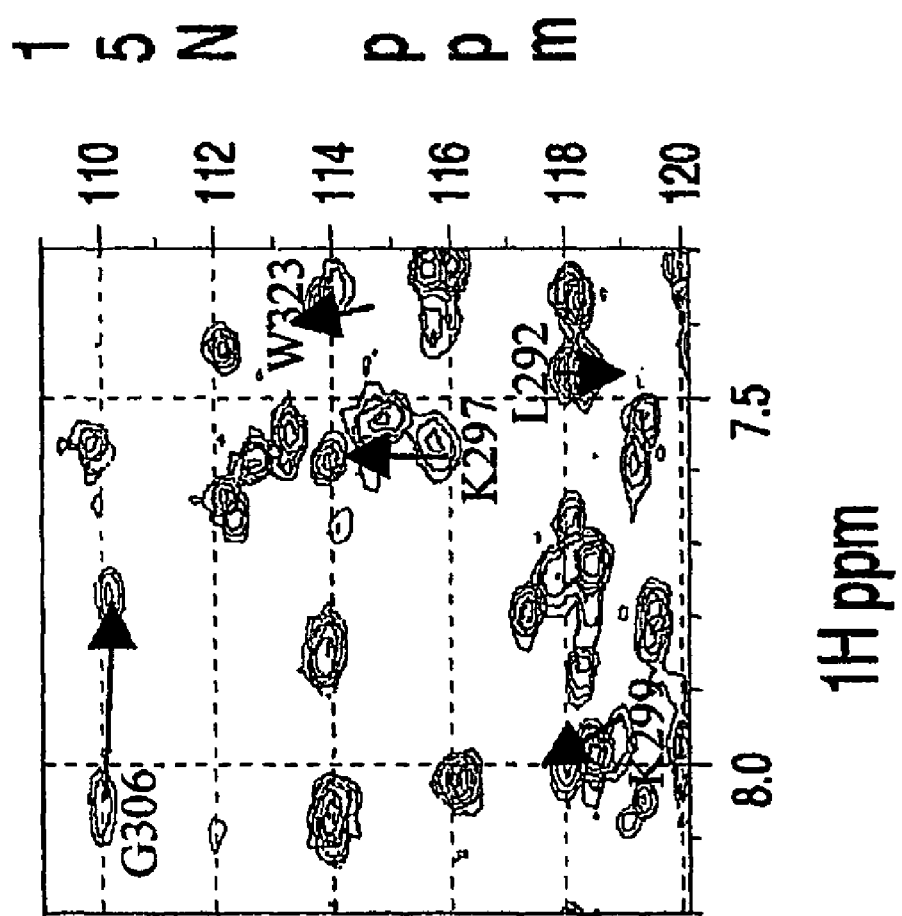
FIG. 16 shows the modeled complex of compound 34 in Table 4 and XIAP BIR3.

Conclusive Confirmation of the Binding of Compound 34 to XIAP by NMR Methods To conclusively confirm that compound 34 (Table 4, same as SH-102 in Table 5) binds to the binding groove of XIAP BIR3 where Smac binds, an analysis was performed using nuclear magnetic resonance (NMR) methods. The human XIAP BIR3 domain (residues 241-356) fused to His-tag was expressed from BL21 (DE3) cells in M9 medium containing $^{15}N$ ammonium chloride to uniformly label protein with $^{15}N$ and was purified. $^{15}N$ Heteronuclear Single Quantum Coherence Spectroscopy (HSQC) NMR spectra were recorded with samples containing 100 µM of the 15N protein in 50 mM Tris (pH 7.2), 50 µM $ZnCl_2$, 1 mM DTT with 100 µM of compound 34 or without it at 30° C. Overlaying of the two $^{15}N$ HSQC spectra of the BIR3 domain of human XIAP with compound 34 and without showed that compound 34 bound to the protein and caused induced chemical shifts in several residues in XIAP BIR3 (FIG. 16). In addition, some new peaks appeared in the spectrum with compound 34 (FIG. 16), suggesting that a flexible loop in XIAP BIR3 becomes structured upon contact with compound 34 as observed in the complex structure of XIAP BIR3 and Smac (Sun et al., *J. Biol. Chem.* 275:33777 (2000)).

To identify which residues in XIAP BIR3 were affected by compound 34, $^{13}C$ and $^{15}N$ double labeled XIAP BIR3 was prepared and 3D NMR triple resonance experiments were performed to make backbone atom resonance assignments. HNCA, HNCACB, HN(CO)CBCA, HNCO, TOCSY-HSQC, C(CO)NH and the published results (Sun et al., *J. Biol. Chem.* 275:33777 (2000)) were used to nearly complete the backbone assignments, except for the two flexible loops (residues 276-280 and 308-314). Based upon the nearly complete backbone assignments of XIAP BIR3, it was found that residues G306, W323, K297, L292, and K299 are affected by compound 34 (FIG. 16). Moreover, these residues were also found to be affected by the Smac AVPI peptide (SEQ ID NO:1) in the NMR analysis. Based upon the experimental complex structures of Smac/XIAP BIR3 (FIG. 1), these residues in XIAP BIR3 that are affected by compound 34 and Smac AVPI peptide (SEQ ID NO:1) are in direct contact with the Smac peptide. Using the same methods, it was also determined that compound 32 caused induced chemical shifts to the same set of residues in XIAP BIR3 as those caused by compound 34 and Smac AVPI peptide (SEQ ID NO:1), indicating that these Smac mimetics also bind to the same binding groove as compound 34 and Smac AVPI peptide (SEQ ID NO:1). Taken together, the NMR experimental results conclusively confirm that compounds 32 and 34 and other Smac mimetics bind to the binding groove in XIAP BIR3 where Smac binds. The experiments also showed that Smac peptide and the designed mimetics do not unfold the protein.

Example 10

Expression of IAP Family Proteins in Cancer Cells and Normal Cells

Figure 17:
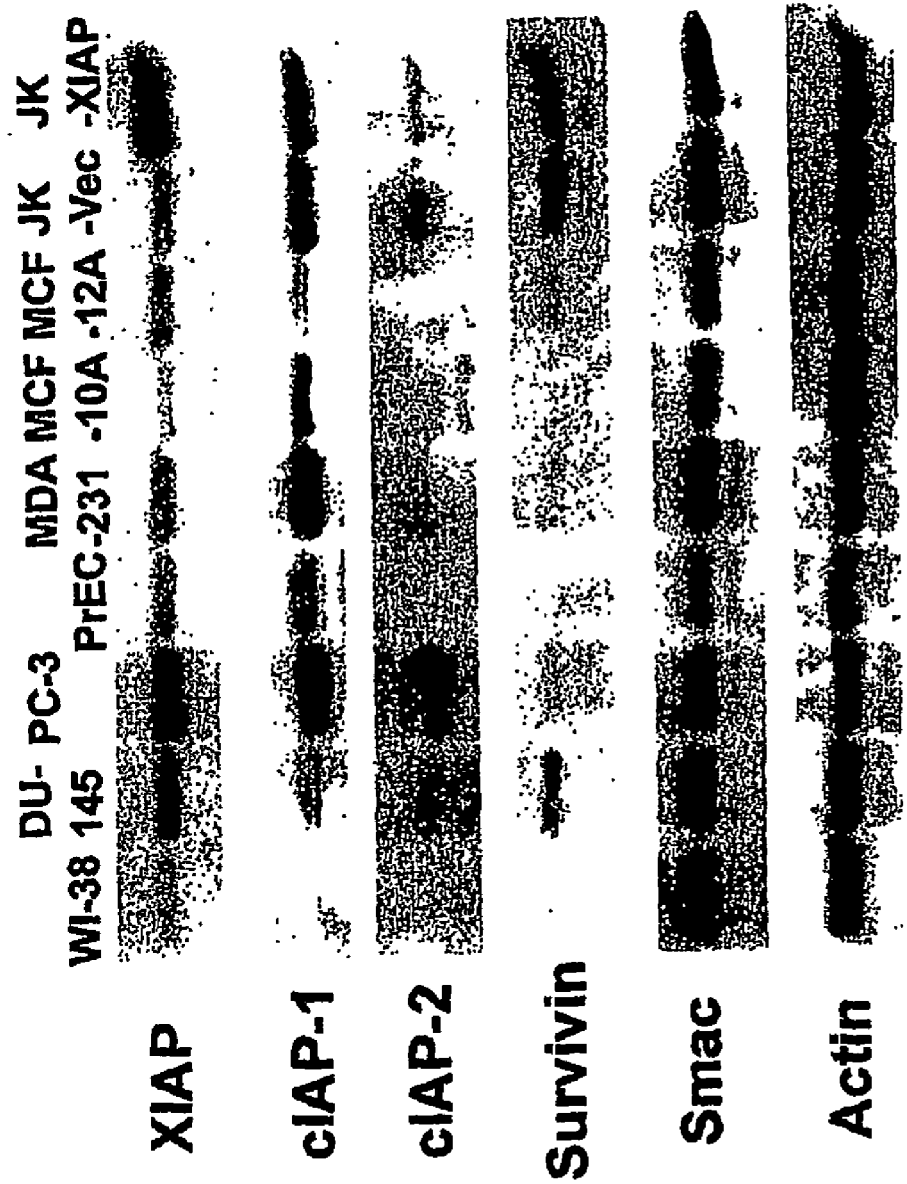
FIG. 17 shows Western blot analysis of XIAP, cIAP-1/2, survivin, and Smac in various cell lines.

To study the activity and specificity of the designed Smac mimetics, Western blot analysis of XIAP, cIAP-1/2, survivin and Smac proteins was performed in several human cancer cell lines and normal cells (FIG. 17).

The results show that human prostate cancer PC-3 cells have high levels of MAP and cIAP-1/2 and a low level of survivin; human breast cancer MDA-MB-231 cells have a high level of cIAP-1, a medium level of XIAP, and low levels of cIAP-2 and survivin; and human prostate cancer DU-145 cells have a high level of XIAP and medium levels of cIAP-1/2 and survivin.

Normal human fibroblast WI-38 cells have low levels of XIAP, cIAP-1/2 and survivin; normal-prostate epithelial cells (PrEC) have a detectable level of XIAP but much lower than PC-3 and DU-145 cells, a medium level of cIAP-1 and very low levels of cIAP-2 and survivin; and normal human breast epithelial cell lines MCF-10A and MCF-12A have detectable levels of XIAP but much lower than DU-145 and PC-3, have detectable levels of cIAP-1 but much lower than PC-3 and MDA-231, and very low levels of cIAP-2 and survivin.

Jurkat cells have low levels of MAP and cIAP-2 and medium levels of cIAP-1 and survivin. As expected, Jurkat cells transfected with MAP protein have a very high level of XIAP, while other IAP proteins are unchanged as compared to the parental cell line. The level of Smac protein appears to be the same among the cancer cells and normal cells examined here.

Example 11

Smac Mimetics Enhance Cisplatin-Induced Apoptosis in Prostate Cancer PC-3 Cells

Previous studies using short Smac peptides fused to a carrier peptide have convincingly demonstrated that cell-permeable Smac peptides were able to increase the apoptosis of cancer cells induced by a variety of chemotherapeutic agents in glioma, melanoma, breast, and non-small cell lung cancer cells (Fulda et al., *Nature Med.* 8:808 (2002); Arnt et al., *J. Biol. Chem.* 277:44236 (2002); Yang et al., *Cancer Res.* 63:831 (2003)). Several characteristics were common among these studies. These cell-permeable Smac peptides by themselves have little effect in inducing apoptosis in cancer cells. A fairly high concentration of the peptides must be used (50-100 µM) in order to significantly potentiate the activity of chemotherapeutic drugs in apoptosis induction.

The basic premise of the present invention is that potent non-peptidic Smac mimetics are more effective to increase apoptosis of cancer cells induced by chemotherapeutic drugs than cell-permeable Smac peptides. The previous examples disclose quite potent non-peptidic Smac mimetics compounds 33 and 34 with binding affinities at least 10-fold better than the Smac AVPI peptide (SEQ ID NO:1). SH-97, a peptido-mimetic in which the side chain of alanine has been replaced with an ethyl group and the isoleucine has been replaced with a diphenylmethyl group, was used to test the basic premise. Of note, SH-97 still has two natural amino acids (valine and proline) and one natural peptide bond. For control compounds, a previously published cell-permeable Smac peptide (Smac8-C) (Arnt et al., *J. Biol. Chem.* 277: 44236 (2002)) was used as a positive control, Smac peptide (AVPIAQKS) (SEQ ID NO:6) without a carrier peptide was used as a negative control (Smac-8), and an inactive compound (SH-93, Table 5) as another negative control. The experiment used PC-3 cells which express high levels of XIAP and cIAP-1/2 proteins and cisplatin (CDDP) as the chemotherapeutic drug. CDDP is a DNA damaging agent and can effectively induce apoptosis in PC-3 cells and is also a clinically used chemotherapeutic drug for prostate cancer.

Figure 18A:
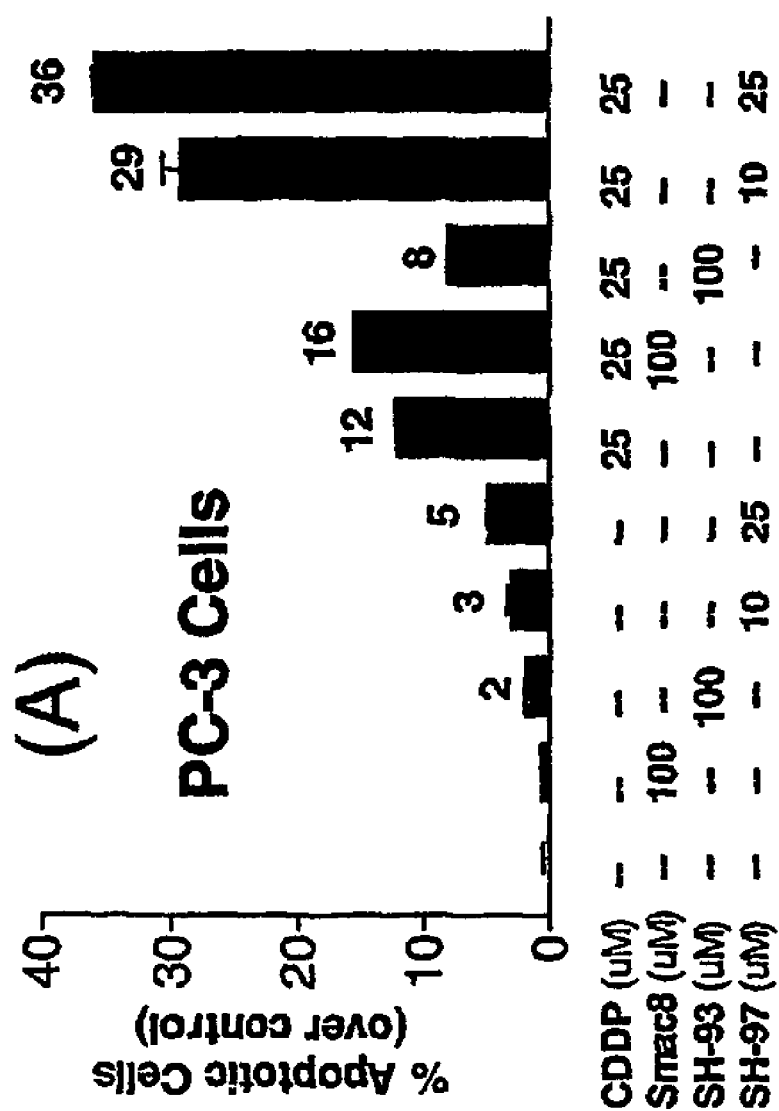
FIGS. 18A and 18B show the induction of apoptosis in PC-3 cells in response to cisplatin (CDDP) and Smac mimetics.
Figure 18B:
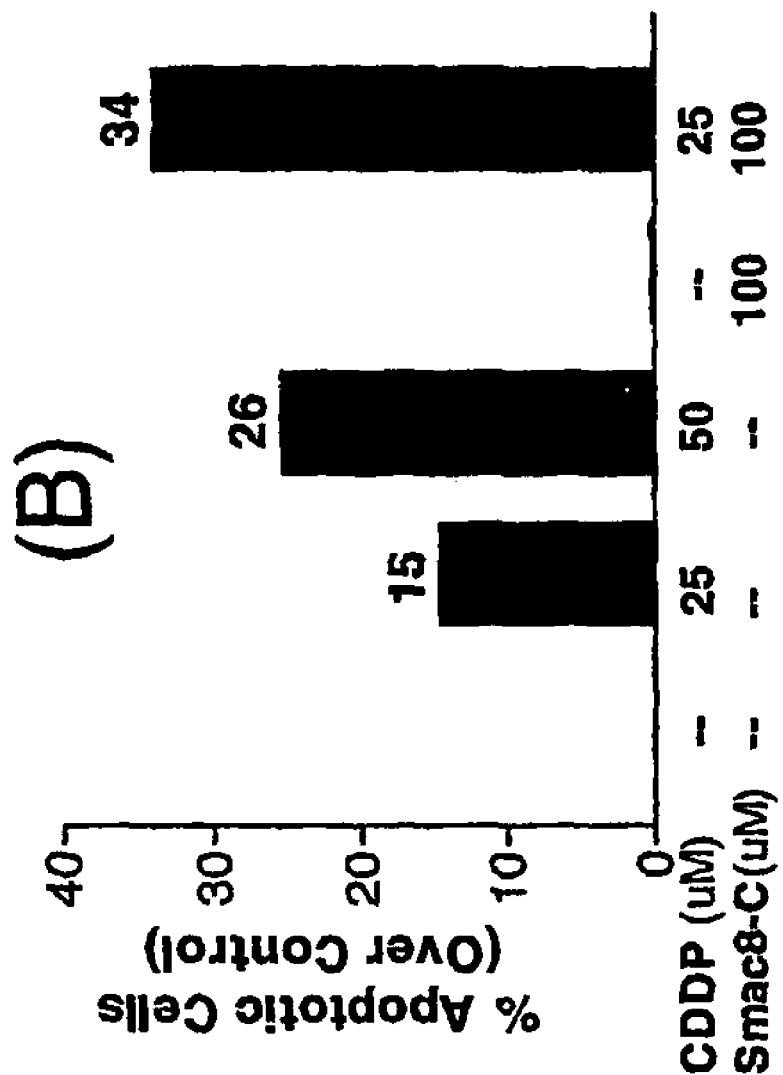

PC-3 cells were treated with CDDP, Smac peptides and mimetics alone or in combination for 42 hours and apoptosis was analyzed by Annexin V-FITC staining. Consistent with previous studies using cell-permeable Smac peptides, SH-97 up to 50 µM did not induce significantly more apoptosis as compared to untreated cancer cells, while 25 µM CDDP induced 12-15% of cancer cells to undergo apoptosis as compared to control cells (FIG. 18A). Combination of 25 µM CDDP and 10 µM or 25 µM SH-97 induced 29.3%±1.9% and 35.8%±0.4% apoptosis over control cells, respectively (FIG. 18A). Consistent with the published results that the cell-permeable Smac peptide increased apoptosis of chemotherapeutic drugs in a variety of cancer cells with high levels of IAP proteins, combination of 25 µM CDDP and 100 µM Smac8-C increased the apoptosis to 34% over control cells, while Smac8-C by itself had no significant effect FIG. 18B).

Similar experiments were performed with SH-102 (Table 5). PC-3 cells in 6-well plates were treated with SH-102 and CDDP, alone or in combination, for 42 hours. Cells were collected and stained with Annexin V-FITC and propidium iodide. The fluorescence of Annexin V-FITC and propidium iodide of individual cells was analyzed by flow cytometry.

Figure 19:
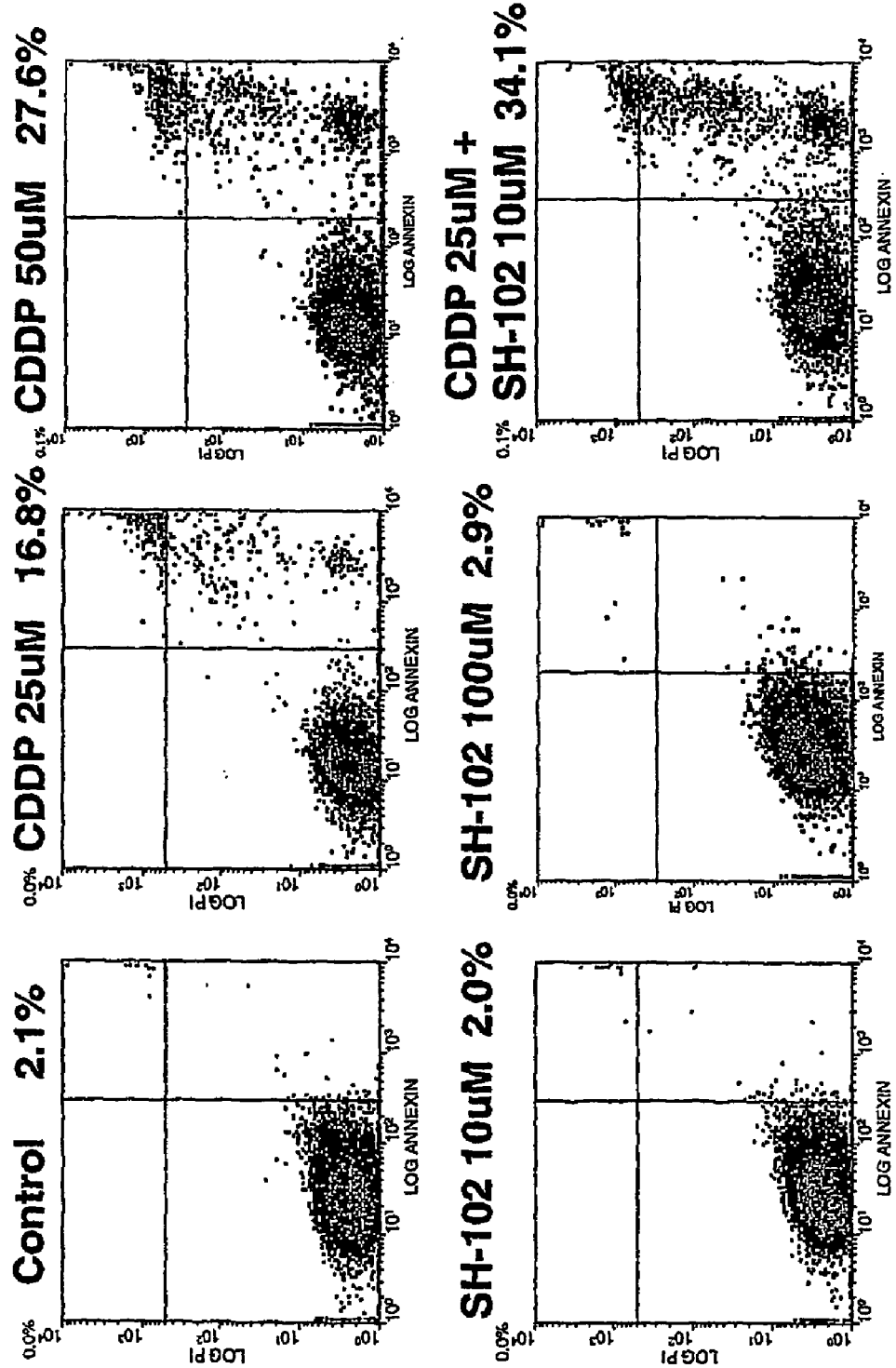
FIG. 19 shows the induction of apoptosis in PC-3 cells in response to CDDP and Smac mimetics.
Figure 20:
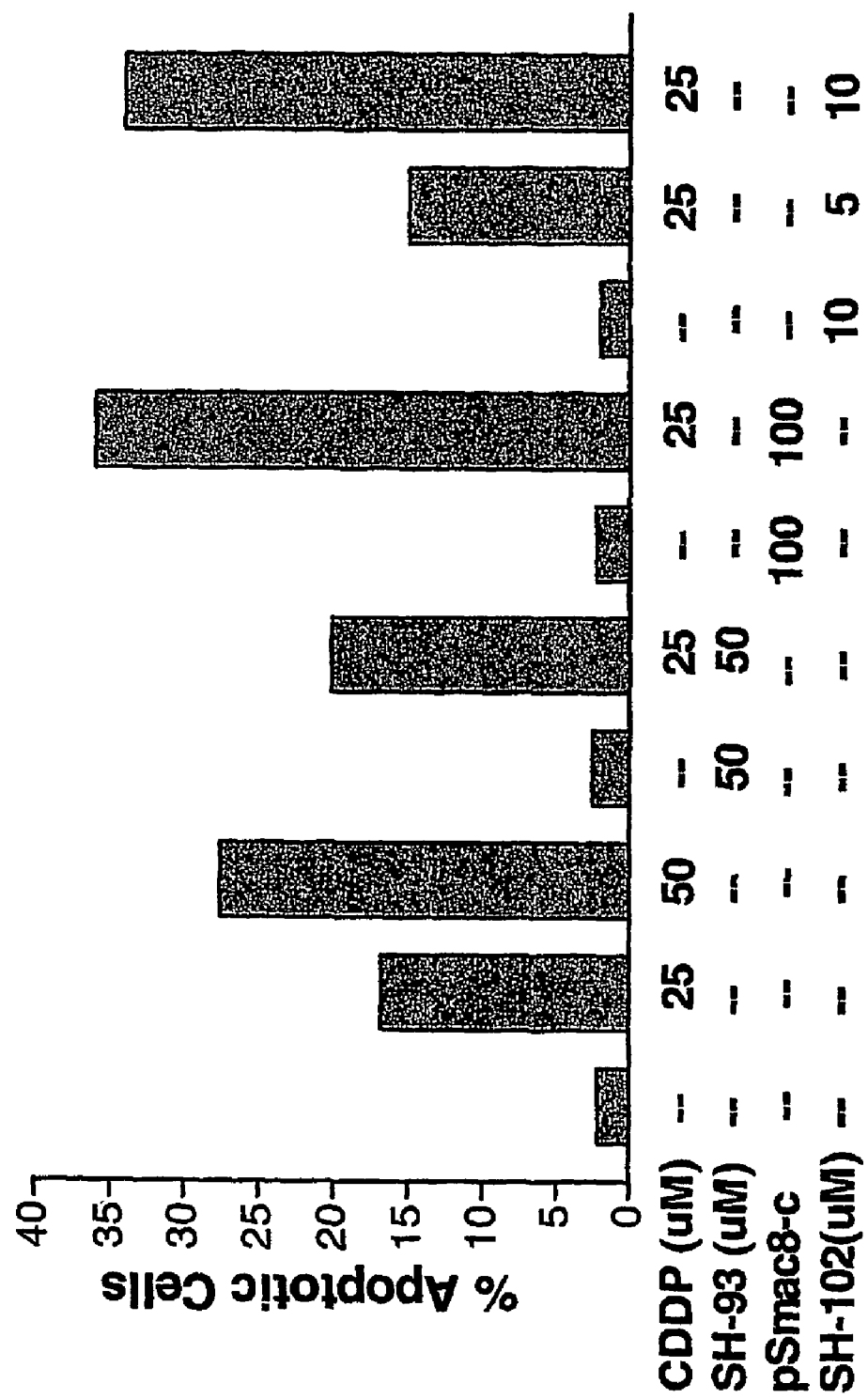
FIG. 20 shows the induction of apoptosis in PC-3 cells in response to CDDP and Smac mimetics.

SH-102 up to 100 µM did not induce significantly more apoptosis as compared to untreated cancer cells, while 25 µM and 50 µM CDDP induced about 15% and 25% of cancer cells to undergo apoptosis as compared to control cells, respectively (FIG. 19). Combination of 25 µM CDDP and 10 µM SH-102 induced 32% apoptosis over control cells (FIG. 19). As shown above, combination of 25 µM CDDP and 100 µM Smac8-C increased the apoptosis to about 34% over control cells, while Smac8-C by itself had no significant effect (FIG. 20).

Figure 21:
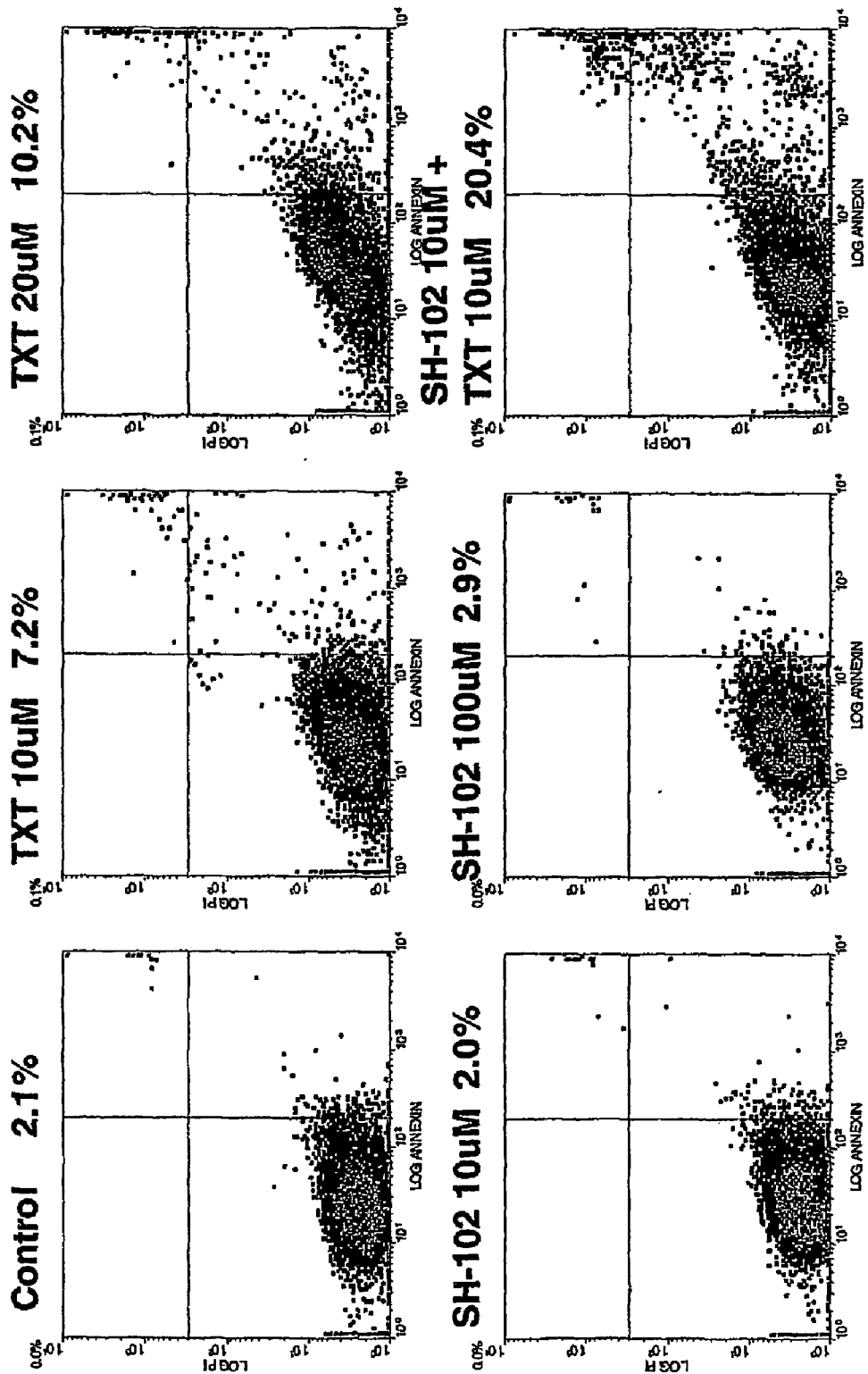
FIG. 21 shows the induction of apoptosis in PC-3 cells in response to TAXOTERE and Smac mimetics.

The same experiment was performed using TAXOTERE (docetaxel), another cancer chemotherapeutic drug. PC-3 cells in 6-well plates were treated with SH-102 and TAXOTERE, alone or in combination, for 42 hours. Cells were collected and stained with Annexin V-FITC and propidium iodide. The fluorescence of Annexin V-FITC and propidium iodide of individual cells was analyzed by flow cytometry. SH-102 up to 100 µM did not induce significantly more apoptosis as compared to untreated cancer cells, while 10 µM and 20 µM TAXOTERE induced about 5% and 8% of cancer cells to undergo apoptosis as compared to control cells, respectively (FIG. 21). Combination of 10 µM TAXOTERE and 10 µM SH-102 induced about 18% apoptosis over control cells (FIG. 21).

Figure 22:
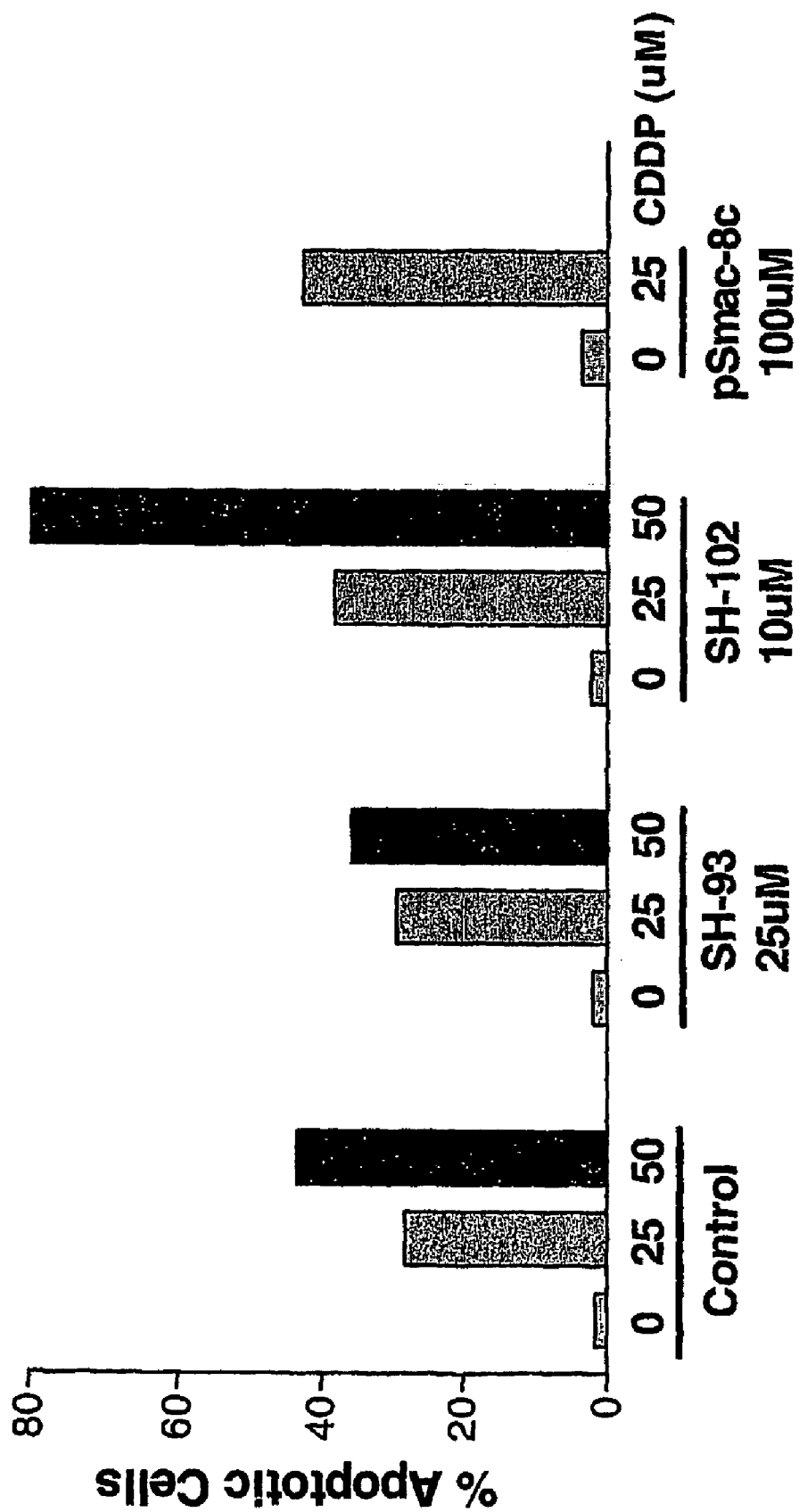
FIG. 22 shows the induction of apoptosis in MDA-231 cells in response to CDDP and Smac mimetics.

Similar experiments were performed using the breast cancer cell line MDA-231. MDA-231 cells in 6-well plates were treated with SH-102 and CDDP, alone or in combination, for 42 hours. Cells were collected and stained with Annexin V-FITC and propidium iodide. The fluorescence of Annexin V-FITC and propidium iodide of individual cells was analyzed by flow cytometry. 25 µM and 50 µM CDDP induced about 25% and 42% of MDA-231 cells to undergo apoptosis as compared to control cells, respectively (FIG. 22). Combination of 25 and 50 µM CDDP with 25 µM SH-93 had no significant effect over control cells. Combination of 25 and 50 µM CDDP and 10 µM SH-102 induced about 35% and 75% apoptosis over control cells, respectively (FIG. 22). The ability of 10 µM SH-102 to sensitize cells to CDDP was as great as that of 100 µM pSmac8-C (FIG. 22).

Taken together, the results show that potent Smac mimetics are effective to potentiate the activity of CDDP and TAXOTERE in inducing apoptosis in PC-3 cells and MDA-231 cells. Additionally, the Smac mimetics of the present invention appear to be more potent than the Smac peptide fused to a carrier peptide (Smac8-C) used in a previous study, while Smac peptide without the carrier peptide or an inactive Smac mimetic (SH-93) is unable to potentiate the activity of CDDP in inducing apoptosis in PC-3 cells or MDA-231 cells.

Example 12

SH-102 Overcomes the Protective Effect of XIAP

To investigate the effect Smac mimetics have on cells having elevated levels of XIAP (as many cancers do), Jurkat T cells were stably transfected with a vector expressing human XIAP or a control vector. Jurkat cells transfected with control vector (Jurkat-Vec) have a very low level of XIAP protein as analyzed by Western blot, while Jurkat cells stably transfected with vector encoding human XIAP (Jurkat-XIAP) have a very high level of XIAP protein.

Figure 23:
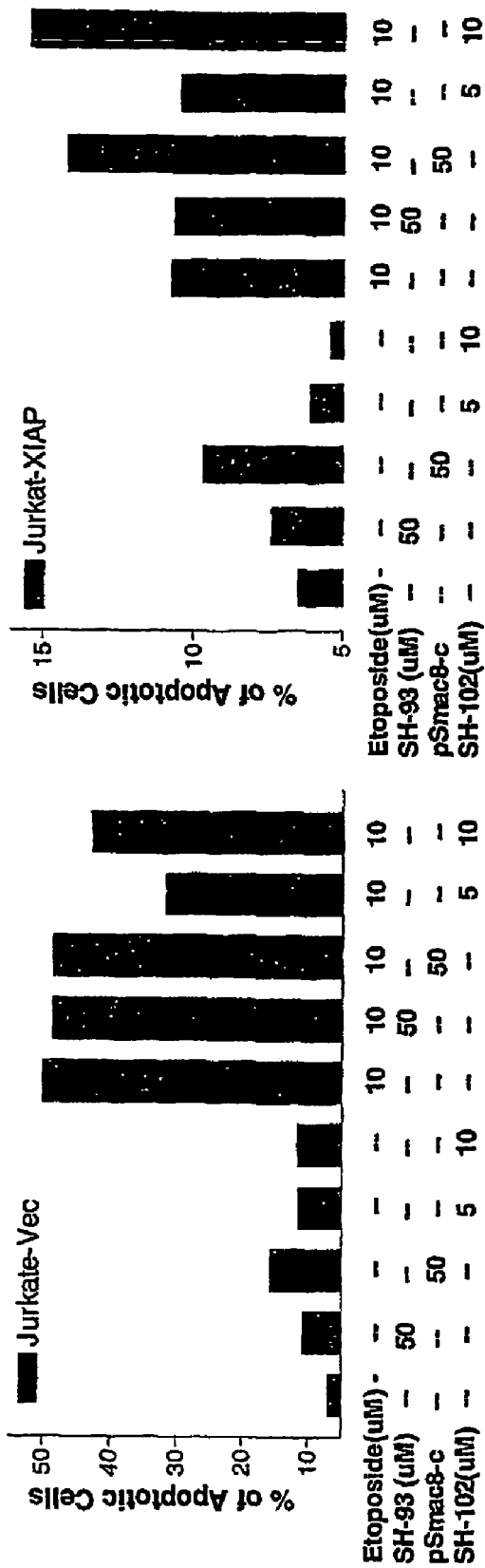
FIG. 23 shows the induction of apoptosis in Jurkat cells overexpressing XIAP in response to etoposide and Smac mimetics.

The two stably transfected cell lines were treated with the cancer chemotherapeutic drug etoposide and SH-102, alone and in combination, for 15 hours. Cells were collected and fixed in 70% ethanol on ice. After centrifugation, cells were stained in 50 µg/ml propidium iodide and 0.1 µg/ml RNase A, and analyzed by flow cytometry. Each sample had at least 5000 cells scanned. Data were analyzed to calculate the percentage of sub-G1 cells (apoptotic cells) using CellQuest software (Becton Dickinson). Jurkat-XIAP cells were more resistant to 10 µM etoposide (about 10% apoptotic cells) than Jurkat-Vec cells (about 50% apoptotic cells) (FIG. 23). 10 µM SH-102 in combination with etoposide induced about 15% apoptosis, indicating that the protective effect of XIAP to drug-induced apoptosis can be overcome by a Smac mimetic (FIG. 23). 10 µM SH-102 was at least as effective as 50 µM Smac8-C (FIG. 23).

Figure 24:
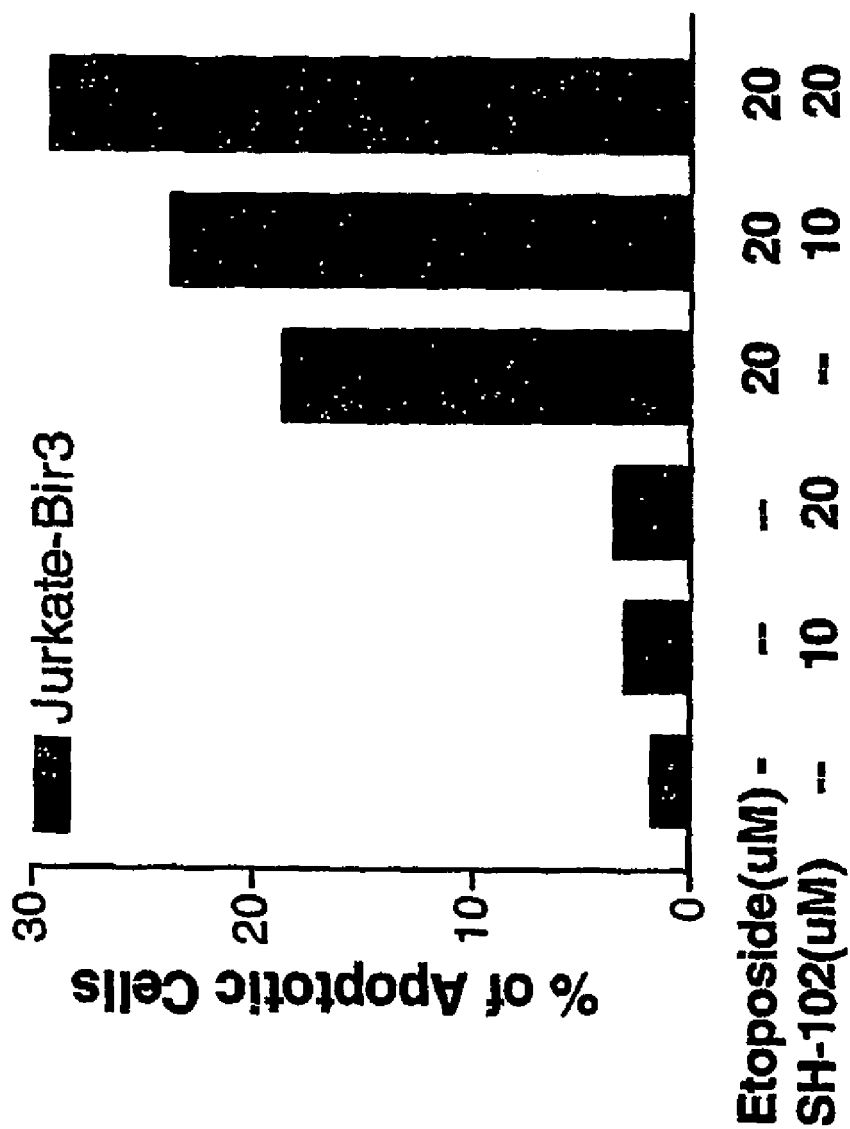
FIG. 24 shows the induction of apoptosis in Jurkat cells overexpressing XIAP-Bir3 in response to etoposide and Smac mimetics.

Another stably transfected Jurkat cell line expressing human XIAP in which the Bir1 and Bir2 domains were deleted was established (Jurkat-Bir3). Expression of the deleted XIAP protein protected cells from etoposide-induced apoptosis. While 20 µM etoposide induced about 18% apoptosis in the Jurkat-Bir3 cells, the combination of etoposide with 10 or 20 µM SH-102 caused about 25 and 30% apoptosis, respectively (FIG. 24), indicating that SH-102 can overcome the protective effect of XIAP-Bir3 to drug-induced apoptosis and also showing that the Bir3 domain is involved in the cellular activity of SH-102.

Example 13

SH-97 Sensitizes PC-3 Cells to X-Ray Irradiation in a Clonogenic Assay

Overexpression of XIAP and other IAP proteins in cancer cells has been shown to inhibit apoptosis induced not only by chemotherapeutic agents but also by radiation (Holcik et al., *Oncogene* 19:4174 (2000)). Therefore, it was predicted that treatment of PC-3 cells with a potent and cell-permeable Smac mimetic such as SH-97 will sensitize PC-3 cells to X-ray radiation by directly overcoming the protective effects of IAP proteins to cancer cells.

Figure 25:
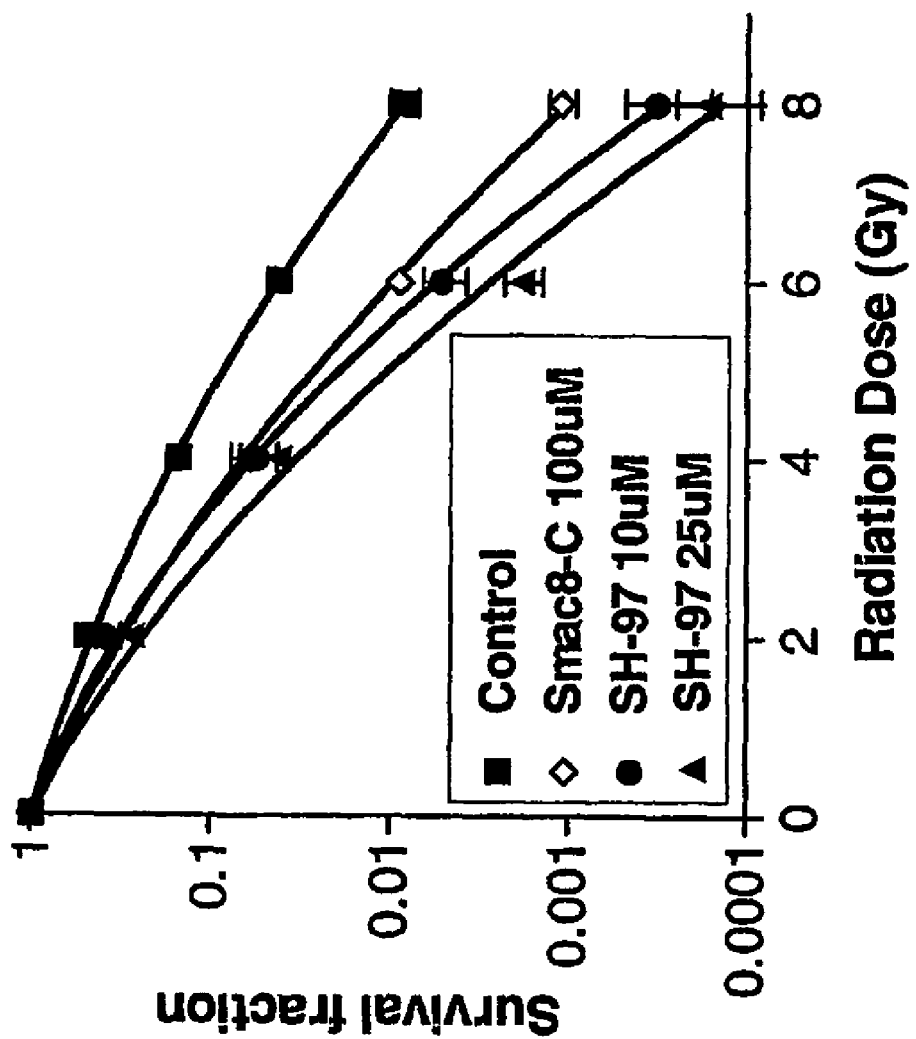
FIG. 25 shows the inhibition of colony growth in response to radiation and Smac mimetics.

To test this prediction, PC-3 cells were treated in 6-well plates with SH-97 and X-ray radiation alone and in combination using a standard clonogenic assay. The cell-permeable Smac peptide (Smac8-C) was again used as the positive control. After 10 days of culture, the plates were stained with crystal violet and the colonies with over 50 cells were counted with a ColCount colony counter. The cell survival curves were plotted with linear-quadratic curve fitting (FIG. 25). Consistent with the apoptosis experiments, SH-97 or Smac8-C by itself had no significant effect. Treatment of PC-3 cells with 10 and 25 µM of SH-97 or with 100 µM of Smac8-C significantly increased the activity of the radiation. As can be seen, at 6 Gy dose of radiation, 10 and 25 µM of SH-97 resulted in more than 10-fold reduction of colony formation as compared to radiation alone. At 8 Gy of radiation, 10 and 25 µM of SH-97 resulted in 40- and 50-fold reduction of colony formation as compared to radiation alone. Consistent with results obtained from the above mentioned combination experiment of SH-97 with CDDP, 10 µM SH-97 also appears to be more effective than 100 µM of the cell-permeable Smac peptide Smac8-C at both 6 and 8 Gy radiation doses. Hence, the preliminary results on SH-97 in both apoptosis and colony formation experiments provide evidence to support the basic premise that a potent cell-permeable peptido-mimetic or non-peptidic peptide-mimetic will be more effective than cell-permeable Smac peptides to overcome apoptosis resistance of cancer cells with high levels of XIAP and other IAP proteins to chemotherapeutic drugs and radiation.

Example 14

Inhibition of Cell Growth by SH-102 in Human Cancer Cells

Figure 26A:
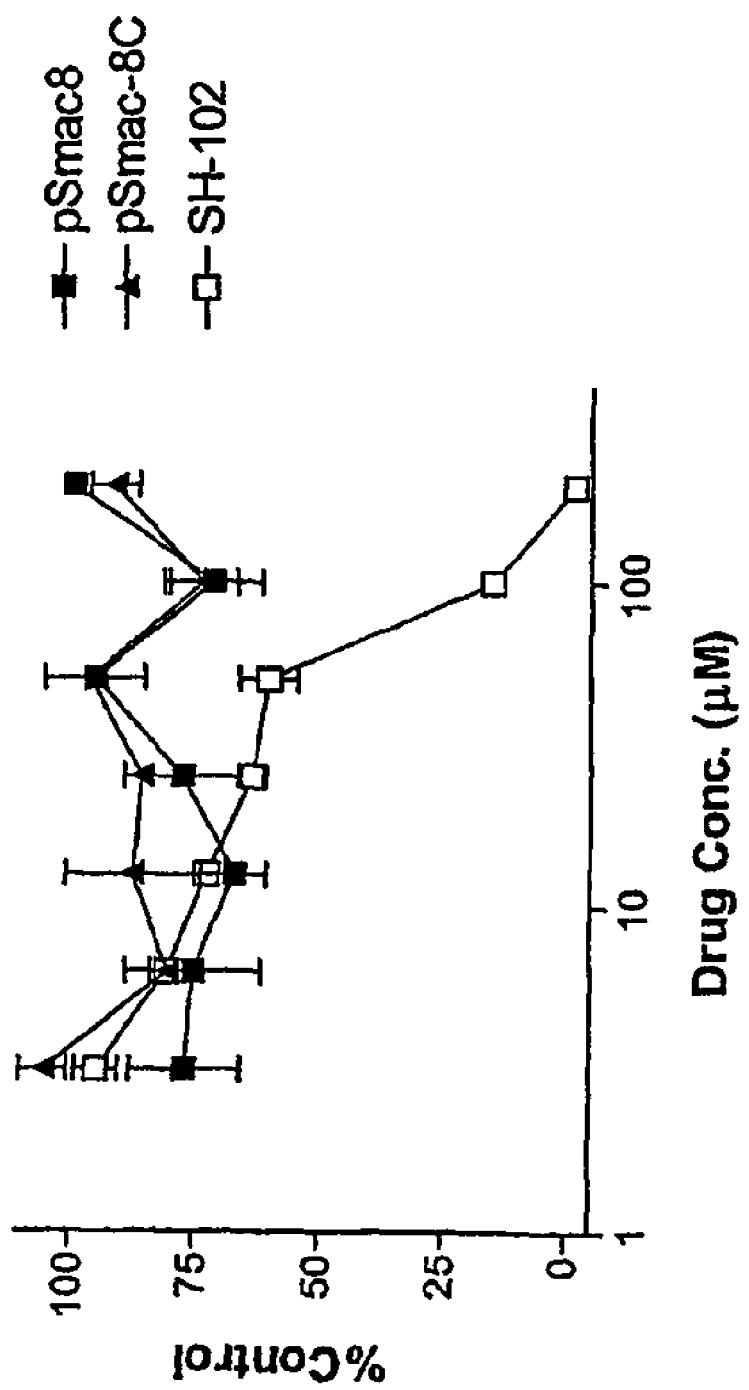
FIGS. 26A-26C show the inhibition of growth of breast cancer cells in response to Smac mimetics.
Figure 26B:
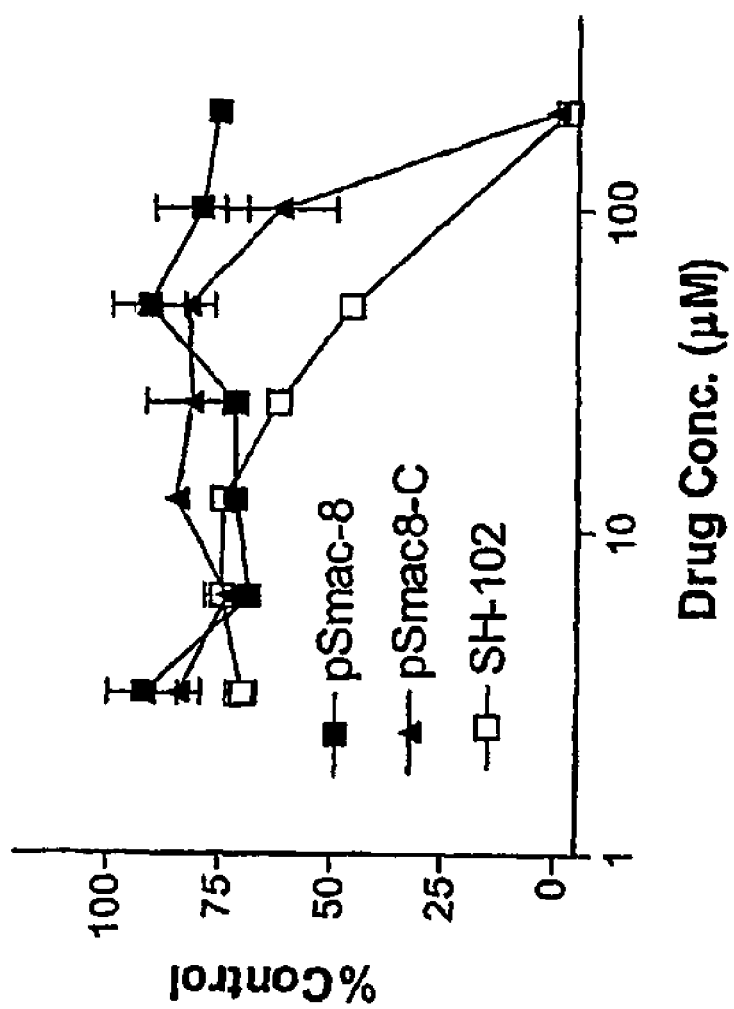
Figure 26C:
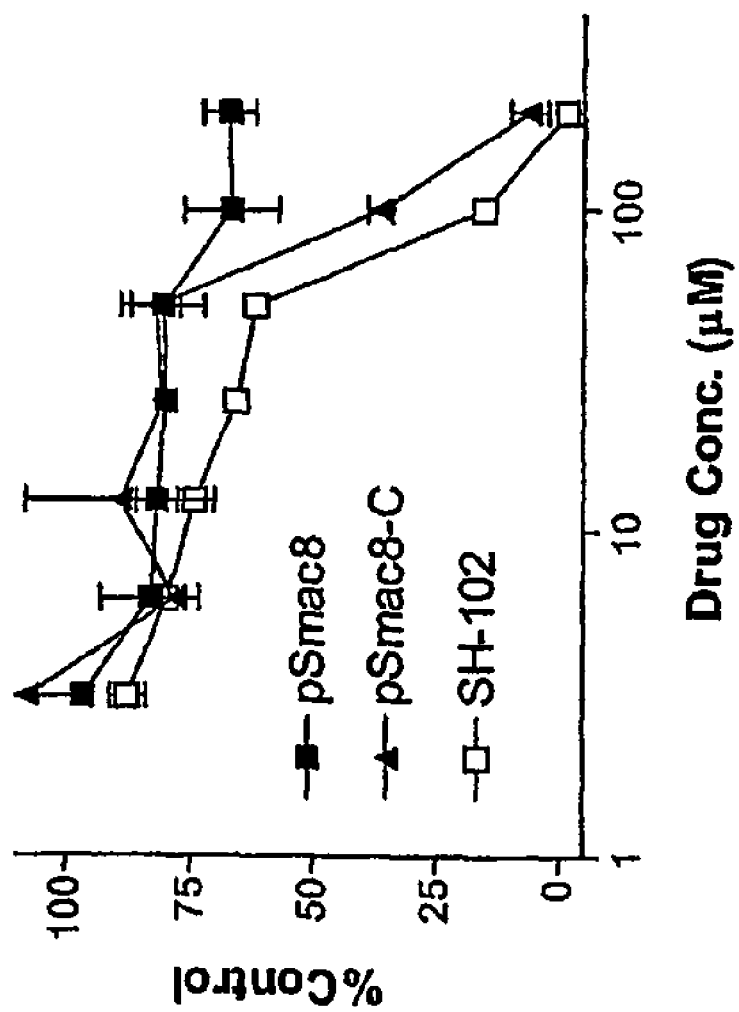
Figure 27:
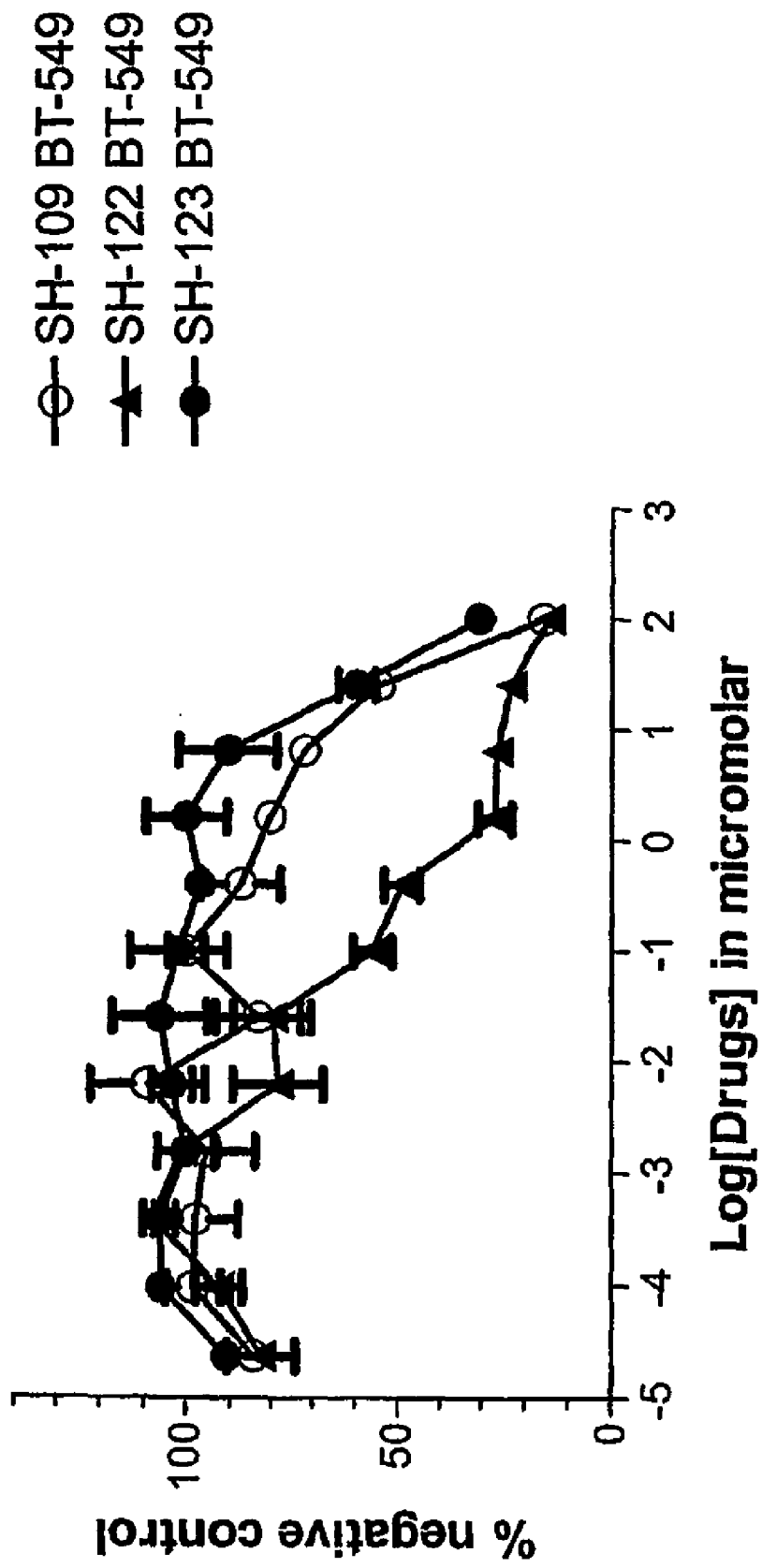
FIG. 27 shows the inhibition of growth of breast cancer cells in response to Smac mimetics.
Figure 28:
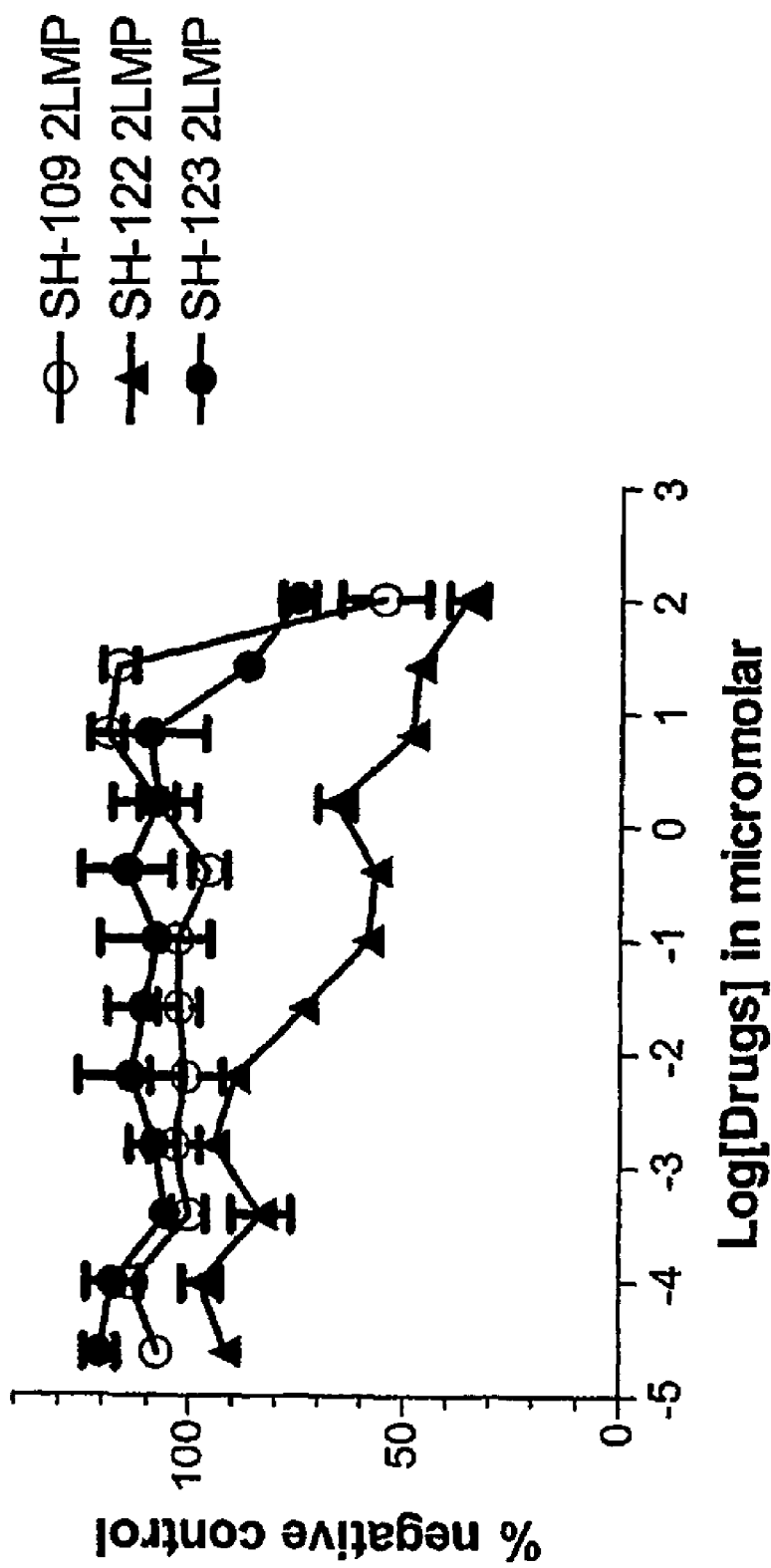
FIG. 28 shows the inhibition of growth of breast cancer cells in response to Smac mimetics.
Figure 29:
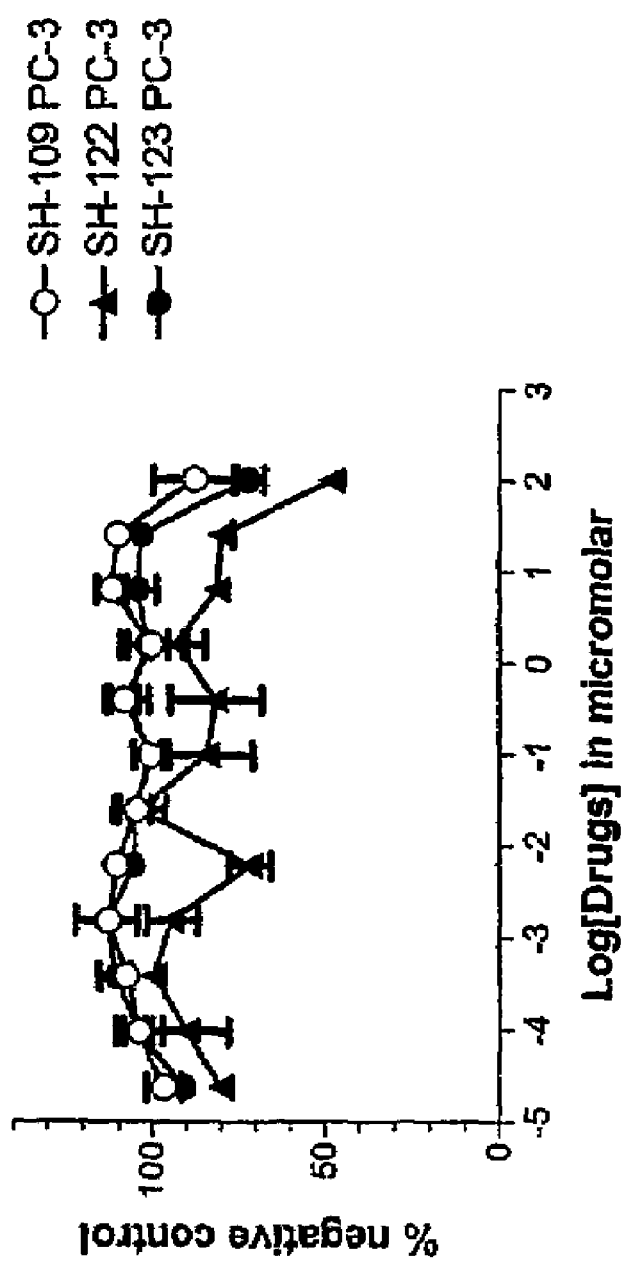
FIG. 29 shows the inhibition of growth of prostate cancer cells in response to Smac mimetics.
Figure 30:
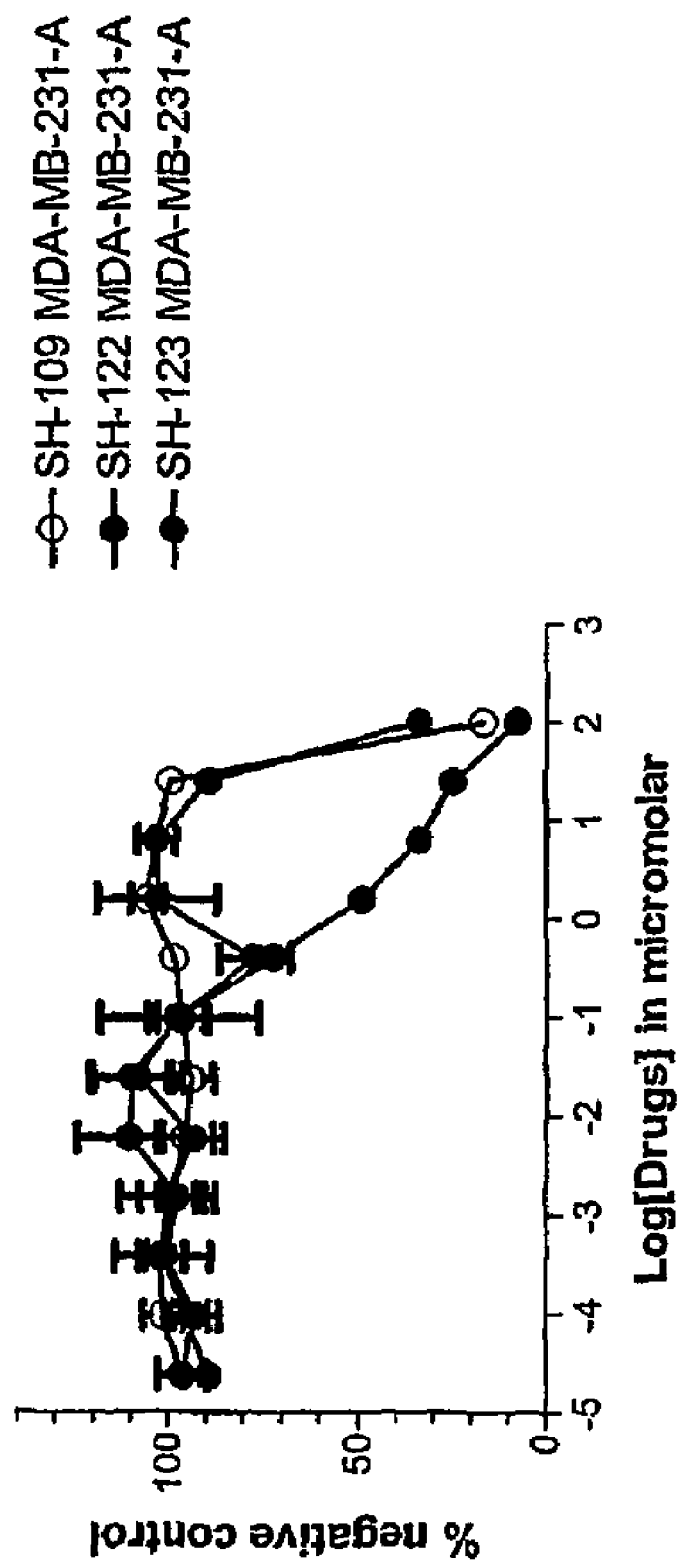
FIG. 30 shows the inhibition of growth of breast cancer cells in response to Smac mimetics.

To test the effect of Smac mimetics by themselves in inhibition of cell growth in human cancer cells, SH-102 was administered to three different breast cancer cell lines. MDA-435, MDA-468, and T47D cells were seeded in 96-well plates with increasing concentrations of SH-102, Smac8, or Smac8-C. The cells were then incubated at 37° C. with 5% $CO_2$ for 5 days, followed by detection of cell viability with WST-8 (10% Dojindo solution in IMEM with 10% FCS). OD values at 450 nm with reference at 650 nm were read approximately 3 hours later. Untreated cells were used as 100% growth. SH-102 inhibited the cell growth of each of the cell lines, with an $IC_{50}$ in the range of about 30-70 μM (FIGS. 26A-26C). In contrast, a cell-permeable Smac peptide (Smac8-C) was less potent than SH-102 in inhibiting cell growth in all these cell lines. (FIGS. 26A-26C). A natural Smac peptide derived from Smac protein sequence without a carrier peptide (Smac8) was essentially ineffective in all three cells (FIGS. 26A-26C). These data indicate that Smac mimetics are capable of inhibiting cell growth in human cancer cells.

Example 15

Inhibition of Cell growth by SH-109, SH-122 and SH-123 in Human Cancer Cells

Figure 31:
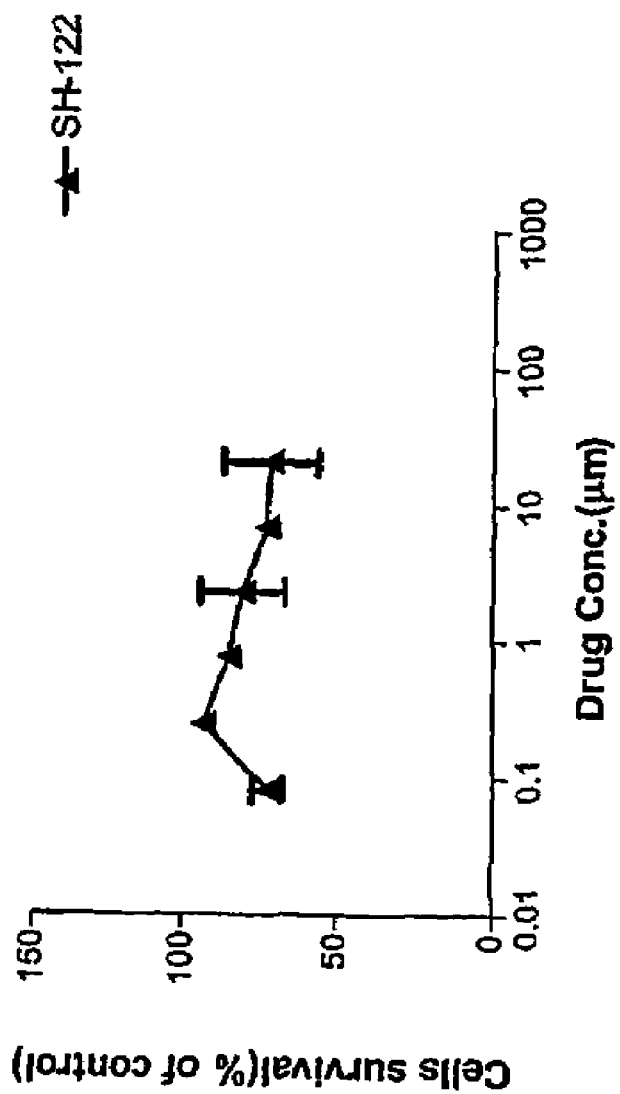
FIG. 31 shows the inhibition of growth of normal prostate cells in response to SH-122.

To test the effect of [6.3.0] Smac mimetics in inhibition of cell growth in human cancer cells, compounds were administered to several different cancer cell lines. BT-549, MDA-MB-231 (subclone 2LMP), and MDA-MB-231 (ATCC) human breast cancer cells and PC-3 human prostate cancer cells were seeded in 96-well plates with increasing concentrations of the compounds. To assay for the selectivity of the compounds for cancer cells, normal prostate epithelial cells were also tested. The cells were then incubated at 37° C. with 5% $CO_2$ for 5 days, followed by detection of cell viability with WST-8. Untreated cells were used as 100% growth. The compounds tested were SH-109, SH-122 and SH-123 (Table 6). Each of the compounds inhibited the cell growth of each of the cancer cell lines, with SH-122 being the most potent in each cell line (FIGS. 27-30). In contrast SH-122 had no cell growth inhibition effect on normal prostate epithelial cells, suggesting that the compounds of the present invention have specificity for cancer cells (FIG. 31). These results indicate that N-substituted Smac mimetics, such as SH-122, unexpectedly have similar XIAP binding affinities as non-substituted Smac mimetics, and are far more potent in terms of inhibition of cell growth.

Example 16

Figure 32:
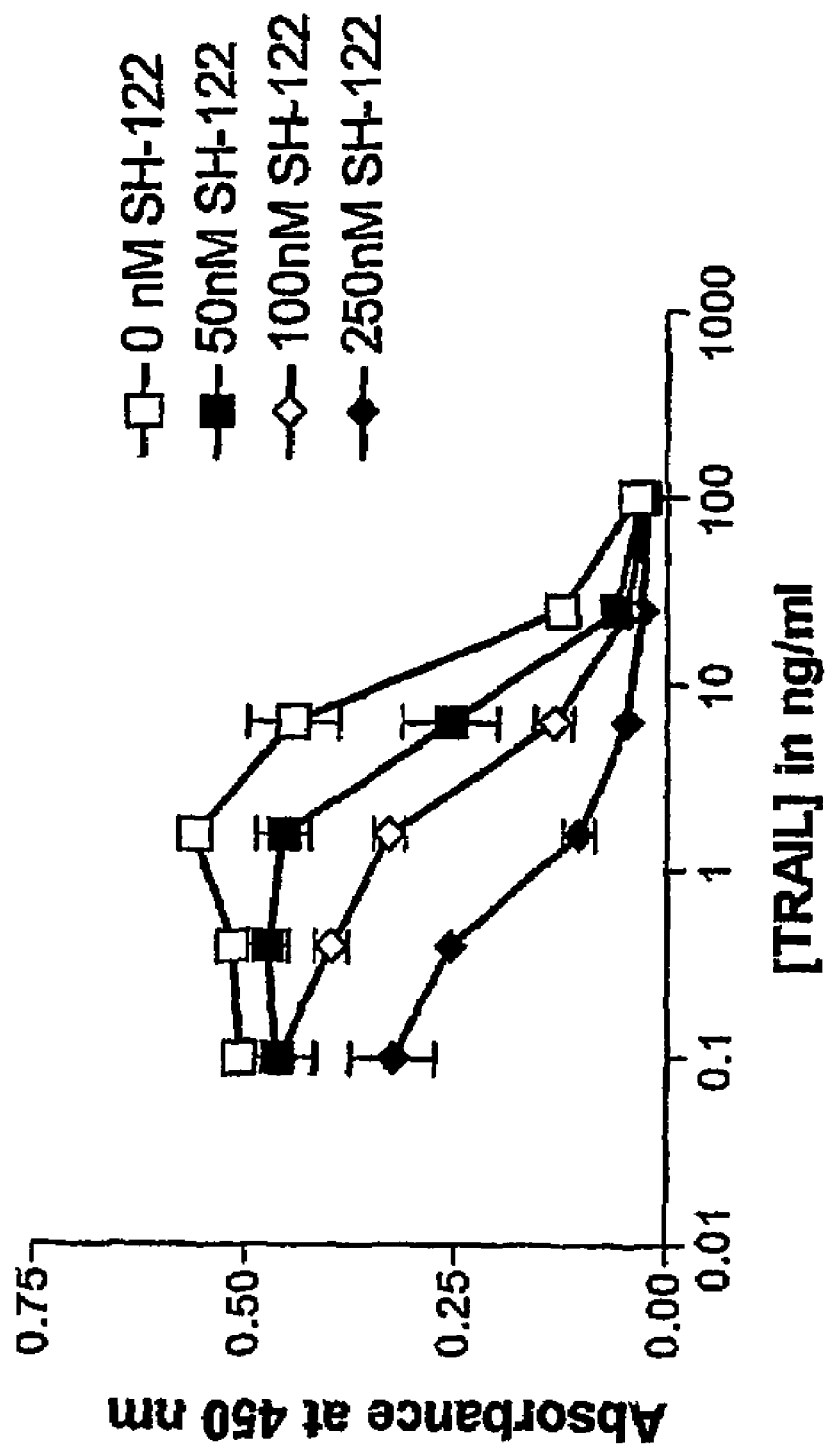
FIG. 32 shows the inhibition of growth of breast cancer cells in response to SH-122 and TRAIL.

Inhibition of Cell growth by SH-122 in Combination with TRAIL in Human Cancer Cells To test the ability of SH-122 to enhance the cell growth inhibitory activity of TRAIL, MDA-MB-231 (subclone 2LMP) breast cancer cells were seeded in 96-well plates with various concentrations of TRAIL in the presence of increasing amounts of SH-122. The cells were then incubated at 37° C. with 5% $CO_2$ for 4 days, followed by detection of cell viability with WST-8. TRAIL by itself inhibited the growth of the cells in a dose dependent fashion (FIG. 32). Increasing amounts of SH-122 enhanced the effect of TRAIL, with 250 nM SH-122 decreasing the $IC_{50}$ of TRAIL approximately ten-fold (FIG. 32). These results indicate that SH-122 is capable of potentiating the activity of TRAIL in inhibiting the growth of cancer cells.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound having Formula I:

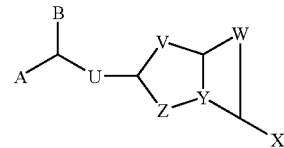

or a pharmaceutically acceptable salt thereof, wherein:

A is $NR_1R_2$, or $N^+R_1R_2R_3$;

$R_1$, $R_2$, and $R_3$ are independently hydrogen or optionally substituted $C_{1-8}$ alkyl, $C_{2-8}$ alkenyl, or $C_{2-8}$ alkynyl, in which one or more carbons can be replaced by C=O, C=S, or a heteroatom selected from O, S, and N, and one or more hydrogens in CH, $CH_2$ or $CH_3$ groups can be replaced by fluorine, a branched or unbranched alkyl or cycloalkyl, an optionally substituted aryl, alkylaryl, heteroaryl, or alkylheteroaryl, or $OR_4$, $SR_4$, or $NR_4R_5$;$R_4$, and $R_5$ are independently hydrogen or optionally substituted $C_{1-4}$ alkyl, $C_{2-5}$ alkenyl, or $C_{2-5}$ alkynyl, in which one or more carbons can be replaced by a heteroatom selected from O, S, and N, or optionally substituted aryl, alkylaryl, heteroaryl, or alkylheteroaryl; or any two of $R_1$, $R_2$, and $R_3$ taken together with the nitrogen to which they are attached form a heterocyclic group, in which one or more carbon atom can be replaced by C=O, C=S, or a heteroatom selected from O, S, and N, with the proviso that the heteroatom is separated from the nitrogen atom by at least two carbons;

B is optionally substituted $C_{1-4}$ alkyl, $C_{2-4}$ alkenyl, or $C_{2-4}$ alkynyl, wherein one or more hydrogens can be replaced by fluorine;

U is CONH, C(O)O, C(S)O, C(S)NH, C(NH)NH, or $(CH_2)_{1-5}$, wherein one or more carbons can be replaced by a heteroatom selected from O, S, and N;

V and W are independently $(CH_2)_{1-5}$, wherein one or more carbons can be replaced by C=O, C=S, or a heteroatom selected from O, S, and N, and one or more hydrogens in $CH_2$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;

X is optionally substituted $C_{1-18}$ alkyl, $C_{2-18}$ alkenyl, $C_{2-18}$ alkynyl, aryl, or heteroaryl, wherein one or more carbons can be replaced by C=O, C=S, or a heteroatom selected from O, S, and N, and one or more hydrogens in CH, $CH_2$ or $CH_3$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$; Y is N and forms a bicyclic ring system with one of the ring being a seven-membered ring;

Z is $CH_2$, C=O, C=S, CHSR, CHOR, or CHNR; and

R is hydrogen or optionally substituted $C_{1-4}$ alkyl, $C_{2-4}$ alkenyl, or $C_{2-4}$ alkynyl.

2. The compound of claim 1, having formula IV:

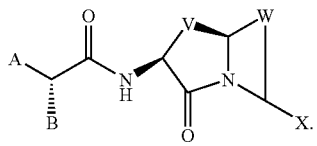

IV

3. A pharmaceutical composition comprising a compound of claim 1 and a pharmaceutically acceptable carrier.

4. The pharmaceutical composition of claim 3, wherein said compound has formula IV:

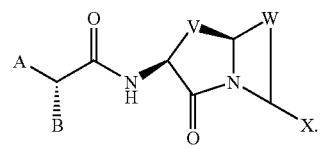

IV

* * * * *